(12) United States Patent
Rossi et al.

(10) Patent No.: US 6,531,466 B2
(45) Date of Patent: Mar. 11, 2003

(54) TRICYCLIC CARBAPENEM COMPOUNDS

(75) Inventors: Tino Rossi, Verona (IT); Daniele Andreotti, Verona (IT); Giovanna Tedesco, Verona (IT); Luca Tarsi, Verona (IT); Emiliangelo Ratti, Verona (IT); Aldo Feriani, Verona (IT); Domenica Antonia Pizzi, Verona (IT); Giovanni Gaviraghi, Verona (IT); Stefano Biondi, Verona (IT); Gabriella Finizia, Verona (IT)

(73) Assignee: GlaxoSmithKline SpA, Verona (IT)

( * ) Notice: Subject to any disclaimer, the term of this patent is extended or adjusted under 35 U.S.C. 154(b) by 0 days.

(21) Appl. No.: 09/781,292

(22) Filed: Feb. 13, 2001

(65) Prior Publication Data

US 2001/0047094 A1 Nov. 29, 2001

Related U.S. Application Data

(63) Continuation of application No. 09/284,998, filed as application No. PCT/EP97/06299 on Nov. 12, 1997, now abandoned.

(30) Foreign Application Priority Data

Nov. 14, 1996 (GB) .............................................. 9623684

(51) Int. Cl.⁷ ...................... C07D 477/14; A61D 31/04; A61K 31/407; A61K 31/428
(52) U.S. Cl. ................................. 514/210.03; 540/302
(58) Field of Search ...................... 540/302; 514/210.03

(56) References Cited

FOREIGN PATENT DOCUMENTS

| EP | 0 416 953 A | 3/1991 |
|---|---|---|
| EP | 0 422 596 A | 4/1991 |
| EP | 0 507 313 A | 10/1992 |

OTHER PUBLICATIONS

Patent abstracts of Japan, vol. 018, No. 495 (Sep. 16, 1994), For JP 6–166688.
Patent abstracts of Japan, vol. 097, No. 001 (Jan. 13, 1997). For JP 8–245628.

*Primary Examiner*—Mark L Berch
(74) *Attorney, Agent, or Firm*—Bacon & Thomas

(57) ABSTRACT

A compound of formula (I), salts and metabolically labile esters thereof, wherein R represents optionally substituted aryl or heteroaryl group; A represents a propylene chain or A is a chain of 3 members one of which is selected from an oxygen or sulphur atom or the group NH or a substituted derivative thereof and the other two members are methylene groups, having antibacterial activity, processes for their preparation and to their use in medicine.

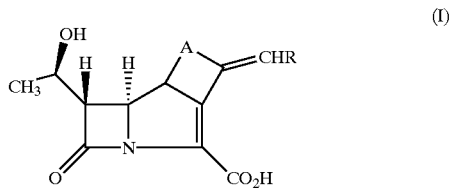

(I)

12 Claims, No Drawings

TRICYCLIC CARBAPENEM COMPOUNDS

This application is a continuation of Application No. 09/284,998, filed Jul. 12, 1999 (of which the entire disclosure of the prior application is hereby incorporated by reference) ABN, which is a 371 of PCT/EP97/06299, filed Nov. 12, 1997.

This invention relates to exomethylene derivatives having antibacterial activity, to processes for their preparation, to compositions containing them and to their use in medicine.

European Patent Application publication No. 0416953A2 describes 10-(1-hydroxyethyl)-11-oxo-1-azatricyclo[7,2,0,0$^{3,8}$]undec-1-ene-2-carboxylic acid and certain 4 substituted derivatives thereof, which have antibacterial activity.

European Patent Application publication No. 0422596A2 describes compound of the general formula

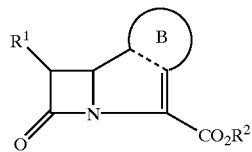

wherein $R^1$ is inter alia a 1-hydroxyethyl group, $CO_2R^2$ is a carboxy group which may optionally be esterified and ring B is a cyclic group which may be optionally substituted. Ring B may inter alia be a six membered ring containing a single heteroatom selected oxygen, sulphur or nitrogen or a cyclohexane ring. The compounds have antibacterial activity.

The present invention relates to compounds which have a particularly advantageous profile of anti-bacterial activity, including good activity against gram positive microorganisms such as methicillin resistant Staphylococcus aureus (MRSA) and methicillin resistant Staphylococcus epidermidis (MRSE).

Thus the present invention, provides compounds of general formula (I)

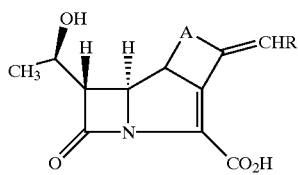

(I)

salts and metabolically labile esters thereof, wherein R represents optionally substituted aryl or heteroaryl group;

A represents a propylene chain or A is a chain of 3 members one of which is selected from an oxygen or sulphur atom or the group NH or a substituted derivative thereof and the other two members are methylene groups.

In addition to the fixed stereochemical arrangement as defined in formula (I) the molecule contains a further asymmetric carbon atom at the bridged carbon atom to which A group is attached.

It will be appreciated that all stereoisomers including mixtures thereof arising from this additional asymmetric centre are within the scope of the compounds of formula (I). Further, in formula(I) the exocycle double bond can exist in trans(E) or cis(Z) configuration and the invention includes all such isomers and mixtures thereof. Salts of compounds of formula (I) include base addition salts for use in medicine; such salts are formed with bases that have a physiologically acceptable cation. Suitable cations include those of alkali metals (e.g. sodium or potassium), alkaline earth metals (e.g. calcium), amino acids (e.g. lysine and arginine) and organic bases (e.g. procaine, phenylbenzylamine, dibenzylethylenediamine, ethanolamine, diethanolamine, and N-methyl glucosamine).

Salts derived from bases wherein the cation is not physiologically acceptable may be useful as intermediates for the preparation and/or isolation of other compounds of the invention, and these salts also form part of the invention.

When group R contains a basic nitrogen atom the invention also includes acid addition salts and quaternary ammonium salts thereof. Such salts and quaternary ammonium salts include internal salts formed with the carboxylic acid group in the molecule.

Suitable acid addition salts are those formed with physiologically acceptable inorganic or organic acids. Examples of suitable quaternary ammonium salts are those formed by reaction of an appropriate compound of formula (I) or a protectived derivative thereof with a $C_{1-4}$ alkyl halide or carbamoyl $C_{1-4}$ alkyl halide or equivalent thereof.

It will be appreciated that the compounds of formula (I) may be produced in vivo by metabolism of a suitable metabolically labile ester. Such prodrugs include for example physiologically acceptable metabolically labile esters of compounds of the general formula (I). These may be formed by esterfication, for example of any of the carboxylic acid groups in the parent compound of general formula (I) with, where appropriate, prior protection of any other reactive groups present in the molecule followed by deprotection if required.The types of esters grouping that may be used as metabolically esters are those widely used in pharmaceutical chemistry and are well known to those skilled in the art.

The compound of formula (I), salts thereof and metabolically labile esters thereof, may form solvates (e.g. hydrates) and the invention includes all such solvates.

The general formula (I) as drawn includes at least two stereoisomers and mixtures thereof may be represented by the formulae(1 a, 1b)

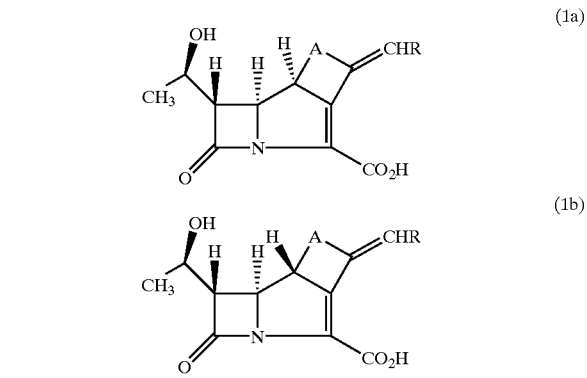

The solid wedge shaped bond indicates that the bond is above the plane of the paper. The broken bond indicates that the bond is below the plane of the paper.

The configuration for the bridged carbon atom to which A is attached shown in formula (1 a) is hereinafter referred to as β configuration and in formula (1b) as the α configuration. In the specific compounds named below the assignment of R or S configuration has been made according to the rules of Cahn. Ingold and Prelog,Experientia 1956 12, 81. Thus for example when A is a propylene chain the β configuration for the carbon at the 8 position corresponds to the S isomer and the α configuration corresponds to the R isomer.

The term optionally substituted aryl as a group or part of a group when used herein refers to an optionally substituted phenyl, a phenyl fused to one 5 or 6 membered saturated or unsaturated carbocyclic group to form a fused bicyclic carbocyclic group or a phenyl fused to two phenyl groups to form a fused tricyclic group. The term optionally substituted heteroaryl as a group or part of a group when used herein refers to a monocyclic, fused bicyclic or fused tricyclic heteroaryl group, which is attached to the carbon atom of the exocyclic double bond via a carbon atom member of the heteroaryl ring.

Example of suitable fused bicyclic carbocyclic groups include naphthyl, 1,2,3,4 tetrahydronaphthyl, indenyl or indanyl. The term fused tricyclic carbocyclic group preferably refers to a phenanthrene or antharacene Suitable monocyclic heteroaryl groups includes a 5 or 6 membered heteroaryl group in which the 5-membered ring contains 1 or 2 heteroatoms selected from oxygen, sulphur or nitrogen and 6-membered ring containing 1 or 2 nitrogen atoms. Examples of such heteroaryl groups include furanyl, thiophenyl, imidazolyl, oxazolyl, thiazolyl, pyrazolyl, pyridyl, pyridinium, pyridazinyl, pyrimidinyl .

Suitable fused bicyclic heteroaryl groups contain 9 or 10 ring members having at least one heteroatom selected from oxygen, sulphur and nitrogen. Conveniently the fused bicyclic heteroaryl group contains from 1 to 3 hetero atoms and examples of such groups include quinolinyl, benzofuranyl, benzimidazolyl, benzothienyl, benzoxazolyl, indolyl, benzothiazolyl, furylpyridine or oxazolopyridyl.

Suitable fused tricyclic hetoraryl groups contain 13 or 14 ring members having at least one heteroatom selected from oxygen, sulphur and nitrogen. Examples of such groups include carbazolyl, β-carbolinyl, phenanthridinyl, acridinyl. Where the heteroaryl ring as above defined contains a basic nitrogen atom the invention also includes quaternary derivatives thereof such as $C_{1-4}$ alkyl, carbamoyl $C_{1-4}$ alkyl quaternary derivatives thereof. When A is chain 3 members and wherein one of the members is a group selected from oxygen, sulphur or NH (or a substituted derivative thereof) suitable examples of such chains include:

—OCH$_2$CH$_2$—, —CH$_2$OCH$_2$—, —SCH$_2$CH$_2$, —CH$_2$SCH$_2$—, CH$_2$CH$_2$S, NHCH$_2$CH$_2$, or —CH$_2$NH—CH$_2$—.

When a member of the chain A is a substituted NH group examples of suitable substitutents include $C_{1-4}$ alkyl (e.g methyl),benzyl, acetyl, $C_{1-4}$ alkoxycarbonyl, allyloxycarbonyl or an optionally substituted phenyloxycarbonyl group.

When R is a substituted phenyl group or a substituted monocyclic heteroaryl group these groups are substituted by one to 3 substituents which may be the same or different and selected from alkyl, optionally substituted alkenyl, alkynyl, halogen, cyano, nitro, trifluoromethyl, by one or two (CH$_2$)$_n$ R$_1$ groups wherein n is zero or an integer from 1 to 4 and R$_1$ is hydroxy, $C_{1-4}$ alkoxy, $C_{1-4}$ alkanoyl-amino, NR$_2$R$_3$ (wherein R$_2$ and R$_3$ independently represent hydrogen or $C_{1-4}$ alkyl), optionally substituted phenyl, phenoxy monocyclic heteroaryl, COR$_4$ (wherein R$_4$ is hydroxy $C_{1-4}$ alkoxy or NR$_2$R$_3$) SO$_2$R$_5$, (wherein R$_5$ is $C_{1-4}$ alkyl or the group NR$_2$R$_3$), or R$_1$ is a pyrrolidino or piperidino group attached to the rest of the molecule via a carbon atom in the group and in which the nitrogen atom may be substituted by a $C_{1-4}$ alkyl group.

When R is a fused bicyclic or tricyclic heteroaryl group such groups are substituted by one to 2 substituents which may be the same or different and selected from alkyl, halogen, cyano, nitro, trifluoromethyl, NR$_2$R$_3$ (wherein R$_2$ and R$_3$ independently represent hydrogen or $C_{1-4}$ alkyl).

The term alkyl as a group or part of a group used herein refers to a straight or branched chain alkyl group, containing from 1 to 6 carbon atoms e.g. methyl, ethyl, propyl, isopropyl, butyl, isobutyl, t-butyl$_1$ pentyl, isopentyl or hexyl.

The term optionally substituted alkenyl as a group or part of a group used herein refers to a straight or branched chain alkenyl group of 3 to 6 carbon atoms such as propenyl, butenyl or pentenyl, which may be substituted by one or more group selected from $C_{1-4}$ alkyl , halogen , hydroxy, carboxyl, nitro, cyano, trifluoromethyl, trifluoromethoxy, phenyl.

The term alkynyl as a group or part of group used herein refers to a straight or branched chain alkynyl group of 2 to 6 carbon atoms such as ethynyl, propynyl, butynyl, or pentynyl, which may be substituted by one or more group selected from $C_{1-4}$ alkyl halogen hydroxy, nitro, cyano, trifluoromethyl, trifluoromethoxy, phenyl. The term halogen when used herein means fluorine, chlorine, bromine or iodine In the compounds of formula(I) the exocyclic double bond is conveniently in trans (E) configuration.

A preferred class of compounds of formula(I) are those wherein A is the group —CH$_2$—O—CH$_2$—, CH$_2$—S—CH$_2$—, —CH$_2$NHCH$_2$—, or —(CH$_2$)$_3$— and more preferably A is —CH$_2$—S—CH$_2$ or more particularly 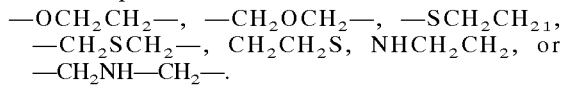

For compounds of formula (I) wherein A is propylene chain, those in which the carbon atom at the 8- position is in β configuration represent a further preferred class of compounds according to the invention.

When R group is optionally substituted phenyl it is conveniently substituted by one to two groups selected from halogen (e.g fluorine, chlorine, bromine), alkoxy(e.g methoxy, ethoxy), hydroxy, cyano, nitro, trifluoromethyl, $C_{1-4}$ alkyl(e.g methyl or tert butyl), hydroxymethyl, phenoxy or optionally substituted monocyclic heteroaryl (e.g 4-pyridyl, pyrazolyl, thiazolyl).

When R is an optionally substituted monocyclic heteroaryl group this is conveniently pyridyl such as 2-pyridyl, 3-pyridyl or preferably 4-pyridyl [optionally substituted by 1 to 3 groups selected from $C_{1-4}$ alkyl (e.g methyl) halogen (e.g chloride or bromide) nitro, amino, $C_{1-4}$ alkanoyl amino e.g. acetyl amino, cyano hydroxy, alkoxy (e.g methoxy), N-alkyl pyridinium (e.g N-methyl pyridinium), thiophenyl (optionally substituted by -methyl, pyridyl e.g. 4-pyridyl or pyridinium), thiazolyl (optionally substituted by phenyl, pyridyl e.g. 4-pyridyl or N-carbamoymethyl-pyridinum), pyrimidinyl e.g. 4-pyrimidinyl or 5-pyrimidinyl, or piperidinyl e.g. 4-piperidinyl.

When R is an optionally substituted bicyclic hetereroaryl group this is conveniently a quinolinyl e.g. 4-quinolinyl, benzofuranyl, e.g. 2-benzofuranyl, benzothiophenyl e.g. 2-benzothiophenyl or 3-benzothiophenyl, benzothiazolyl, e.g. 2-benzothiazolyl, oxazolo pyridyl optionally substituted by the group NR$_2$R$_3$ or furyl pyridine group or quaternary salt thereof.

When R is an optionally substituted tricyclic heteroaryl group this is conveniently an optionally substituted carbazolyl group e.g. N-ethyl carbazotyl.

A preferred class of compounds of formula (I) are those wherein A is propylene chain, —CH$_2$S—CH$_2$— or (CH$_2$)$_3$— and more particularly —(CH$_2$)$_3$—.

A particularly preferred group of compounds of formula (I) is that wherein R is pyridyl and more especially 4 pyridyl (optionally substituted by one or two substituents which may be the same or different selected from methyl, chlorine, methoxy, nitro, amino, acetylamino, cyano), 2-thiophenyl (optionally substituted by methyl, pyrid-4-yl, carbamoylmethyl, 2-thiazolyl (optionally substituted by phenyl, pyrid-4-yl, 4-piperidinyl, 3-benzothiophenyl, 2-benzothiophenyl, 2-benzothiazolyl, 2-benzofuranyl., 2-diethylaminooxazolo [4,5-c] pyrid-7-yl or 2-furyl [3,2-c] pyridine or phenyl or phenyl substituted by one or two substituents which may be the same or different selected from fluorine, chlorine, nitro, cyano, hydroxy, hydroxymethyl, phenoxy, pyridyl, e.g. pyrid-4-yl.

A particular preferred compound of the invention is:

Sodium (8S,9R,10S,12R)-1-aza-10-(1-hydroxyethyl)-11-oxo-4-[(E)-(pyridin-4-yl)methylene]-tricyclo-[7,2,0,0$^{3.8}$]-undec-2-ene-2-carboxylate Further preferred compounds according to the invention include:

Sodium(8S,9R,10S,12R)-1-aza-10-(1-hydroxyethyl)-11-oxo-4-[(E)-phenylmethylene]-tricyclo-[7,2,0,0$^{3.8}$]-undec-2-ene-2-carboxylate Sodium (8S,9R,10S,12R)-1-aza-10-(1-hydroxyethyl)-11-oxo-4-[(E)-(4(4'-pyridyl) thiazol-2-yl)methylene]-tricyclo-[7,2,0,0$^{3.8}$]-undec-2-ene-2-carboxylate Sodium (8S,9R,10S,12R)-1-aza-10-(1-hydroxyethyl)-11-oxo-4-[(E)-(-4-benzothiazol-2-yl)methylene]-tricyclo-[7,2,0,0$^{3.8}$]-undec-2-ene-2-carboxylate Sodium (8S,9R,10S,12R)-1-aza-10-(1-hydroxyethyl)-11-oxo-4-[(E)-(4-(4'-(piperidin-4yl) thiazol-2-yl) methylene]-tricyclo-[7,2,0,0$^{3.8}$]-undec-2-ene-2-carboxylate Sodium (8S,9R,10S,12R)-1-aza-10-(1-hydroxyethyl)-11-oxo-4-(E)-(4-nitrophenyl)methylene]-tricyclo-[7,2,0,0$^{3.8}$]-undec-2-ene-2-carboxylate Sodium (8S,9R,10S,12R)-1-aza-10-(1-hydroxyethyl)-11-oxo-4-[(E)-(4-phenylthiazol-2-yl)methylene]-tricyclo-[7,2,0,0$^{3.8}$]-undec-2-ene-2-carboxylate Sodium (8S,9R,10S,12R)-1-aza-10-(1-hydroxyethyl)-11-oxo-4-[(E)-(3-(4'-pyridyl) phenyl)methylene]-tricyclo-[7,2,0,0$^{3.8}$]-undec-2-ene-2-carboxylate Sodium (8S,9R,10S,12R)-1-aza-10-(1-hydroxyethyl)-11-oxo-4-[(E)-(2,6-dimethylpyridin-4-methylene]-tricyclo-[7,2,0,0$^{3.8}$]-undec-2-ene-2-carboxylate Sodium (8S,9R,10S,12R)-1-aza-10-(1-hydroxyethyl)-11-oxo-4-[(E)-(2-methylpyridin-4-yl)methylene]-tricyclo-[7,2,0,0$^{3.8}$]-undec-2-ene-2-carboxylate Sodium (8S,9R,10S,12R)-1-aza-10-(1-hydroxyethyl-11-oxo-4-[(E)-[(benzofuran-2-yl)methylene]-triciclo-[7,2,0,0$^{3.8}$]-undec-2-ene-carboxylate.

Sodium (8S,9R,10S,12R)-1-aza-10-(1-hydroxyethyl)-11-oxo-4-[(E)-[(2-chloropyrid-4-yl)methylene]-triciclo-[7,2,0,0$^{3.8}$]-undec-2-ene-carboxylate.

Sodium (8S,9R,10S,12R)-1-aza-10-(1-hydroxyethyl)-11-oxo-4-[(E)-[(2-furyl[3,2-c]pyridine)methylene]-triciclo-[7,2,0,0$^{3.8}$]-undec-2-ene-carboxylate.

Sodium (8S,9R,10S,12R)-1-aza-10-(1-hydroxyethyl)-11-oxo-4-[(E)-(2-aminopyrid-4-yl)methylene]-tricyclo-[7,2,0,0$^{3.8}$]-undec-2-ene-2-carboxylate Sodium (8S,9R,10S,12R)-1-aza-10-(1-hydroxyethyl)-11-oxo-4-[(E)-(4-chloro-3-nitro-phenyl)methylene]-tricyclo-[7,2,0,0$^{3.8}$]-undec-2-ene-2-carboxylate Sodium(8S,9R,10S,12R)-1-aza-10-(1-hydroxyethyl)-11-oxo-4-[(E)-(benzothiophen-2-yl)methylene]-tricyclo-[7,2,0,0$^{3.8}$]-undec-2-ene-2-carboxylate Sodium(8S,9R,10S,12R)-1-aza-10-(1-hydroxyethyl)-11-oxo-4-[(E)-(benzothiophen-3-yl)methylene]-tricyclo-[7,2,0,0$^{3.8}$]-undec-2-ene-2-carboxylate Sodium (8S9S,10S,12R)-1-aza-10-(1-hydroxyethyl)-6-thia-11-oxo-4-[(E)-(4-pyridyl)methlene-tricyclo-[7,200$^{3.8}$]-indec-2-ene-2-carboxylate.

The compounds of the present invention have been found to exhibit a useful profile of activity against gram positive microorganisms, such as methicillin resistant *Staphylococcus aureus* (MRSA), methicillin resistant *Staphylococcus epidermidis*(MRSE).

Compounds according to the invention also exhibit a broad spectrum of antibacterial activity against a wide range of clinical pathogenic microorganisms, For example using a standard microtiter broth serial dilution test compounds of the invention have been found to exhibit useful levels of activity against a wide range of pathogenic microorganisims including strains of *Staphylococcus aureus*, methicillin resistant *Staphylococcus aureus* (MRSA), methicillin resistant *Staphylococcus epidermidis* (MRSE), *Enterococcus faecalis, Escherichia coli, Hemophilus influenzae, Klebisiella, pneumoniae, Clostridium perfringens, Moraxelia catarrhalis, Streptococcus pneumoniae.*

Compounds of the invention exhibit a very high resistance to all β-lactamases and are also relatively stable to renal dehydropeptidase.

The compounds of the invention may therefore be used for treating a variety of diseases caused by pathogenic bacteria in human beings and animals.

Thus, according to another aspect of the present invention, we provide a compound of formula (I) or a physiologically acceptable salt thereof for use in the therapy or prophylaxis of systemic or topical bacterial infections in a human or animal subject.

According to a further aspect of the invention we provide the use of a compound of formula (I) or a physiologically acceptable salt thereof for the manufacture of a therapeutic agent for the treatment of systemic or topical bacterial infections in a human or animal body.

According to a yet further aspect of the invention we provide a method of treatment of the human or non-human animal body to combat bacterial infections which method comprises administering to the body an effective amount of a compound of formula (I) or a physiologically acceptable salt thereof.

While it is possible that, for use in therapy, a compound of the invention may be administered as the raw chemical it is preferable to present the active ingredient as a pharmaceutical formulation.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in conventional manner with the aid of one or more suitable carriers or excipients. The compositions of the invention include those in a form especially formulated for parenteral, oral, buccal, rectal, topical, implant, ophthalmic, nasal or genito-urinary use.

The compounds according to the invention may be formulated for use in human or veterinary medicine by injection (e.g. by intravenous bolus injection or infusion or via intramuscular, subcutaneous or intrathecal routes) and may be presented in unit dose form, in ampoules, or other unit-dose containers, or in multidose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

The compounds according to the invention may be formulated for topical administration, for use in human and veterinary medicine, in the form of ointments, creams, gels, lotions, shampoos, powders, (including spray powders), pessaries, tampons, sprays, dips, aerosols, drops (e.g. eye ear or nose drops) or pour-ons.

Aerosol sprays are conveniently delivered from pressurised packs, with the use of a suitable propellant, eg dichlorodifluoromethane, trichlorofluoromethane, dichtorotetrafluoroethane, carbon dioxide or other suitable gas.

For topical administration by inhalation the compounds according to the invention may be delivered for use in human or veterinary medicine via a nebuliser.

The pharmaceutical compositions for topical administration may also contain other active ingredients such as corticosteroids or antifungals as appropriate.

The compositions may contain from 0.01–99% of the active material. For topical administration, for example, the composition will generally contain from 0.01–10%, more preferably 0.01–1% of the active material.

For systemic administration the daily dose as employed for adult human treatment will range from 2–100 mg/kg body weight, preferably 5–60 mg/kg body weight, which may be administered in 1 to 4 daily doses, for example, depending on the route of administration and the condition of the patient When the composition comprises dosage units, each unit will preferably contain 200 mg to 1 g of active ingredient.

The duration of treatment will be dictated by the rate of response rather than by arbitrary numbers of days.

Compounds of general formula(I) and salts thereof may be prepared by general method outlined hereinafter. In the following description, the groups R and A have the meaning defined for the compounds of formula (I) unless otherwise stated The compounds of formula (I) may be obtained by the cyclisation of the compounds of formula (II) wherein A and R have the meaning as defined in formula (I) or are protected derivatives thereof, $R_6$ is hydrogen atom or hydroxyl protecting group and $R_7$ is hydrogen or a carboxyl protecting group,

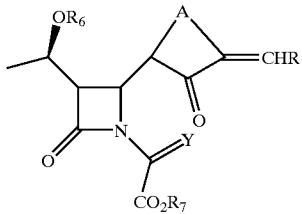

Y is an oxygen atom or a phosphine group, and if required or desired subjecting the resulting compound prior to or subsequent to any separation into its stereochemical isomers, to one or more of the following operations:
 a) removal of one or more protecting groups
 b) conversion of a compound in which $R_7$ is a hydrogen atom or a carboxyl protecting group into a salt of an inorganic or organic base, an acid addition salt thereof or a metabolically labile ester thereof.

The cyclisation of a compound of formula (II) in which Y is oxygen is conveniently carried out by heating in the presence of an organic phosphite. The reaction is preferably carried out in a solvent or mixture of solvents at a temperature within the range 60–200°.

Suitable solvents include hydrocarbons with an appropriate boiling point, for example aromatic hydrocarbons, such as toluene or xylene.

Suitable organic phosphites include acyclic and cyclic trialkylphosphites, triarylphosphites and mixed alkylarylphosphites. Particularly useful organic phosphites are the trialkylphosphites e.g. trethylphosphite or trimethylphosphite or dialkoxy alkyl phosphite e.g. diethoxy methyl phosphite. The cyclisation of a compound of formula (II) in which Y is a phosphine grouping is preferably carried out in a solvent at a temperature between 40–200° C.

Suitable solvents include hydrocarbons such as aromatic hydrocarbons, for example xylene or toluene, aliphatic hydrocarbons and halogenated hydrocarbons such as dichloromethane, chloroform and trichloroethane. Examples of suitable phosphine groups are triarylphosphines e.g. triphenyl phosphine or trialkylphospines e.g. tri-t-butylphospine. In these reactions when it is necessary or desirable to use a hydroxyl protecting group $R_6$ suitable hydroxyl protecting groups include trialkylsilyl e.g. trimethylsilyl or t-butyldimethylsilyl.

Suitable carboxyl protecting groups $R_7$ for use in these reactions include arylmethyl groups such as benzyl, p-nitrobenzyl, t-butylbenzyl or trityl, allyl or substituted allyl groups, fluoroenylmethyl or trialkylsilylalkyl e.g. trimethylsilyl ethyl.

The hydroxyl and carboxyl protecting groups $R_6$, $R_7$ may be removed by conventional procedures and in any order. More preferably however the hydroxyl protecting group $R_6$ is removed prior to the removal of the carboxyl protecting group.

The hydroxyl protecting groups may be removed by well known standard procedures such as those described in Protective Groups in Organic Chemistry, pages 46–119, edited by J. F. W. Mc Omie (Plenum Press, 1973). For example when $R_6$ is a t-butyldimethylsilyl group, this may be removed by treatment with tetrabutylammonium fluoride and acetic acid or by reaction with fuoride ions source such as triethyl amine tris(hydrogen fluoride) or diisopropylethylamine tis(hydrofluride) This process is conveniently carried out in a solvent such as tetrahydrofuran. Similarly when $R_6$ is a 4-nitrobenzyloxycarbonyloxy group this may be removed by treatment with hydrogen and a metal catalyst e.g palladium on carbon.

The carboxyl protecting group $R_7$ may also be removed by standard processes such as those described in Protective Groups in Organic Chemistry, pages 192–210, edited by J. F. W. Mc Omie (Plenum Press 1973). For example when $R_7$ represents an arylmethyl group this may be removed by conventional procedures using hydrogen and a metal catalyst e.g. palladium. When the group $R_7$ represents an allyl or substituted allyl group then this is preferably removed by treatment with an allyl acceptor in the presence of tetrakis(triphenylphosphine) palladium and optionally in the presence of triphenylphospine. Suitable allyl acceptors include sterically hindered amines such as tertbuylamine, cyclic secondary amines such as morpholine or thiomorpholine, tertiary amines such as triethylamine, aliphatic or cycloapliphatic β-dicarbonyl compounds such as acetylacetone, ethyl acetoacetate or dimedone, an alkanoic acids or alkali metal salts thereof such as acetic acid, propionic acid or 2-ethyl hexanoic acid or the potassium or sodium salt thereof, or tributyl tinhydride.

Particularly useful allyl acceptors are sodium 2-ethyl hexanoate or tributyl tin hydride.

The reaction is preferably carried out in an inert solvent such as an ether e.g. diethyl ether or tetrahydrofuran, an alkanol e.g. ethanol, an ester e.g. ethyl acetate or a halohydrocarbon e.g. methylene chloride, or mixtures thereof. The reaction is conveniently carried out in the temperature range 0°–40° more particularly at room temperature.

When $R_7$ is a fluoroenylmethyl group this is conveniently removed by reaction with an amine such as dipropylamine a solvent such as a ketone e.g. acetone.

In one embodiment compounds of formula (II) may be prepared by reaction of the compound (III)

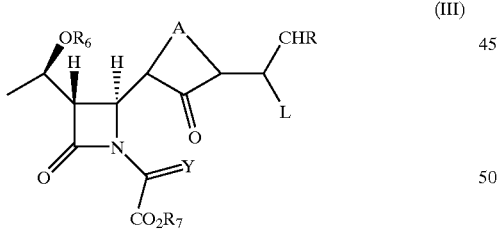

(III)

wherein A and R have the meaning as defined in compound of formula (I), Y represents a phosphine group, L is a leaving group such as methanesulphonyl, p-toluen sulphonyl group or chlorine atom, $R_6$ is hydroxyl protecting group and $R_7$ is carboxyl protecting group , with an organic base such as 1,8-diazabicyclo[5.4.0] undec-7-ene. The reaction is conveniently carried out in an aprotic solvent such as a halohydrocarbon (e.g dichloromethane) at a temperature within the range 0–37° C. In a further embodiment compounds of formula(II) in which Y=O may be prepared by treating a compound of formula (IV), in which the groups $R_6$, R, A have the meanings given above, with an activated derivative of the acid (V) in which $R_7$ is a carboxyl protecting group.

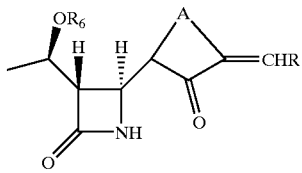

(IV)

HOOCCO$_2$R$_7$ (V)

Suitable activated derivatives of the acid (V) include the corresponding acyl halides e.g. acyl chloride.

When the acyl halide is used as the activated derivative of the acid (V) then the reaction is preferably carried out in the presence of an acid acceptor such as a tertiary organic base for example pyridine or a trialkylamine in an aprotic solvent such as dichloromethane.

The compound of formula (II) in which Y is a phosphine group may be prepared by treating the intermediate (VI) in which X is a leaving group such as a halogen e.g. chlorine.

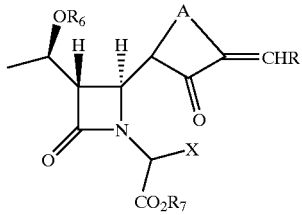

(VI)

with the corresponding phosphine e.g. triphenylphosphine in the presence of a base. The reaction is conveniently carried out in a solvent such as dioxan in the presence of a tertiary organic base, e.g. 2,6 lutidine.

The compounds of formula (VI) may be prepared form the corresponding hydroxy derivative (VII) by conventional means for converting hydroxyl groups into leaving groups.

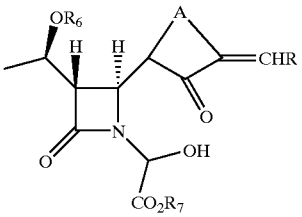

(VII)

Thus for example a compound of formula (VI) in which X is a chlorine atom may be prepared by treating a compound of formula (VII) with thionyl chloride in an aprotic solvent such as dioxan or tetrahydrofuran and in the presence of a tertiary organic base e.g. 2,6-lutidine. Compounds of formula (VII) may be prepared from the reaction of a compound of formula (IV) with glyoxylic ester (VIII; CHOCO$_2$R$_7$) preferably in the form of its hydrate or hemiacetal. The reaction is preferably carried out in an aprotic solvent such as toluene and in the Presence of an activated molecular sieve.

Compounds of formula (III) may be prepared from the corresponding hydroxy derivative (IX) by conventional means for converting hydroxyl groups into leaving groups.

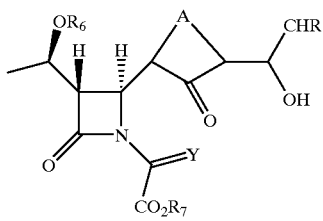

(IX)

Thus for example a compound of formula (III) in which L is methansulphonyl group may be prepared by treating a compound of formula (IX) with methansulphonyl chloride in an aprotic solvent such as dioxane dichloromethane or tetrahydrofuran and in the presence of a tertiary organic base e.g triethyl amine. The reaction is conveniently carried out at a temperature within the range 0° to +25° C.

Compounds of formula (IX) may be prepared by reaction of compounds of formula (X) in which $R_6, R_7$, A and Y have the meaning defined in formula (III) with the aldehyde (XI) wherein R has the meaning defined in formula(I) or is a protected derivative thereof, in the presence of a strong base such as lithium bis(trimethylsilyl)amide.

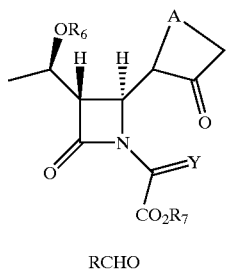

(X)

RCHO (XI)

The reaction is carried out in an aprotic solvent such as ether e.g tetrahydrofuran and at a temperature within the range −78° C. to +20° C. Compounds of formula(IV) may be prepared by treating the azetidinone (XII) with enolate ion of the ketone (XIII)

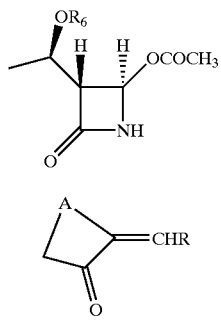

(XIII)

(XII)

The reaction is preferably carried out at a low temperature e.g −78° C. in a solvent such as tetrahydrofuran.

The enolate ion of the ketone(XII) is conveniently generated in situ by treatment with a suitable base such as Lithium bis(trimethylsilyl)amide.

Alternatively compounds of formula (IV) may be prepared from reaction of azetidinone(IX) with the enol ether (XIV), wherein R has the meaning defined in formula (I) and $R_8$ is a $C_{1-4}$ alkyl group

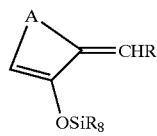

(XIV)

The reaction may be carried out in a solvent such as methylene chloride or acetonitrile in the presence of a Lewis acid such as stannic chloride. Compounds of formula (X) are either known or may be prepared according to the processes describing in EPA No.0416953A.

Compounds of formula (XIII) may be prepared by reaction of cyclohexanone derivative (XV) and aldehyde (XI)

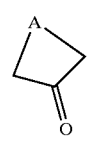

(XV)

RCHO (XI)

in the presence of a strong base such as lithium bis (trimethylsilyl)amide. Compounds of formutae (XI), (XV) are known compounds or may be prepared using methods described for analogous compounds.

In any of the formulae(I) to (X), shown above when there is an asymmetric carbon atom and no specific configuration is shown then the formula includes all possible configurations.

The processes described above for preparing the compounds of formula(Ii) will in general give a mixture of diastereoisomers.

The individual stereoisomers of the compounds of formula(II) may be prepared using the processes described above starting with the appropriate isomers of formula (III) or (IV).

Compounds of the invention in which the group $R_7$ is a physiologically acceptable cation may be prepared from compounds of the invention in which $R_6$ is hydrogen by treatment with a suitable base. Conveniently the salt is formed in solution and then if required precipitated by the addition of a non-solvent e.g. a non polar aprotic solvent. Alternatively the sodium or potassium salt may be prepared by treating a solution of a compound of formula (I) in which $R_7$ represents a hydrogen atom with a solution of sodium or potassium 2-ethylhexanoate in a non-polar solvent such as diethyl ether.

The reaction is preferably carried out in an inert solvent such as an ether e.g. diethyl ether or tetrahydrofuran, an alkanol e.g. ethanol, an ester e.g. ethyl acetate or a halohydrocarbon e.g. methylene chloride, or mixtures thereof. The reaction is conveniently carried out in the temperature range 0°–40° more particularly at room temperature.

Quaternary ammonium salts of compounds of formula (I) wherein R contains a basic nitrogen atom may be prepared reacting a compound of formula (I) or a carboxyl protected derivate thereof with a $C_{1-4}$ alkyl halide or equivalent thereof, wherein the $C_{1-4}$ alkyl group may be optionally substituted by a carbamoyl group, followed if desired by removal of any carboxyl protecting groups.

Conveniently the reaction is carried out using the appropriate alkyl halide e.g. iodine in a solvent such as acetonitrile and optionally with heating.

Metabolically labile esters of compounds of formula(I) may be prepared by esterification of the carboxylic acid group or a salt thereof or by trans esterification using conventional procedures.

In order that the invention may be more fully understood the following examples are given by way of illustration only.

In the Preparations and Examples, unless otherwise stated:

Melting points (m.p.) were determined on a Büchi m.p. apparatus and are uncorrected. All temperatures refer to ° C.

Infrared spectra were measured in chloroform-d1 solutions on an FT-IR instrument.

Proton Magnetic Resonance ($^1$H-NMR) spectra were recorded at 300, 400 or 500 MHz as solutions in chloroform d-1, unless otherwise stated. Chemical shifts are reported in ppm.

Column chromatography was carried out over silica gel (Merck AG Darmstadt, Germany).

Solutions were dried over anhydrous sodium sulphate. "Petrol" refers to petroleum ether, b.p. 40–60° C.

Methylene chloride was redistilled over phosphorous pentoxide; tetrahydrofuran was redistilled over potassium; diethyl ether was redistilled over sodium and ethyl acetate was dried over activated molecular sieves.

The following abbreviations are used in the text: PE=petroleum ether, EE=ethyl ether, EA=ethyl acetate, CH=cyclohexane, DCM=dichloromethane, MeCN= acetonitrile, THF=tetrahydrofurane, DMF=N,N-dimethyl formamide, MeOH=methyl alcohol, NMP=1-methyl-2-pyrrolidinone, TEA=triethylamine, Dimedone=5,5-dimethyl-1,3-cyclohexane-dione, TBAF= tetrabutylammonium fluoride trihydrate (solid,unless otherwise specified), LHMDS=lithium bis(trimethylsilyl) amine, TPP=triphenylphosphine, DIPEA-HF=N,N-diisopropylethylamine trihydrofluoride, TREAT-HF= triethylamine trihydrofluoride, DBU=1,8-diazobicyclo [5.4.0undec-7-ene, DMSO=dimethylsulphoxide, TEA= Triethylamine.

"Lawesson's reagent" was obtained from Aldrich Chemical Co. and used as such.

Tlc refers to thin layer chromatography on silica plates (Merck AG Darmstadt, Germany).

When necessary, final salts were purified by preparative HPLC, using a Dynamax C18 column (25 cm×21 mm, particle size: 8 mm), a UV light detector scanning at 225 nm, and at 10 ml/min as the flow rate. Eluants are specified for each compound.

INTERMEDIATE 1

2,2-Diethoxythioacetamide

To a stirred mixture of $P_2S_5$ (45 g) in THF (300 ml) at 23°, sodium carbonate (21.5 g) was added. At the mixture, vigorously stirred, 2,2-diethoxyacetamide (10 g) was added. After 24 h a 10% aqueous solution of $Na_3PO_4$ (200 ml), EA (300 ml) and CH (300 ml) were respectively added. The aqueous layer was washed with EA and united to the organic layer. This was washed with water until clarification, dried and the solvent evaporated under reduce pressure. The crude residue was purified by flash chromatography (eluting with CH-EA 1:1) to give the title compound as a white solid (10 g).

IR: 3369, 3250–3196 ($NH_2$); 1603 (C=S) cm$^{-1}$. $^1$H-NMR: 7.86 (s); 7.54 (s); 5.05 (s); 3.76–3.64 (m); 1.27 (t).

INTERMEDIATE 2

4-(4'-Pyridyl)-2-thiazolecarboxaldehyde

A stirred mixture of 4-bromoacetylpyridine hydrobromide (6.65 g) and intermediate 1 (4.64 g) was refluxed in MeOH (80 ml) for 2 h, after which time the solvent was evaporated under reduce pressure. The crude residue was treated with a 3M aqueous sulfuric acid (60 ml) for 3 h at 23°, then sodium carbonate was added to little portions to the mixture until pH=8. The mixture was extracted with EA (3×50 ml), the organic layer was washed with brine, dried and the organic solvent evaporated under reduce pressure. The crude residue was purified by flash chromatography (eluting with CH-EA in gradient from 6:4 to 2:8) to give the title compound as a yellow-orange solid (2.57 g). M.p. 124–126°.

Tlc: CH-EA (2:8), $R_f$=0.60. IR: 1691 (C=O), 1601 (C=C, C=N) cm$^{-1}$. $^1$H-NMR: 10.07 (s); 8.73 (m); 8.11 (d); 7.83 (m).

INTERMEDIATE 3

2-Benzothiazolecarboxaldehyde

To a stirred solution of benzothiazole (3.28 ml) in anydrous THF (40 ml), at −78°, under a nitrogen atmosphere, butyllithium (2.0 ml of a 1.6M solution in hexane) was added dropwise. After 0.33 h, a solution of DMF (7 ml) in anydrous THF (20 ml) was added dropwise and the reaction mixture was allowed to rise to 0° over 1 h. The reaction was quenched by pouring the mixture into water (100 ml) and extracted with EE (2×150 ml). The organic layer was washed with brine, dried and the solvent evaporated under reduced pressure. The crude residue was purified by flash chromatography (eluting with CH-EA in gradient from 95:5 to 8:2), and crystallized from PE to give the title compound as a yellow solid (1.88 g). M.p. 76–77°

Tlc: CH-EA (1:1), $R_f$=0.80. IR: 1697 (C=O) cm$^{-1}$. $^1$H-NMR: 10.19 (s); 8.27 (m); 8.03 (m); 7.61 (m).

INTERMEDIATE 4

4-Phenyl-2-thiazolecarboxaldehyde

A stirred mixture of 2-bromoacetophenone (6.70 g) and Intermediate 1 (5.50 g) was refluxed in EtOH (100 ml) for 5 h after which time, the solvent was evapored under reduce pressure. The residue was treated with saturated sodium bicarbonate solution (100 ml) and extracted 3 times with EE (3×100 ml). Evaporation of the organic solvent under reduce pressure gave a crude residue which was dissolved in acetone (100 ml) and treated with a 1M sulfuric acid (60 ml) for 4 h, at 23°

Then sodium carbonate was added to little portions to the mixture until pH=8. The mixture was concentrated under reduced pressure to ⅓ volume and extracted with EE (3×100 ml). The organic phase was washed with brine, dried and concentrated in vacuo. The crude residue was purified by flash chromatography (eluting with CH-EA 95:5) and crystallized from PE to give the title compound as a orange solid (2.59 g). M.p. 64–66° C. Tlc: CH-EA (7:3), $R_f$=0.76. IR (nujol): 1693 (C=O) cm$^{-1}$. $^1$H-NMR: 10.09 (1H, d); 7.96 (2H, dd): 7.90 (1H, d); 7.50 (2H, m); 7.43 (1H, m).

INTERMEDIATE 5

3-(4-Pyridyl)benzaldehyde

To a stirred slurry of 4-bromopyridine hydrochloride (1.25 g) in 10 ml of water and 14 ml of toluene at 0°, was added a solution of sodium carbonate (1.56 g) in 16 ml of water. The mixture was allowed to raise at 23° then 3-fornylbenzenboronic acid (1 g) and tetrakis (triphenylphosphine)palladium were added under nitrogen atmosphere. The mixture was warmed to 85° for 8 h. After which time, the solvent was evaporated under reduce pressure, the residue treated with 10% aqueous sodium carbonate (60 ml) and extracted 3 times with DCM (3×100 ml). After evaporation of the organic solvent under reduce pressure, the crude residue was purified by flash chromatography (eluting with CH-EA in gradient from 6:4 to 1:1) to give the title -compound as a yellow-orange solid (3.17 g).

Tlc: CH-EA (2:8), $R_f$=0.43; IR: 1603 (C=C, C=N) cm$^{-1}$. $^1$H-NMR: 8.65 (m); 7.79 (m); 7.75 (s); 5.63 (s); 3.48 (s).

INTERMEDIATE 6

2,6-Lutidine N-Oxide

Sodium sulphate (6 g) and a solution of m-chloroperbenzoic acid (40 g) in DCM (140 ml) was added to a solution of 2,6-lutidine (5 ml) in dry DCM (60 ml). The mixture was stirred at 23° and under a nitrogen atmosphere for 18 h; then it was quenched with a saturated aqueous sodium bicarbonate solution (200 ml). Then a solution of potassium carbonate was added and the aqueous phase was saturated with NaCl and then it was extract with DCM (3×100 ml). The organic extract was dried and concentrated in vacuo to a yellow oil which was purified by flash chromatography (eluting in gradient from EA to EA-MeOH 9:1) to give the title compound as a yellow oil (4.7 g).

Tlc: EA-MeOH (9:1), $R_f$=0.24.

INTERMEDIATE 7

4-Hydroxymethyl-2,6-dimethylpyridine

Trimethyloxoniumtetrafluoborate (5.65 g) was added to a stirred solution of intermediate 6 (4.70 g) in dry DCM (90 ml) at 23° and under a nitrogen atmosphere for 1.5 h. Additional trimethyloxoniumtetrafluoborate (1.0 g) was then added and the solution was stirred for 1 h. The mixture was concentrated in vacuo and the crude mixture was dissolved in MeOH (100 ml) and the solution was warmed at refluxing under a nitrogen atmosphere. Then a solution of ammonium persulfate (1.75 g) in water (8 ml) was added. The mixture was stirred for 1 h, then it was quenched with aqueous NaOH 10% solution and extracted with DCM (3×50 ml). The organic extract was dried and concentrated in vacuo to give the crude title compound as a white solid (3.2 g)

Tlc: EA-MeOH (8:2), $R_f$=0.63. IR: 1612 (C=C) cm$^{-1}$. $^1$H-NMR: 7.00 (s); 4.7 (s); 2.55 (s).

INTERMEDIATE 8

2,6-Dimethyl-4-pyridinecarboxaldehyde

Pyridine (9.2 ml) was added to a solution of CrO$_3$ (5.7 g) in DCM (30 ml). The mixture, was stirred for 0.5 h at 23° under a nitrogen atmosphere and then a solution of intermediate 7 (2.60 g) in DCM (30 ml) was added. After 0.5 h EA (50 ml) was added and the mixture was filtered on fluoresil. The organic phase was concentrated in vacuo to a yellow oil which was purified by flash chromatography (eluting with EA-CH 8:2) to give the title compound as a yellow oil (1.12 g).

Tlc: EACH (8:2), $R_f$=0.66. IR: 1711 (C=O) cm$^{-1}$. $^1$H-NMR: 10.05 (s); 7.40 (s); 2.7 (s).

INTERMEDIATE 9

4-Hydroxymethyl-2-methylpyridine

Ammonium persulfate (231 g) was added to a solution of 2-methylpyridine (100 ml) in water-MeOH (350:700 ml); and then concentrated sulfuric acid (58 m,) was added. The mixture was stirred at reflux for 3 days. In this time other ammonium persulfate (20 g) and concentrated sulfuric acid (15 ml) were added. The mixture was quenched with NaOH 10% and extracted with EE (3×100 ml) and EA (3×100 ml), then the organic extracts were washed with brine (200 ml), dried and concentrated in vacuo to a yellow oil which was purified by flash chromatography (eluting with EE-EA 1:1) to give the title compound as a white solid (12.0 g).

Tlc: EA, $R_f$=0.22. IR: 1607 (C=C) cm$^{-1}$. $^1$H-NMR: 8.40 (d); 7.20 (s); 7.10 (d); 4.70 (s); 2.50 (s).

INTERMEDIATE 10

2-Methyl-4-pyridinecarboxaldehyde

4-Methylmorpholine N-oxide (5.7 g) and tetrapropylammonium perruthenate (23.43 g) were added to a solution of intermediate 9 ( 3.0 g) in DCM (100 ml) with molecoular sielves 4A, at 23°, under a nitrogen atmosphere for 0.5 h. The mixture was purified by flash chromatography (eluting with EE). The eluant was concentrated in vacuo to give a white solid (2.5 g). The solid was distilled to give the title compound as a yellow oil (1.0 g).

Tlc: EA, $R_f$=0.40.

$^1$H-NMR: 10.0 (s); 7.5 (d); 7.4 (s), 2.65 (s).

INTERMEDIATE 11

2-Chloro-4-hydroxymethylpyridine 2-chloro-4-pyridinecarboxylic acid (2.5 g) in dry THF (100 ml) was added to a stirred solution of lithium aluminum hydride (20.6 ml, solution 1M in THF), kept at 23° and under a nitrogen atmosphere. The mixture was poured onto ice and extracted with EA (3×100 ml) and the organic extracts washed with brine, dried and concentrated in vacuo to give the title compound as a yellow solid (0.98 g).

Tlc: EA, $R_f$=0.7.

IR: 1597 (C=C) cm$^{-1}$. $^1$H-NMR: 8.35 (d); 7.36 (d); 7.21 (dd); 4.75 (s).

INTERMEDIATE 12

2-Chloro-4-pyridinecarboxaldehyde

To a solution of pyrdine (3 ml) in DCM (30 ml) was added a suspension of CrO$_3$ (1.88 g). The mixture was stirred at 23° for 0.5 h and then intermediate 11 (0.9 g) in DCM (30 ml) was added. The mixture was stirred for 0.5 h then was diluted with EA and filtered through Floresil. The organic solvent was evaporated under reduced pressure and was purified by flash chromatography (eluting with CH-EA 1:1) to give the title compound as a yellow solid (0.33 g). M.p. 58–60°.

Tlc: CH-EA (1:1), $R_f$=0.69. IR: 1713 (C=O) cm$^{-1}$. $^1$H-NMR: 10.04 (s); 8.65 (d); 7.74 (s), 7.65 (d).

INTERMEDIATE 13

2-Acetylamino-4-methylpyridine

To a solution of 2-amino-4-methylpyridine (20 g) in acetic acid (80 ml) was added acetic anhydride and the resulting solution was refluxed for 3 h. The solution was concentrated in vacuo and the solid obtained was triturated with about 50 ml of water and carefully neutralised with solid sodium bicarbonate. The solid was filtered, washed with water and dried under vacuum to give the crude title compound as a white solid (20 g).

IR: 3415, 3236, 3196, 1615, 1668 cm$^{-1}$. $^1$H-NMR (CDCl3): 8.72 (bs); 8.09 (d), 8.07 (s); 6.87 (d), 2.37 (s), 2.2 (s).

INTERMEDIATE 14

2-Acetylamino-4-pyridinecarboxylic Acid

To a hot (90°) suspension of intermediate 13 in water (200 ml) was added portionwise potassium permanganate (23 g). The resulting suspension was heated for 6 h and filtered while hot. The aqueous solution was washed with EA and acidified to pH 5 with HCl (5%). The acid solution was concentrated to little volume and the solid obtained was tritutated with ethanol, filtered and dried under vacuum to give the crude title compound as a white solid (17.2 g).

IR: 3526, 3346–3128, 1697 cm$^{-1}$. $^1$H-NMR (DMSO): 10.27 (s); 8.33 (s), 8.15 (d); 7.34 (d), 2.05 (s).

INTERMEDIATE 15

2-Allyloxycarbonylamino-4-hydroxymethylpyridine

A solution of intermediate 14 (8.7 g) in NaOH 10% (50 ml) was refluxed for 1 h. The solution was acidified with HCl 10% and the obtained solid was filtered, washed with water and dried under vacuum to give a white solid. This solid was added portionwise to a stirred solution of lithium aluminum hydride (1.5 g) in dry THF (75 ml), kept at 23° and under a nitrogen atmosphere. The mixture was refluxed for 3 h and at 23° was added 10% NaOH (35 ml). To the cooled solution (0°) was then added allyl chloroformate (2.08 ml) and the resulting solution was stirred at 23° for 20 0.33 h The mixture was diluted with water (100 ml) and washed with EA The organic extracts were dried and concentrated in vacuo to an oil which was purified by flash chromatography (eluting with CH-EA in gradient from 1:1 to 1:2) to give the title compound as a white foam (0.345 g).

Tlc: EA-CH (2:1), R$_f$=0.45. IR: 3179, 1732 cm$^{-1}$. $^1$H-NMR (DMSO): 10.13 (s); 8.15 (dd), 7.81 (m); 6.96 (d), 5.95 (dd), 5.39 (t), 5.35 (dq), 5.21 (dq), 4.60 (m), 4.49 (d).

INTERMEDIATE 16

2-Allyloxncarbonylamino-4-pyridinecarboxaldehyde

To a suspension of Pyridinium Chlorochromate(0.89 g) in DCM (30 ml) was added a solution of intermediate 15 (0.54 g) in DCM (20 ml). The resulting suspension was stirred at 23° for 2 h and than filtered on silica gel pad. The organic solvent was evaporated under reduced pressure to give the crude title compound as a solid (0.37 g).

Tlc: CH-EA (1:1), R$_f$=0.8. IR: 1705, 1734 cm$^{-1}$. $^1$H-NMR (DMSO): 10.63 (s); 10.08 (s), 8.54 (d), 8.25 (s), 7.46 (d); 5.97 (m), 5.38 (d), 5.24 (d), 4.63 (m).

INTERMEDIATE 17

3-Benzothiophenecarboxaldehyde

Lithium aluminum hydride (1M solution in THF, 16 ml) was added to a solution of 3-benzothiophenecarboxylic acid (1.5 g) in dry THF (50 ml). The mixture was refluxed under nitrogen for 0.5 h, then cooled to 0°. The reaction was quenched by cautiously adding EA (50 ml), EE (25 ml) and water (3 ml). The resulting slurry was filtered over celite; the filtrate was washed with 0.1N citric acid, the aqueous phase was reextracted with EA, the combined organic extracts were washed with water, saturated sodium bicarbonate solution and brine, dried and the solvents were evaporated to give a pale yellow oil (1.4 g) which was used without any further purification. To a cooled (−70°) solution of oxalyl chloride (1.1 ml) in dry DCM (50 ml), DMSO (1.7 ml) was added dropwise, then a solution of the above crude material (1.4 g) in dry DCM (25 ml) and TEA (7.1 ml) were also added. The mixture was stirred under nitrogen until the temperature reached −30°, then the reaction was quenched by the addition of water (50 ml). The layers were separated, the aqueous phase was extracted with DCM (50 ml), the combined organic aqueous phase was extracted with DCM (50 ml), the combined organic extracts were washed with water and brine, dried and the solvents were evaporated. The crude material was purified by flash chromatography (eluting with CH-EA in gradient from 9:1 to 7:3) to give the title compound as an orange solid (1.18 g).

Tlc: CH-EA (7:3), R$_f$=0.55. $^1$H-NMR (CDCl3): 10.17 (s); 8.70 (m); 8.33 (s); 7.90 (m); 7.49 (m).

INTERMEDIATE 18

(3S,4R)-1-[(Allyloxycarbonyl)
(triphenylphosphoranylidene)methyl]-3-[(1R)-1-tert-
butyldimethylsilyloxy)ethyl]-4-[(2'R)-1'-
oxocyclohex-2'-yl]azetidin-2-one

INTERMEDIATE 19

(3S,4R)-1-[(Allyloxycarbonyl)
(triphenylphosphoranylidene)methyl]-3-[(1R)-1-
(tert-butyldimethylsilyloxy)ethyl]-4-[(6'R)-2'-
[(phenyl)hydroxymethyl]-1'-oxocyclohex-6'-yl]
azetidin-2-one A solution of intermediate 18 (2.78 g) in dry THF (20 ml) was added dropwise to a stirred solution of LHMDS (10.18 ml of a 1M solution in hexane) in dry THF (15 ml), keept at −78° and under a nitrogen atmosphere. The mixture was stirred until the temperature reached −60°, then cooled to −78°; at this point a solution of benzaldehyde (2.07 ml) in dry THF (10 ml) was added dropwise. The reaction mixture was stirred at −78° for 0.5 h, then it was quenched with a saturated aqueous solution of ammonium chloride (150 ml) and extracted with EA (3×100 ml). The organic layer was washed with brine, dried and the solvent evaporated under reduced pressure. The crude residue was purified by flash chromatography (eluting with CH-EA in gradient from 8:2 to 7:3) to give the title compound as a white foam (2.53 g).

Tlc: CH-EA (1:1), R$_f$=0.53.

Using the same general procedure described for preparing intermediate 19, the following compounds were prepared:

INTERMEDIATE 20

(3S,4R)-1-[(Allyloxycarbonyl)
(triphenylphosphoranylidene)methyl]-3-[(1R)-1-
(tert-butyldimethylsilyloxy)ethyl]-4-[(6'R)-2'-
[(pyrid-4-yl)hydroxymethyl]-1'-oxocyclohex-6'-yl]
azetidin-2-one Starting from intermediate 18 (4.0 g) and 4-pyridinecarboxaldehyde (0.68 ml the title compounds was obtained as a white foam (2.41 g).

Tlc: CH-EA (2:8), R$_f$=0.20, 0.26.

INTERMEDIATE 21

(3S,4R)-1-[(Allyloxycarbonyl)
(triphenylphosphoranylidene)methyl]-3-[(1R)-1-
(tert-butymethylsilyloxy)ethyl]-4-[(6'R)-2'-[(4-
nitrophenyl)hydroxymethyl]-1'-oxocyclohex-6'-yl]
abzetidin-2-one Starting from intermediate 18 (3.01 g) and 4-nitrobenzaldehyde (2.66 g) the title compound was obtained as a white foam (4.38 g).

Tlc: CH-EA (1:1), R$_f$=0.41.

INTERMEDIATE 22

(3S,4R)-1-[(Allyloxycarbonyl)
(triphenylphosphoranylidene)methyl]-3-[(1R)-1-
(tert-butyldimethylsilyloxy)ethyl]-4-[(6'R)-2'-[(4-
chloro-3-nitrophenyl)hydroxymethyl]-1'-
oxocyclohexe-6'-yl]azetidin-2-one Starting from intermediate 18 (2 g) and 4-chloro-3-nitrobenzaldehyde (1.4 g) the title compound was obtained as a yellow foam (1.5 g).

Tlc: CH-EA (1:1), $R_f$=0.39.

INTERMEDIATE 23

(3S,4R)-1-(Allyloxycarbonyl)
(triphenylphosphoranylidene)methyl]-3-[(1R)-1-
(tert-butyldimethylsilyloxy)ethyl]-4-[(6'R)-2-yl)
hydroxymethyl]-1'-oxocyclohex-6'-yl]azetidin-2-one Starting from intermediate 18 (3.47 g) and 2-benzothiophenecarboxaldehyde (2.05 g) the title compound was obtained as a yellow foam (2.12 g).

Tlc: CH-EA (6:4), $R_f$=0.33.

INTERMEDIATE 24

(3S,4R)-1-[[(Allyloxycarbonyl)]
(triphenylphosphoranilidene)methyl]-3-[(1R)-1-(tert-
butyldimethylsilyloxy)ethyl]-4-[(6'R)-2'-
[(benzothiophen-3-yl)hydroxymethyl]-1-
oxocyclohex-6'-yl]azetidin-2-one Starting from intermediate 18 (3.00 g) and intermediate 17 the title compound was obtained as a yellow foam (1.81 g).

Tlc: CH-EA (6:4), $R_f$=0.38.

INTERMEDIATE 25

((3S,4R)-1-[[(Allyloxycarbonyl)]
(triphenylphosphoranilidene)methyl]-3-[(1R)-1-(tert-
butyldimethylsilyloxy)ethyl]-4-[(6'R)-2'-[(4-(4'-
pyridyl)thiophen-2-yl)hydroxymethyl-1'-
oxocyclohex-6'-yl]azetidin-2-one Starting from intermediate 18 (3.00 g) and 4-(4'-pyridyl)-2-thiophenecarboxaldehyde (1.58 g) the title compound was obtained as a yellow foam (1.75 g).

INTERMEDIATE 26

(3S,4R)-1-[(Allyloxycarbonyl)
(triphenylphosphoranylidene)methyl]-3-[(1R)-1-
(tert-butyldimethylsilyloxy)ethyl]-4-[(6'R)-2'-
[(phenyl)(methanesulfonyloxy)methyl]-1'-
oxocyclohex-6'-yl]azetidin-2-one To a stirred solution of intermediate 19 (2.53 g) in dry DCM (100 ml), at 0°, under a nitrogen atmosphere, TEA (1.52 ml) and methanesulfonyl chloride (0.74 ml) were added. The reaction temperature was allowed to rise to 23° and the stirring continued for 1 h, after which time the reaction was quenched by adding a saturated aqueous ammonium chloride solution (100 ml) and EA (120 ml). The aqueous layer was extracted with EA (2×100 ml); the combined organic extracts were washed with brine (2×100 ml), dried over sodium sulphate and concentrated in vacuo. The crude residue was purified by flash chromatography (eluting with CH-EA in gradient from 65:35 to 1:1) to give the title compound as a white foam (2.12 g).

Tlc: CH-EA (1:1), $R_f$=0.49, 0.57.

Using the same general procedure described for preparing intermediate 26 the following compounds were obtained:

INTERMEDIATE 27

(3S,4R)-1-[(Allyloxycarbonyl)
(triphenylphosphoranylidene)methyl]-3-[(1R)-1-
(tert-butyldimethylsilyloxy)ethyl]-4-[(6'R)-2'-
[(pyrid-4-yl)(methanesulfonyloxy)methyl]-1'-
oxocyclohex-6'-yl]azetidin-2-one Starting from intermediate 20 (1.60 g) title compounds were obtained (70 g)

Tlc: CH-EA (2:8), $R_f$=0.46, 0.60.

INTERMEDIATE 28

(3S,4R)-1-[(Allyloxycarbonyl)
(triphenylphosphoranylidene)methyl]-3-[(1R)-1-
(tert-butyldimethylsilyloxy)ethyl]-4-[(6'R)-2'-[(4-
nitrophenyl)(methanesulfonyloxy)methyl]-1'-
oxocyclohex-6'-yl]azetidin-2-one Starting from intermediate 21 (4.08 g) in dry DCM (60 ml) the title compounds were obtained as a white foam (2.89 g).

Tlc: CH-EA (1:1), $R_f$=0.37, 0.55.

INTERMEDIATE 29

(3S,4R)-1-[(Allyloxycarbonyl)
(triphenylphosphoranylidene)methyl]-3-[(1R)-1-
(tert-butyldimethylsilyloxy)ethyl]-4-[(6'R)-2'-[(4-
chloro-3-nitrophenyl)(methanesulfonyloxy)methyl]-
1'-oxocyclohexe-6'-yl]azetidin-2-one Starting from intermediate 22 (1.5 g) the title compound was obtained as a yellow foam (0.49 g)

Tlc: CH-EA (1:1), $R_f$=0.35.

INTERMEDIATE 30

(3S,4R)-1-[(Allyloxycarbonyl)
(triphenylphosphoranylidene)methyl]-3-[(1R)-1-
(tert-butyldimethylsilyloxy)ethyl]-4-[(6'R)-2'-
[(benzothiophen-2-yl)(methanesulfonyloxy)methyl]-
1'-oxocyclohex-6'-yl]azetidin-2-one Starting from intermediate 23 (2.10 g) the title compound was obtained as a yellow glass (1.57 g).

Tlc: CH-EA (6:4), $R_f$=0.50 and 0.42.

INTERMEDIATE 31

[(3S,4R)-1-[(Allyloxycarbonyl)]
(triphenylphosphoranilidene)methyl]-3-[(1R)-1-(tert-
butyldimethylsilyloxy)ethyl]-4-[(6'R)-2'-
[(benzothiophen-3-yl)(methanesulfonyloxy)methyl]-
1'-oxocyclohex-6'-yl]azetidin-2-one Starting from intermediate 24 (1.80 g) the title compound was obtained as a yellow foam (1.74 g)

Tlc: CH-EA (6:4), $R_f$=0.42.

INTERMEDIATE 32

[(3S,4R)-1-[[(Allyloxycarbonyl)]
(trphenylphosphoranilidene)methyl]-3-[(1R)-1(tert-
butyldimethylsilyoxy)ethyl]-4-[(6'R)-2'-[(4-(4'-
pyridy)thiophen-2-yl)(methanesulfonyloxy)methyl]-
1'-oxocyclohex-6'-yl]azetidin-2-one Starting from intermediate 25 (1.74 g) the title compound was obtained as a yellow foam (1.208 g).

Tlc: DCM-acetone (75:25), $R_f$=0.45.

INTERMEDIATE 33

(3S,4R)-1-[(Allyloxycarbonyl)
(triphenylphosphoranylidene)methyl]-3-[(1R)-1-
(tert-butyldimethylsilyloxy)ethyl]-4-[(6'R)-2'-[(4-(4'-
pyridy)thiazol-2-yl)(p-toluenesulfonyloxy)methyl]-
1'-oxocyclohex-6'-yl]azetidin-2-one A solution of intermediate 18 (3.52 g) in dry THF (30 ml) was added dropwise to a stirred solution of LHMDS (11.6 ml of a 1M solution in hexane) also in dry THF (20 ml), kept at −78° and under a nitrogen atmosphere. The mixture was stirred until the temperature reached −60°, then cooled to −78°; at this point a solution of intermediate 2 (2.5 g) in dry THF (20 ml) was added dropwise. The reaction mixture was stirred until the temperature reached −60°, then it was transferred via a cannula over 0.165 h into a stirred solution of p-toluenesulfonyl chloride (2.94 g) in dry THF (35 ml), kept under a nitrogen atmosphere, at 23°. The mixture was stirred for further 0.165 h, then the reaction was quenched by pouring the mixture into a saturated sodium bicarbonate solution (150 ml). The mixture was extracted with EA (3×150 ml). The organic layer was washed with brine, dried and the solvent evaporated under reduced pressure. The crude residue was purified by flash chromatography (eluting with CH-EA in gradient from 6:4 to 2:8) to give the title compound as a yellow foam (3.04 g).

Tlc: CH-EA (2:8), $R_f$=0.48.

Using the same general procedure described for preparing intermediate 33 the following compounds were obtained:

INTERMEDIATE 34

(3S,4R)-1-[(Allyloxycarbonyl)
(triphenylphosphoranylidene)methyl]-3-[(1R)-1-
(tert-butyldimethylsilyloxy)ethyl]-4-[(6'R)-2-yl)(p-
toluenesulfonyloxy)methyl-1'-oxocyclohex-6'-yl]
azetidin-2-one Starting from intermediate 18 (2 g) and intermediate 3 (1.08 g) the title compounds were obtained as a yellow foam (2.20 g).

Tlc: CH-EA (1:1), $R_f$=0.50, 0.60.

INTERMEDIATE 35

(3S,4R)-1-[(Allyloxycarbonyl)
(triphenylphosphoranylidene)methyl]-3-[(1R)-1-
(tert-butyldimethylsilyl)ethyl]-4-[(6'R)-2'-[(4-
phenylthiazol-2-yl)(p-toluenesulfonyloxy)methyl]-
1'-oxocyclohex-6'-yl]azetidin-2-one Starting from intermediate 18 (3.60 g) and intermediate 4 the title compounds as a yellow foam (3.45 g).

Tlc: CH-EA (6:4), $R_f$=0.37–0.34.

INTERMEDIATE 36

(3S,4R)-1-[(Allyloxycarbonyl)
(triphenylphosphoranylidene)methyl]-3-[(1R)-1-
(tert-butyldimethylsilyloxy)ethyl]-4-[(6'R)-2'-[(3-(4-
pyridyl)phenyl)p-toluenesulfonyloxy)methyl]-1-'-
oxocyclohex-6'-yl]azetidin-2-one Starting from intermediate 18 (3.0 g) and intermediate 5 (2.05 g) the title compound (2.67 g) was obtained as a yellow foam Tlc: CH-EA (2:8), $R_f$=0.48.

INTERMEDIATE 37

(3S,4R)-1-[(Allyloxycarbonyl)
(triphenylphosphoranylidene)methyl]-3-[(1R)-1-
(tert-butyldimethylsilyloxy)ethyl]-4-[(6'R)-2'-[(2,6-
dimethylpyridin-4-yl)(p-toluenesulfonyloxy)
methyl]-1'-oxocyclohex-6'-yl]azetidin-2-one Starting from intermediate 18 (2.5 g) and intermediate 8 (1.0 g) a yellow oil was obtained then purified by flash chromatography (eluting with CH-EA 8:2) to give the title compounds as a yellow oil (2.63 g).

Tlc: CH-EA (2:8), $R_f$=0.4, 0.55.

INTERMEDIATE 38

(3S,4R)-1-(Allyloxycarbonyl)
(triphenylphosphoranylidene)methyl]-3-[(1R)-1-
(tert-butyldimethylsilyloxy)ethyl]-4-[(6'R)-2'-[(2-
methylpyridin-4-yl)(p-toluenesulfonyloxy)methyl]-
1'-oxocyclohex-6'-yl]azetidin-2-one Starting from intermediate 18 (2.0 g) and intermediate 10 (1.0 g) the title compound was obtained as a white foam (1.73 g).

Tlc: EA-MeOH (95:5), $R_f$=0.53.

INTERMEDIATE 39

(3S,4R)-1-[(Allyloxycarbonyl)
(triphenylphosphoranylidene)methyl]-3-[(1R)-1(tert-
butyldimethylsilyloxy)ethyl]-4-[(6'-2'-[(benzofuran-
2-yl)(p-toluenesulfonyloxy)methyl]-1'-oxocyclohex-
6'R)-yl]azetidin-2-one.

Starting from intermediate 18 (3 g) and 2-benzofurancarboxaldehyde (1.1 g) the title compound was obtained as a yellow foam (2.4 g).

Tlc: CH-EA (1:1), $R_f$=0.47.

INTERMEDIATE 40

(3S,4R)-1-(Allyloxycarbonyl)
(triphenylphosphoranylidene)methyl]-3-[(1R)-1-
(tert-butyldimethylsilyloxy)ethyl]-4-[(6'R)-2'-
[(benzofuran-2-yl)(p-toluenesulfonyloxy)methyl]-1'-
oxocyclohex-6'-yl]azetidin-2-one.

Starting from intermediate 18 (2.1 g) and intermediate 12 (0.51 g) the title compound was obtained as a yellow foam (1.57 g).

Tlc: CH-EA (1:1), $R_f$=0.33.

INTERMEDIATE 41

(3S,4R)-1-[(Allyloxycarbonyl)
(triphenylphosphoranylidene)methyl)]-3-[(1R)-1
(tert-butyldimethylsilyloxy)ethyl]-4-[(6'R)-2'-[(2-
furyl[3,2-]pyridine)(p-toluenesulfonyloxy)methyl]-
1'-oxocyclohex-6'-yl]azetidin-2-one.

Starting from intermediate 18 (1.8 g) and 2-formylfuro [3,2-c]pyridine (035 g) the title compound was obtained as a yellow foam (1.27 g).

Tlc: EA, $R_f$=0.5.

INTERMEDIATE 42

(3S,4R)-1-[(Allyloxycarbonyl)
(triphenylphosphoranylidene)methyl]-3-[(1R)-1-
(tert-butyldimethylsilyloxy)ethyl]-4-[(6'R)-2'-[(2-
(Allyloxycarbonylamino)pyrid-4-yl)(p-
toluenesulfonyloxy)methyl]-1'-oxocyclohex-6'-yl]
azetidin-2-one Starting from intermediate 18 (0.95 g) and intermediate 16 the title compound was obtained as a white foam (0.71 g).

Tlc: CH-EA (1:1), $R_f$=0.22.

INTERMEDIATE 43

(3S,4R)-1-[(Allyloxycarbonyl)
(triphenylphosphoranylidene)methyl]-3-[(1R)-1-tert-
butyldimethylsilyloxy)ethyl]-4-[(6'R)-2'-(E)-
(phenylmethylene)-1-'-oxocyclohex-6'-yl]azetidin-2-
one To a stirred solution of the intermediate 26 (2.12 g) in dry DCM (90 ml), at 23° and under a nitrogen atmosphere, in presence of activated molecular sieves, a solution of DBU (0.46 ml) in dry DCM (10 ml) was added dropwise over 0.165 h. Stirring was continued for 2 h then the reaction mixture was poured into a saturated aqueous ammonium chloride solution (100 ml) and extracted with EA (3×100 ml). The organic layer was washed with brine, dried and the solvent evaporated under reduced pressure. The crude residue was purified by flash chromatography (eluting with CH-EA in gradient from 9:1 to 7:3) to give the title compound as a white foam (1.07 g).

Tlc: CH-EA (1:1), $R_f$=0.63.

Using the same general procedure described for preparing intermediate 43 the following compounds were obtained.

INTERMEDIATE 44

(3S,4R)-1-[(Allyloxycarbonyl) (triphenylphosphoranylidene)methyl]-3-[(1R)-1-tert-butyldimethylsilyloxy)ethyl]-4-[(6'R)-2'-[(E)-(4-(4'-pyridyl)thiazol-2-yl)methylene]-1'-oxocyclohex-6'-yl]azetidin-2-one Starting from intermediate 33 (3.0 g) title compound was obtained as a yellow foam (2.58 g)

Tlc: CH-EA (2:8), $R_f$=0.50.

INTERMEDIATE 45

(3S,4R)-1-[(Allyloxycarbonyl) (triphenylphosphoranylidene)methyl]-3-[(1R)-1-(tert-butyldimethylsilyloxy)ethyl]-4-[(6'R)-2'-[(E)-(benzothiazol-2-yl)methylene]-1'-oxocyclohex-6'-yl] azetidin-2-one Starting from intermediate 34 (2.20 g) a crude title compound as a yellow foam (0.78 g)

Tlc: CH-EA (6:4), $R_f$=0.57.

INTERMEDIATE 46

(3S,4R)-1-[(Allyloxycarbonyl) (triphenylphosphoranylidene)methyl]-3-[(1R)-1-(tert-butyldimethylsilyloxy)ethyl]-4-[(6'R)-2'-[(E)-(pyrid-4-yl)methylene]-1'-oxocyclohex-6'-yl] azetidin-2-one Starting from intermediate 27 (1.44 g) the title compound was obtained as a white foam (1.07 g),. Tlc: CH-EA (2:8), $R_f$=0.46.

INTERMEDIATE 47

(3S,4R)-1-[(Allyloxycarbonyl) (triphenylphosphoranylidene)methyl]-3-[(1R)-1-(tert-butyldimethylsilyloxy)ethyl]-4-[(6'R)-2'-[(E)-(4-nitrophenyl)methylene]-1'-oxocyclohex-6'-yl] azetidin-2-one Starting from intermediate 28 (2.89 g) the title compound was obtained as a white foam (0.98 g),.

Tlc: CH-EA (1:1), $R_f$=0.51.

INTERMEDIATE 48

(3S,4R)-1-[(Allyloxycarbonyl) (triphenylphosphoranylidene)methyl]-3-[(1R)-1-(tert-butyldimethylsilyloxy)ethyl]-4-[(6'R)-2'-[(E)-(4-phenylthiazol-2-yl)methylene]-1'-oxocyclohex-6'-yl]azetidin-2-one Starting from intermediate 35 (3.45 g) in dry DCM (1 50 ml) the title compound was obtained as a yellow foam (1.65 g).

Tlc: CH-EA (6:4), $R_f$=0.37.

INTERMEDIATE 49

[(3S,4R)-1-[[(Allyloxycarbonyl)] (triphenylphosphoranilidene)methyl]-3-[(1R)-1-(tert-butyldimethylsilyloxy)ethyl]-4-[(6'R)-2'-[(E)-(4-(4'-pyridyl)thiophen-2-yl)methylene]-1'-oxocyclohex-6'-yl]azetidin-2-one Starting from intermediate 32 (1.2 g) the crude title compound was obtained as a yellow foam (1.18 g).

Tlc: DCM-acetone (75:25), $R_f$=0.45.

INTERMEDIATE 50

(3S,4R)-1-[(Allyloxycarbonyl) (triphenylphosphoranylidene)methyl]-3-[(1R)-1-(tert-butyldimethylsilyl)ethyl]-4-[(6'R)-2'-[(E)-(3-(4'-pyridyl)phenyl)methylene]-1'-oxocyclohex-6'-yl] azetidin-2-one Starting from intermediate 36 (2.67 g) the title compound was obtained as a yellow foam (2.21 g) which was used in the following step without any further purification. Tlc: CH-EA (2:8), $R_f$=0.50.

INTERMEDIATE 51

(3S,4R)-1-[(Allyloxycarbonyl) (triphenylphosphoranylidene)methyl]-3-[(1R)-1-(tert-butyldimethylsilyloxy)ethyl]-4-[(6'R)-2'-[(E)-(2,6-dimethylpyridin-4-yl)methylene]-1'-oxocyclohex-6'-yl]azetidin-2-one Starting from intermediate 37 (2.6 g) the title compound was obtained a yellow oil (1.38 g) Tlc: CH-EA (2:8), $R_f$=0.38.

INTERMEDIATE 52

(3S,4R)-1-[(Allyloxycarbonyl) (triphenylphosphoranylidene)methyl]-3-[(1R)-1-(tert-butyldimethylsilyloxy)ethyl]-4-[(6'R)-2'-[(E)-(2-methylpyridin-4-yl)methylene]-1'-oxocyclohex-6'-yl]azetidin-2-one Starting from intermediate 38 (1.64 g) the title compound was obtained as a crude mixture (yellow oil, 1.7 g)

Tlc: EA-MeOH (95:5), $R_f$=0.67.

INTERMEDIATE 53

(3S,4R)-1-[(Allyloxycarbonyl) (triphenylphosphoranylidene)methyl)]-3-[(1R)-1 (tert-butyldimethylsilyloxy)ethyl]-4-[(6'R)-2'-[(E)-(benzofuran-2-)methylene]-1'-oxocyclohex-6'-yl] azetidin-2-one Starting from intermediate 39 (2.4 g) the crude title compound . . .

Tlc: CH-EA (65:35), $R_f$=0.48.

INTERMEDIATE 54

(3S,4R)-1-[(Allyloxycarbonyl) (triphenylphosphoranylidene)methyl)]-3-[(1R)-1-(tert-butyldimethylsilyloxy)ethyl]-4-[(6'R)-2'-[(E)-(2-chloropyrid-4-yl)methylene]-1-oxocyclohex-6'-yl]azetidin-2-one Starting from intermediate 40 (1.57 g) the title compound was obtained as a yellow foam (1.06 g).

Tlc: CH-EA (1:1), $R_f$=0.51.

INTERMEDIATE 55

(3S4R)-1-[(Allyloxycarbonyl)
(triphenylphosphoranylidene)methyl)]-3-[(1R)-1-
(tert-butyldimethylsilyloxy)ethyl]-4-[(6'R)-2'-[(E)-
(2-furyl[3,2-c]pyridine)methylene]-1'-oxocyclohex-
6'-yl]azetidin-2-one Starting from intermediate 41 (1.27 g) the title compound was obtained as a yellow foam (0.54 g).

Tlc: EA, $R_f$=0.32.

INTERMEDIATE 56

(3S,4R)-1-[(Allyloxycarbonyl)
(triphenylphosphoranylidene)methyl]-3-[(1R)-1-
(tert-butyldimethysilyloxy)ethyl]-4-[(6'R)-2'-[(E)-(2-
(allyloxycarbonylamino)pyrid-4-yl)methylene]-1'-
oxocyclohex-6'-yl]azetidin-2-one Starting from intermediate 42 (0.62 g) title compound was obtained as a yellow foam (0.33 g).

Tlc: CH-EA (4:6), $R_f$=0.58.

INTERMEDIATE 57

(3S,4R)-1-[(Allyloxycarbonyl)
(triphenylphosphoranylidene)methyl]-3-[(1R)-1-
(tert-butyldimethylsilyloxy)ethyl]-4-[(6'R)-2'-[(E)-
(4-chloro-3-nitrophenyl)methylene]-1'-
oxocyclohexe-6'-yl]azetidin-2-one Starting from intermediate 29 (0.49 g) the title compound was obtained as a yellow foam (0.49 g).

Tlc: CH-EA (1:1), $R_f$=0.41.

INTERMEDIATE 58

(3S,4R)-1-[(Allyloxycarbonyl)
(triphenylphosphoranylidene)methyl]-3-[(1R)-1-
(tert-butyldimethylsilyloxy)ethyl]-4-[(6'R)-2'-[(E)-
(benzothiophen-2-yl)methylene]-1'-oxocyclohex-6'-
yl]azetidin-2-one Starting from intermediate 30 (1.55 g) the title compound was obtained as a yellow foam (1.07 g).

Tlc: CH-EA (6:4), $R_f$=0.40.

INTERMEDIATE 59

[(3S,4R)-1-[[(Allyloxycarbonyl)]
(triphenylphosphoranilidene)methyl]-3-[(1R)-1-(tert-
butyldimethylsilyloxy)ethyl]-4-[(6'R)-2'-[(E)-
(benzothiophen-3-yl)methylene]-1'-oxocyclohex-6'-
yl]azetidin-2-one Starting from intermediate 31 (1.7 g) the title compound was obtained as a yellow foam (1.09 g).

Tlc: CH-EA (6:4), $R_f$=0.30.

INTERMEDIATE 60

Allyl (8S,9R,10S,12R)-1-aza-10-[1-(tert-
butyldimethylsilyloxy)ethyl]-11-oxo-4-[(E)-
phenylmethylene]-tricyclo-[7,2,0,0$^{38}$]-undec-2-ene-
2-carboxylate A solution of intermediate 43 (1.07 g) in dry toluene (40 ml), under a nitrogen atmosphere, was warmed to 100° and stirred for 3 h, after which time the organic solvent was evaporated under reduced pressure. The crude residue was purified by flash chromatography (eluting with CH-EA in gradient from 9:1 to 8:2) to give the title compound as a white foam (0.60 g).

Tlc: CH-EA (7:3), $R_f$=0.72. IR: 1782(C=O), 1726 (C=O), 1601 cm$^{-1}$. $^1$H-NMR: 7.38–7.28 (m); 7.26–7.20 (m); 6.49 (s); 5.83 (m); 5.32 (dd); 5.14 (dd); 4.74–4.60 (m); 4.25 (m); 4.20 (dd); 3.27 (dd); 3.03 (m); 2.2–2.1 (m); 2.0–1.9 (m); 1.7–1.5 (m); 1.25 (d); 0.88 (s); 0.08 (s).

Using the same general procedure for preparing intermediate 60, the following compounds were obtained:

INTERMEDIATE 61

Allyl (8S,9R,10S,12R)-1-Aza-10-[1-(tert-
butyldimethylsilyloxy)ethyl]-11-oxo-4-[(E)-(4-(4'-
pyridyl)thiazol-2-yl)methylene]-tricyclo-[7,2,0,0$^{3.8}$]-
undec-2-ene-2-carboxylate Starting from intermediate 44 (2.58 g) the title compound was obtained as a yellow foam (0.89 g).

Tlc: CH-EA (2:8), $R_f$=0.58. IR: 1776(C=O), 1722 (C=O), 1601 (C=C, C=N) cm$^{-1}$. $^1$H-NMR: 8.68 (m); 7.80 (m); 7.68 (s); 6.66 (d); 5.89 (m); 5.36 (m); 5.17 (m); 4.8 (m); 4.65 (m); 4.28 (dd); 4.26 (m); 4.02 (m); 3.33 (dd); 3.12 (m); 2.26 (m); 2.13 (m); 1.97 (m); 1.8–1.6 (m); 1.24 (d); 0.91 (s); 0.10 (s); 0.09 (s).

INTERMEDIATE 62

Allyl (8S,9R,10S,12R)-1-Aza-10-[1-(tert-
butyldimethylsilyloxy)ethyl]-11-oxo-4-[(E)-
(benzothiazol-2-yl)methylene]-tricyclo[7,2,0,0$^{3.8}$]-
undec-2-ene-2-carboxylate Starting from intermediate 45 (0.78 g) the title compound was obtained as a yellow foam (0.27 g).

Tlc: CH-EA (3:7), $R_f$=0.67. IR: 1778(C=O), 1720 (C=O) cm$^{-1}$. $^1$H-NMR: 8.02 (d); 7.88 (d); 7.48 (m); 7.38 (m); 6.70 (d); 5.86 (m); 5.33 (m); 5.14 (m); 4.75 (m); 4.64 (m); 4.29 (dd); 4.23 (m); 3.99 (m); 3.33 (m); 3.15 (m); 2.27 (m); 2.13 (m); 1.98 (m); 1.75 (m); 1.69 (m); 1.26 (d); 0.91 (s); 0.10 (s); 0.098 (s).

INTERMEDIATE 63

Allyl (8S,9R,10S,12R)-1-Aza-10-[1-(tert-
butyldimethylsilyloxy)ethyl]-11-oxo-4-[(E)-(pyrid-
4-yl)methylene]-tricyclo-7,2,0,0$^{3.8}$]-undec-2-ene-2-
carboxylate Starting from intermediate 46 (1.07 g) the title compound was obtained as a white foam (0.49 g).

Tlc: CH-EA (8:2), $R_f$=0.57. IR: 1776 (C=O), 1722 (C=O), 1597 (C=C) cm$^{-1}$. $^1$H-NMR: 8.55 (d); 7.12 (d); 6.41 (d); 5.82–5.78 (m); 5.33 (m); 5.16 (m); 4.76–4.58 (m); 4.26 (dd); 4.23 (m); 3.29 (dd); 3.14–2.94 (m); 2.18 (m); 2.14–1.9 (m); 1.70–1.54 (m); 1.24 (d); 0.89 (s); 0.085 (s); 0.081 (s).

INTERMEDIATE 64

Allyl (8S,9R,10S,12R)-1-aza-10-[1-(tert-
butyldimethylsilyloxy)ethyl]-11-oxo-4-[(E)-(4-
nitrophenyl)methylene]-tricyclo-[7,2,0,0$^{3.8}$]-undec-
2-ene-2-carboxylate Starting from intermediate 47 (0.98 g) the crude title compound was obtained as a white foam (0.49 g).

Tlc: CH-EA (75:25), $R_f$=0.87. $^1$H-NMR: 8.18 (d); 7.39 (d); 6.55 (d); 5.82 (m); 5.4–5.1 (m); 4.65 (m); 4.29 (dd); 4.28 (m); 3.30 (dd); 3.05 (m); 2.95 (m); 2.4–1.4 (m); 1.23 (d); 0.89 (s); 0.08 (s).

INTERMEDIATE 65

Allyl (8S,9R,10S,12R)-1-Aza-10-[1-(tert-butyldimethylsilyloxy)ethyl-11-oxo-4-[(E)-(4-phenylthiazol-2-yl)methylene]-tricyclo-[7,2,0,0$^{3.8}$]-undec-2-ene-2-carboxylate Starting from intermediate 48 (1.65 g) the title compound was obtained as a yellow foam (0.82 g).

Tlc: CH-EA (1:1), $R_f$=79. IR (CDCl$_3$): 1776 (C=O), 1720 (C=O) cm$^{-1}$. $^1$H-NMR: 7.91 (2H, m); 7.45 (1H, s); 7.43–7.35 (3H, m); 6.64 (1H, d); 5.87 (1H, m); 5.38–5.14 (2H, m); 4.8–4.58 (2H, m); 4.27 (1H, dd); 4.23–4.04 (2H, m); 4.26 (m); 3.31 (1H, dd); 3.11 (1H, m); 2.22 (1H, m); 2.16–1.90 (2H, m); 1.70 (2H, m); 1.24 (3H, m); 0.89 (9H, s); 0.09 (6H, s).

INTERMEDIATE 66

Allyl (8S,9R,10S,12R)-1-Aza-10-[1-tert-butyldimethylsilyloxy)ethyl]-11-oxo-4-[(E)-(3-(4'-pyridyl)phenyl)methylene]-tricyclo-[7,2,0,0$^{3.8}$]-undec-2-ene-2-carboxylate Starting from intermediate 50 (2.21 g) the title compound was obtained as a white foam (0.66 g).

Tlc: CH-EA (2:8), $R_f$=0.58. IR: 1776(C=O), 1722 (C=O), 1601 (C=C, C=N) cm$^{-1}$. $^1$H-NMR: 8.68 (m); 7.80 (m); 7.68 (s); 6.66 (d); 5.89 (m); 5.36 (m); 5.17 (m); 4.8 (m); 4.65 (m); 4.28 (dd); 4.26 (m); 4.02 (m); 3.33 (dd); 3.12 (m); 2.26 (m); 2.13 (m); 1.97 (m); 1.8–1.6 (m); 1.24 (d); 0.91 (s); 0.10 (s); 0.09 (s).

INTERMEDIATE 67

Allyl (8S,9R,10S,12R)-1-aza-10-[1-(tert-butyldimethylsilyloxy)ethyl]-11-oxo-4-[(E)-(2,6-dimethylpyridin-4-yl)methylene]-tricyclo-[7,2,0, 0$^{3.8}$]-undec-2-ene-2-carboxylate Starting from intermediate 51 (1.38 g) the title compound was obtained as a yellow oil (0.65 g).

Tlc: CH-EA (2:8), $R_f$=0.56. IR: 1784 and 1724 (C=O) cm$^{-1}$. $^1$H-NMR: 6.80 (s); 635 (d); 5.97 (m); 5.34 (m); 5.18(m); 4.68 (m); 4.25 (dd); 4.22 (m); 3.28 (dd); 3.04 (m); 2.96 (m); 2.51 (s); 2.15 (m); 2.02–1.9(m); 1.6; 1.24 (d); 0.89 (s); 0.085 (s); 0.080 (s).

INTERMEDIATE 68

Allyl (8S,9R,10S,12R)-1-Aza-10-[1-(tert-butyldimethylsilyloxy)ethyl]-11-oxo-4-[(E)-(2-methylpyridin-4-yl)methylene]-tricyclo-7,2,0,0$^{3.8}$]-undec-2-ene-2-carboxylate Starting from intermediate 52 (1.7 g) the title compound was obtained as a yellow foam (0.69 g).

Tlc: CH-EA 2:8, $R_f$=0.50. IR: 1776 and 1717 (C=O) cm$^{-1}$. $^1$H-NMR: 8.44 (d); 6.99 (s); 6.94 (d); 6.37 (d); 5.84 (m); 5.38–5.14 (m); 4.80–4.60 (m); 4 25 (dd); 4.23 (m); 3.28 (dd); 3.05 (m); 2.97 (m); 2.54 (s); 2.16 (m); 1.95 (m); 1.80–1.50 (m); 1.24 (d); 0.88 (s); 0.08 (2s).

INTERMEDIATE 69

Allyl (8S,9R,10S,12R)-1-Aza-10-[1-(tert-butyldimethylsilyloxy)ethyl]-11-oxo-4-[(E)-[(benzofuran-2-yl)methylene]-triciclo-[7,2,0,0$^{3.8}$]-undec-2-ene-carboxylate Starting from intermediate 53 the title compound was obtained as a yellow solid (0.998 g).

Tlc: CH-EA (1:1), $R_f$=0.83. IR: 1774 and 1718 (C=O) cm$^{-1}$. $^1$H-NMR: 7.53 (d); 7.45 (d); 7.27 (m); 7.21 (m); 6.65 (s); 6.38 (d); 5.87 (m); 5.38–5.14 (m); 4.84.60 (m); 4.27 (dd); 4.24 (m); 3.65 (m); 3.31 (dd); 3.09 (m); 2.26 (m); 2.08 (m); 1.96 (m); 1.67 (m); 1.26 (d); 0.90 (s); 0.10 (s).

INTERMEDIATE 70

Allyl (8S,9R,10S,12R)-1-Aza-10-[1-(tert-butyldimethylsilyloxy)ethyl]-11-oxo-4-[(E)-[(2-chloropyrid-4-yl)methylene]-triciclo-[7,2,0,0$^{3.8}$-undec-2-ene-carboxylate Starting from intermediate 54 (1.06 g) the title compound was obtained as a yellow solid (0.41 g).

Tlc: CH-EA (1:1), $R_f$=0.74. IR: 1778 and 1726 (C=O) cm$^{-1}$. $^1$H-NMR: 8.33 (d); 7.17 (d); 7.05 (dd); 6.36 (d); 5.9–5.8 (m); 5.4–5.2 (m); 4.75–4.6 (m); 4.26 (dd); 4.23 (m); 3.29 (dd); 3.06 (m); 2.92 (m); 2.17 (m); 2.02 (m); 1.94 (m); 1.65–1.55 (m); 1.24 (d); 0.88 (s); 0.081(s).

INTERMEDIATE 71

Allyl (8S,9R,10S,12R)-1-Aza-10-[1-(tert-butyldimethylsilyloxy)ethyl]-11-oxo-4-[(E)-[(2-furyl [3,2-c]pyridine)methylene]-triciclo-[7,2,0,0$^{3.8}$]-undec-2-ene-carboxylate Starting from intermediate 55 (0.54 g) the title compound was obtained as a yellow solid (0.170 g).

Tlc: EA, $R_f$=0.48. IR: 1776 and 1722 (C=O) cm$^{-1}$. $^1$H-NMR: 8.87 (s); 8.47(d); 7.39 (d); 6.70 (s); 6.40 (d); 5.88 (m); 5.40–5.14 (m); 4.804.60 (m); 4.26 (m); 3.57 (m); 3.32 (dd); 3.10 (m); 2.28 (m); 2.16–1.92 (m); 1.80–1.54 (m); 1.26 (d); 0.91 (s); 0.1 (s).

INTERMEDIATE 72

Allyl (8S,9R,10S,12R)-1-Aza-10-[1-(tert-butyldimethylsilyloxy)ethyl]-11-oxo-4-[(E)-(2-(allyloxycarbonylaminoc)pyrid-4-yl)methylene]-triciclo-[7,2,0,0$^{3.8}$]-undec-2-ene-carboxylate Starting from intermediate 56 (0.33 g) the title compound was obtained as a yellow oil (0.165 g).

Tlc: CH-EA (1:1), $R_f$=0.8. IR: 1778 and 1724 (C=O) 1597 (C=C) cm$^{-1}$. $^1$H-NMR: 6.76 (s); 6.50 (s); 6.3 (d), 5.86 (ddt); 5.35 (d), 5.2 (d); 4.71 (m); 4.63 (m), 4.25 (dd); 4.22 (m); 3.93 (s); 3.28 (dd); 3.04 (m), 2.93 (m), 2.13 (m); 2.0 (m); 2.2 (m); 1.92 (m); 1.1–1.2 (m); 1.24 (d); 0.88 (s); 0.08 (s).

INTERMEDIATE 73

Allyl (8S,9R,10S,12R)-1-Aza-10-[1-(tert-butyldimethylsilyloxy)ethyl]-11-oxo-4-[(E)-(4-chloro-3-nitrophenyl)methylene]-tricyclo-]7,2,0, 0$^{3.8}$]-undec-2-ene-2-carboxylate Starting from intermediate 57 (0.49 g) the title compound was obtained as a yellow solid (0. 150 g).

Tlc: CH-EA (8:2), $R_f$=0.84. IR: 1774 and 1778,1720, (C=O); 1535 (NO$_2$) cm$^{-1}$. $^1$H-NMR: 7.72 (d); 7.49 (d); 7.36 (dd); 6.43 (d); 5.85 (m); 5.4–5.16 (m); 4.75–4.58 (m); 4.26 (dd); 4.22 (m); 3.29 (dd); 3.05 (m); 2.86 (m); 2.2–1.9 (m); 1.6 (m); 1.23 (d); 0.88 (s); 0.08 (s). IR: 1776, 1720 (C=O); 1612(C=C) cm$^{-1}$. $^1$H-NMR: 8.50 (d); 8.46 (dd) 7.53 (m); 7.26 (dd); 6.44 (d); 5.84 (m); 5.4–5.1 (m); 4.8–4.55 (m); 4.25 (dd); 4.22 (m); 3.28 (dd); 3.05 (m); 2.93 (m); 2.18 (m); 2.0–1.8 (m); 1.8–1.5 (m); 1.23 (d); 0.88 (s); 0.08 (s).

INTERMEDIATE 74

Allyl (8S,9R,10S,12R)-1-Aza-10-[1-(tert-butyldimethylsilyloxy)ethyl]-11-oxo-4-[(E)-(benzothiophen-2-yl)methylene]-tricyclo-[7,2,0,0$^{3,8}$]-undec-2-ene-2-carboxylate Starting from intermediate 58 (1.04 g) the title compound was obtained as a yellow solid (0.624 g).

Tlc: CH-EA 75:25, R$_f$=0.67. IR: 1776 and 1610 (C=O); 1709 (C=C) cm$^{-1}$. $^1$H-NMR: 7.78 (d); 7.72 (d); 7.40–7.27 (m); 7.20 (s); 6.67 (m); 5.87 (m); 5.33 (m); 5.14 (m); 4.80–4.60 (m); 4.27 (dd); 4.25 (m); 3.38 (bd); 3.30 (dd); 3.08 (m); 2.24 (m); 2.08 (m); 1.96(m); 1.68 (m); 1.25 (d); 0.90 (s); 0.099 (s); 0.094 (s).

INTERMEDIATE 75

Allyl (8S,9R,10S,12R)-1-Aza-10-[1-(tert-butyldimethylsilyloxyethyl)-11-oxo-4-[(E)-(benzothiophen-3-yl)methylene]-tricyclo-[7,2,0, 0$^{3,8}$]-undec-2-ene-2-carboxylate Starting from intermediate 59 (1.04 g) the title compound was obtained as a yellow foam (0.535 g).

Tlc: CH-EA (75:25), R$_f$=0.69. IR: 1780 and 1722 (C=O) cm$^{-1}$. $^1$H-NMR: 7.86 (m); 7.45 (m); 7.38 (m); 7.29 (d); 6.63 (d); 5.85 (m); 5.32 (m); 5.13 (m); 4.75–4.60 (m); 4.28 (dd); 4.28 (m); 3.30 (dd); 3.09 (m); 2.29 (m); 2.19 (m); 2.0–1.9 (m); 1.7–1.5 (m); 1.25 (d); 0.90 (s); 0.098 (s); 0.089 (s).

INTERMEDIATE 76

Allyl (8S,9R,10S,12R)-1-Aza-10-[1-(tert-butyldimethylsilyloxy)ethyl-11-oxo4-[(E)-(4-(4'-pyridyl)thiophen-2-yl)methylene]-tricyclo-[7,2,0, 0$^{3,8}$]-undec-2-ene-2-carboxylate Starting from intermediate 49 (1.17 g) the title compound was obtained as a yellow foam (0.485 g).

Tlc: DCM-acetone 75:25, R$_f$=0.77. IR: 3385, 1772 and 1717 (C=O) cm$^{-1}$. $^1$H-NMR: 8.61 (dd) 7.58 (d); 7.45 (dd); 7.29 (m); 6.64 (d); 5.88 (m); 5.35 (m); 5.16 (m); 4.74 (m); 4.63 (m); 4.25 (dd); 4.23 (m); 3.28 (dd); 3.25 (m); 3.05 (m); 2.22 (m); 2.07 (m); 1.95 (m); 1.6–1.7 (m); 1.24 (m); 0.89 (s); 0.09 (s); 0.08 (s).

INTERMEDIATE 77

Allyl (8S,9R,10S,12R)-1-Aza-10-(1-hydroxyethyl)-11-oxo-4-[(E)phenylmethylene]-tricyclo-[7,2,0,0$^{3,8}$]-undec-2-ene-2-carboxylate To a stirred solution of intermediate 60 (0.60 g) in dry THF (50 ml) at 23°, under a nitrogen atmosphere, glacial acetic acid (0.40 ml) and TBAF (6.1 ml of a solution 1M in THF) were added. After 24 h the reaction mixture was quenched adding a saturated aqueous sodium bicarbonate solution (100 ml) and EA (80 ml). The mixture was extracted with EA (2×100 ml) and the organic layer was washed with brine, dried and the solvent evaporated under reduced pressure. The crude residue was purified by flash chromatography (eluting with CH-EA in gradient from 1:1 to 1:9) to give the title compound as a white solid (0.25 g).

Tlc: CH-EA (2–8), R$_f$=0.70. IR: 1774 (C=O), 1720 (C=O) cm$^{-1}$. $^1$H-NMR: 7.4–7.2 (m); 6.51 (m); 5.9–5.8 (m); 5.32 (dd); 5.14 (dd); 4.76–4.60 (m); 4.32 (m); 4.22 (dd); 3.32 (dd); 3.14–3.0 (m); 2.2–1.5 (m); 1.33 (d).

Using the same general procedure described for preparing intermediate 77, the following compounds were prepared:

INTERMEDIATE 78

Allyl (8S,9R,10S,12R)-1-aza-10-(1-hydroxyethyl)-11-oxo-4-[(E)-(4-nitrophenyl)methylene]-tricyclo-∂7,2,0,0$^{3,8}$]-undec-2-ene-2-carboxylate Starting from intermediate 64 (0.25 g) the title compound was obtained as a white solid (0.11 g).

Tlc: CH-EA (0:1), R$_f$=0.62. IR: 1778(C=O), 1720 (C=O) cm$^-$. $^1$H-NMR: 8.20 (m); 7.39 (m); 6.55 (d); 5.86 (m); 5.36–5.14 (m); 4.78–4.60 (m); 4.31 (dd); 4.26 (m); 3.35 (dd); 3.11 (m); 2.95 (m); 2.21 (m); 1.99 (m); 1.80–1.46 (m); 1.34 (d).

INTERMEDIATE 78A

Ally (8S,9R,10S,12R)-1-aza-10-(1-Hydroxyethyl)-11-oxo-4-[(E)-(pyrid-4-yl)methylene]-tricyclo-[7,2, 0,0$^{3,8}$]-undec-2-ene-2-carboxylate Starting from intermediate 63 (0.49 g) the title compound was obtained as a white solid (0.17 g).

Tlc: CH-EA (1:9), R$_f$=0.25. $^1$H-NMR: 8.55 (dd); 7.13 (dd); 6.42 (m); 5.92–5.78 (m); 5.36–5.28 (m); 5.20–5.13 (m); 4.78–4.58 (m); 4.29 (dd); 4.26 (m); 3.33 (dd); 3.16–3.04 (m); 3.02–2.92 (m); 2.24–210 (m); 2.04–1.94 (m); 1.80–1.52 (m); 1.33 (d).

INTERMEDIATE 79

Allyl (8S,9R,10S,12R)-1-aza-10-(1-Hydroxyethyl)-11-oxo-4-[(E)-(2-methylpyridin-4-yl)methylene]-tricyclo-[7,2,0,0$^{3,8}$]-undec-2-ene-2-carboxylate Glacial acetic acid (1.2 ml) and TBAF (6.0 g) were added to solution of intermediate 68 (0.685 g.) in dry THF (15 ml). The mixture was stirred at 23°, under a nitrogen atmosphere, for 15 h. The mixture was diluted with a saturated sodium bicarbonate solution (200 ml), extracted with EA (3×150 ml) and the organic layer was washed with brine (100 ml), dried and concentrated in vacuo, then was purified by flash chromatography (eluting with EA-Aceton 9:1) to give the title compound as a yellow foam (0.270 g).

IR: 3396 (OH); 1772 and 1717 (C=O) cm$^{-1}$. $^1$H-NMR: 8.44 (d); 7.00 (s); 6.95 (d); 6.40 (d); 5.86 (m); 5.40–5.14 (m); 4.80–4.58 (m); 4 29 (dd); 4.27 (m); 3.34 (dd); 3.09 (m); 2.98 (m); 2.55 (s); 2.16 (m); 1.98 (m); 1.80–1.48 (m); 1.34 (d).

Using the same general procedure described for preparing intermediate 79 the following compounds were prepared:

INTERMEDIATE 80

Allyl (8S,9R,10S,12R)-1-aza-10-(1-Hydroxyethyl)-11-oxo-4-[(E)-[(2-chloropyrid-4-yl)methylene]-tricyclo-[7,2,0,0$^{3,8}$]-undec-2-ene-2-carboxylate Starting from intermediate 70 (0.37 g.) the title compound was obtained as a yellowish glass (0.20 g).

Tlc: CH-EA (1:1); R$_f$=0.27. $^1$H-NMR: 8.34 (d); 7.18 (s); 7.06 (dd); 6.38 (d); 5.87 (m); 5.34 (m); 5.2 (m); 4.8–4.6 (m); 4.30 (dd); 4.26 (m); 3.34 (dd); 3.10 (m); 2.94 (m); 2.19 (m); 2.06–1.86 (m); 1.69 (d); 1.65–1.5 (m); 1.34 (d).

INTERMEDIATE 81

Allyl (8S,9R,10S,12R)-1-aza-10-(1-Hydroxyethyl)-11-oxo-4-[(E)-(2-furyl[3,2-c]pyridine)methylene]-tricyclo-[7,2,0,0$^{3,8}$]-undec-2-ene-2-carboxylate Starting from intermediate 71 (0.17 g.) title compound was obtained as a yellowish glass (0.085 g).

Tlc: EA; $R_f$=0.18. IR: 1776 and 1718 (C=O) cm$^{-1}$. $^1$H-NMR: 8.86 (d); 8.46 (d); 7.38 (dd); 6.69 (s); 6.40 (d); 5.88 (m); 5.38–5.14 (m); 4.80–4.60 (m); 4.30 (dd); 4.27 (m); 3.58 (m); 3.35 (dd); 3.13 (m); 2.28 (m); 2.16–1.98 (m); 1.80–1.5 (m); 1.34 (d).

INTERMEDIATE 82

Allyl (8S,9R,10S,12R)-1-aza-10-(1-Hydroxyethyl)-11-oxo-4-[(E)-(2-(allyloxycarbonylamino)pyrid-4-yl)methylene)]-tricyclo-[7,2,0,0$^{3.8}$]-undec-2-ene-2-carboxylate Starting from intermediate 72 (0.164 g) the title compound was obtained as a foam (0.112 g).

Tlc: EA, $R_f$=0.8. IR: 3810, 1827, 1776, 1724. $^1$H-NMR-CDCl3: 8.21 (d), 7.93 (m), 7.88 (s); 6.86 (dd), 6.44, (d), 5.8–6.0 (m); 5.38–5.18 (m); 4.8–4.6 (m); 4.3 (dd); 4.28 (m); 3.36 (dd); 3.16 (m); 3.04 (m), 2.21 (m); 1.95–2.01 (m); 78 (m); 1.3–1.7 (m), 1.34 (d).

INTERMEDIATE 83

Allyl (8S,9R,10S,12R)-1-aza-10-(1-Hydroxyethyl)-11-oxo-4-[(E)-(2,6-dimethylpyridin-4-yl)methylene]-tricyclo-[7,2,0,0$^{3.8}$]-undec-2-ene-2-carboxylate Glacial acetic acid (1.05 ml) and TBAF (5.4 g) were added to a stirred solution of Intermediate 67 (0.640 g) in dry THF (13 ml). The mixture was warmed at 40°, under a nitrogen atmosphere, for 1.5 h. The mixture was diluted with a saturated aqueous sodium bicarbonate solution (50 ml) and EA (50 ml) and brine (2×50 ml), dried and concentrated in vacuo. The crude material was purified by flash chromatography (eluting with CH-EA in gradient from 2:8 to EA) to give the title compound as a yellow foam (0.270 g).

Tlc: CH-EA (2:8), $R_f$=0.18. IR: 1784 and 1724(C=O) cm$^{-1}$. $^1$H-NMR: 6.81 (s); 6.37 (d); 5.87 (m); 5.38–5.16 (m); 4.78–4.60 (m); 4.29 (dd); 4.26 (m); 3.33 (dd); 3.08 (m); 2.96 (m); 2.51 (s); 2.15 (m); 1.98 (m); 1.72–1.40 (m); 1.34 (d).

Using the general procedure described for preparing the Intermediate 83 the following compounds were prepared:

INTERMEDIATE 84

Allyl (8S,9R,10S,12R)-1-aza-10-(1-Hydroxyethyl)-11-oxo-4-[(E)-[(benzofuran-2-yl)methylene]-tricyclo-[7,2,0,0$^{3.8}$]-undec-2-ene-carboxylate Starting from Intermediate 69 (0.998 g.) the title compound was obtained as a yellowish glass (0.070 g).

Tlc: CH-EA (1:1), $R_f$=0.38. IR: 1774 and 1718 (C=O) cm$^{-1}$. $^1$H-NMR: 7.52 (m); 7.44 (m); 7.32–7.18 (m); 6.65 (s); 6.38 (d); 5.87 (m); 5.38–5.12 (m); 4.82–4.58 (m); 4.29 (dd); 4.27 (m); 3.65 (m); 3.35 (dd); 3.11 (m); 2.25 (m); 2.14–1.94 (m); 1.80–1.60 (m); 1.34 (d).

INTERMEDIATE 85

Allyl (8S,9R,10S,12R)-1-aza-10-(1-Hydroxyethyl)-11-oxo-4-[(E)-(benzothiophen-2-yl)methylene]-tricyclo-[7,2,0,0$^{3.8}$]-undec-2-ene-2-carboxylate Starting from intermediate 74 (0.600 g) the title compound was obtained as a yellow solid (0.241 g).

Tlc: CH-EA (1:1), $R_f$=0.29. IR: 3431 (OH); 1770 and 1718 (C=O) cm$^{-1}$. $^1$H-NMR: 7.78 (m); 7.72 (m); 7.31 (m); 7.20 (s); 6.68 (d); 5.85 (m); 5.38–5.10 (m); 4.80–4.60 (m); 4.29 (dd); 4.27 (m); 3.38 (m); 3.34 (dd); 3.11 (m); 2.23 (m); 2.14–1.94 (m); 1.78–1.50 (m); 1.34 (d).

INTERMEDIATE 86

Allyl (8S,9R,10S,12R)-1-aza-10-(1-Hydroxyethyl)-11-oxo-4-[(E)-(benzothiophen-3-yl)methylene]-tricyclo-[7,2,0,0$^{3.8}$]-undec-2-ene-2-carboxylate Starting from intermediate 75 (0.503 g) the title compound was obtained as a yellow foam (0.09 g).

Tlc: CH-EA (1:1), $R_f$=0.34. IR: 1772 and 1717 (C=O) cm$^{-1}$. $^1$H-NMR: 7.87 (dd); 7.78 (dd); 7.40 (m); 7.31 (s); 6.66 (s); 5.88 (m); 5.33 (m); 5.15 (m); 4.80–4.60 (m); 4.34 (dd); 4.29 (m); 3.37 (m); 3.14 (m); 3.02 (m); 2.20 (m); 2.04–1.96 (m); 1.75–1.60 (m); 1.36 (d).

INTERMEDIATE 87

Allyl (8S,9R,10S,12R)-1-aza-10-(1-Hydroxyethyl)-11-oxo-4-[(E)-[4-(4'-pyridyl)thiophen-2-yl]-methylene]-tricyclo-[7,2,0,0$^{3.8}$]-undec-2-ene-2-carboxylate Starting from intermediate 76 (0.47 g) the title compound was obtained as a yellow foam (0.303 g).

Tlc: DCM-Acetone (1:1), $R_f$=0.40. IR: 3692, 3605 (OH); 1776 and 1717 (C=O) cm$^{-1}$. $^1$H-NMR: 8.61 (m); 7.59 (d); 7.45 (m); 7.31 (m); 6.66 (d); 5.88 (m); 5.34 (m); 5.17 (m); 4.76 (m); 4.63 (m); 4.29 (dd); 4.27 (m); 3.34 (dd); 3.26 (dd); 3.09 (m); 2.22 (m); 2.10–1.95 (m); 1.77–1.5 (m); 1.34 (d).

INTERMEDIATE 88

Allyl (8S,9R,10S,12R)-1-aza-10-(1-Hydroxyethyl)-11-oxo-4-[(E)-(4-chloro-3-nitrophenyl)methylene]-tricyclo-[7,2,0,0$^{3.8}$]-undec-2-ene-2-carboxylate To a solution of intermediate 73 (0.15 g) in NMP (2 ml), DIPEA-HF (0.05 g) was added. The mixture was warmed at 40°, under a nitrogen atmosphere, for 24 h. The mixture was diluted with EE (50 ml) and washed with a saturated sodium bicarbonate solution; the organic layer was washed with water (2×50 ml) and brine (50 ml), dried and concentrated in vacuo, then purified by flash chromatography (eluting with CH-EA in gradient from 8:2 to 1:1) to give the title compound as a white solid (0.087 g).

Tlc: CH-EA (1:1), $R_f$=0.21. IR: 1776 and 1720 (C=O) cm$^{-1}$. $^1$H-NMR: 7.73 (d); 7.5 (d); 7.37 (dd); 6.45 (d); 5.87 (m); 5.4–5.2 (m); 5.34 (m); 4.8–4.6 (m); 4.3 (dd); 4.26 (m); 3.34 (dd); 3.09 (m); 2.88 (m); 2.2 (m); 2.–1.4 (m); 1.71 (d); 1.33 (d).

Using the same general procedure described for preparing intermediate 88 the following compounds were prepared

INTERMEDIATE 89

Allyl (8S,9R,10S,12R)-1-aza-10-(1-Hydroxyethyl)-11-oxo-4-[(E)-(4-(4'-pyridyl)thiazol-2-yl)methylene]-tricyclo-[7,2,0,0$^{3.8}$]-undec-2-ene-2-carboxylate Starting from intermediate 61 (0.40 g) the title compound as a yellow solid (0.12 g).

Tlc: CH-EA (2:8), $R_f$=0.26. IR: 1778 (C=O), 1720 (C=O), 1601 (C=C) cm$^{-1}$. $^1$H-NMR: 8.68 (d); 7.80 (d); 7.68 (s); 6.68 (d); 5.90 (m); 5.36 (m); 5.18 (m); 4.80 (m); 4.64 (m); 4.33 (dd); 4.28 (m); 4.04 (m); 3.38 (dd); 3.17 (m); 2.25 (m); 2.15 (m); 2.03 (m); 1.8–1.6 (m); 1.34 (d).

INTERMEDIATE 90

Allyl (8S,9R,10S,12R)-1-aza-10-(1-Hydroxyethyl)-
11-oxo-4-[(E)-(benzothiazol-2-yl)methylene]-
tricyclo-[7,2,0,0$^{3.8}$]-undec-2-ene-2-carboxylate Starting from intermediate 62 (0.27 g) the title compound was obtained as a yellow solid (0.036 g).

M.p. 175–177° C. Tlc: CH-EA (1:1), R$_f$=0.38. IR: 3443 (OH); 1759 (C=O), 1728 (C=O) cm$^{-1}$. $^1$H-NMR: 8.02 (d); 7.88 (d); 7.48 (m); 7.38 (m); 6.72 (d); 5.87 (m); 5.34 (m); 5.15 (m); 4.78 (m); 4.64 (m); 4.33 (dd); 4.29 (m); 4.00 (m); 3.38 (dd); 3.19 (m); 2.27 (m); 2.13 (m); 2.03 (m); 1.75 (m); 1.70 (m); 1.35 (d).

INTERMEDIATE 91

Allyl (8S,9R,10S,12R)-1-aza-10-(1-Hydroxyethyl)-
11-oxo-4-[(E)-(4-phenylthiazol-2-yl)methylene]-
tricyclo-[7,2,0,0$^{3.8}$]-undec-2-ene-2-carboxylate Starting from intermediate 65 (0.82 g) the title compound was obtained as a yellow solid (0.13 g).

Tlc: CH-EA (1:1), R$_f$=0.32. IR: 1776 (C=O), 1720 (C=O) cm$^{-1}$. $^1$H-NMR: 7.93 (m); 7.47–7.36 (s+m); 6.68 (d); 5.90 (m); 5.40–5.16 (m); 4.84–4.60 (m); 4.32 (dd); 4.29 (m); 4.07 (m); 3.37 (dd); 3.16 (m); 2.25 (m); 2.18–1.98 (m); 1.74 (m); 1.35 (d).

INTERMEDIATE 92

Allyl (8S,9R,10S,12R)-1-aza-10-(1-Hydroxyethyl)-
11-oxo-4-[(E)-(3-(4'-pyridyl)phenyl)methylene]-
tricyclo-[7,2,0,0$^{3.8}$]-undec-2-ene-2-carboxylate Starting from intermediate 66 (0.66 g) the title compound was obtained as a white foam (0.31 g).

Tlc: CH-EA (2:8), R$_f$=0.26. IR: 1778 (C=O), 1720 (C=O), 1601 (C=C) cm$^{-1}$. $^1$H-NMR: 8.68 (d); 7.80 (d); 7.68 (s); 6.68 (d); 5.90 (m); 5.36 (m); 5.18 (m); 4.80 (m); 4.64 (m); 4.33 (dd); 4.28 (m); 4.04 (m); 3.38 (dd); 3.17 (m); 2.25 (m); 2.15 (m); 2.03 (m); 1.8–1.6 (m); 1.34 (d).

INTERMEDIATE 93

Allyl (8S,9R,10S,12R)-1-aza-10-(1-Hydroxyethyl)-
11-oxo-4-[(E)-(4-(1'-(carbamoylmethyl)pyridinium-
4'-yliodide)thiazol-2-yl)methylene]-tricyclo-[7,2,0,
0$^{3.8}$]-undec-2-ene-2-carboxylate A stirred solution of intermediate 89 (0.05 g) and 2-iodoacetamide (0.2 g) in dry MeCN (4 ml) was warmed to 50° for 6 h in a closed vessel, after which EE (20 ml) was added to the mixture until a precipitate was formed. The mixture was centrifuged 3 times, decanting the supernatant and washing the remaining solid with EA each time, then the solid was dried in vacuo to give the crude title compound as a yellow solid (0.06 g) which was used in the following step without any further purification.

IR: (nujol) 1790, 1697, 1676 cm$^{-1}$. $^1$H-NMR (acetone d6): 9.15 (8H, d), 8.94 (1H, s); 8.79 (2H, d), 7.77 (1H, bs); 7.10 (1H, bs), 6.76 (1H, d); 5.92 (1H, m), 5.75 (2H, s); 5.38 (1H, m); 5.14 (1H, m), 4.75–4.6 (2H, m); 4.41 (1H, dd), 4.25 (1H, d); 4.19 (1H, m); 4.06 (1H, m); 3.50 (1H, dd); 3.29 (1H, m); 2.33 (1H, m); 2.15 (1H, m); 2.0 (1H, m); 1.4 (2H, m); 1.27 (3H, d).

INTERMEDIATE 94

Allyl (8S,9R,10S,12R)-1-aza-10-(1-Hydroxyethyl)-
11-oxo-4-[(E)-(N-(carbamoylmethyl)-2-furyl[3,2-c]
pyridiniumiodide)methylene]-tricyclo-[7,2,0,0$^{3.8}$]-
undec-2-ene-2-carboxylate A stirred solution of intermediate 81 (0.05 g) and 2-iodoacetamide (0.11 g) in dry MeCN (4 ml) was warmed to 50° for 6 h in a closed vessel, after which EE (20 ml) was added to the mixture until a precipitate was formed. The mixture was centrifuged 3 times, decanting the supernatant and washing the remaining solid with EA each time, then the solid was dried in vacuo to give the crude title compound as a yellow solid (0.04 g).

IR: (nujol) 3200–3400 (OH, NH); 1777, 1721, 1678 (C=O) cm$^{-1}$. $^1$H-NMR (DMSO): 9.33 (s), 8.80 (dd); 8.38 (d), 7.99 (s); 7.69 (s), 7.41 (s); 6.51 (d); 5.81 (d); 5.41 (s); 5.29 (dd); 5.10 (d),5.08 (d); 4.67 (m); 4.56 (m), 4.28 (dd); 3.99 (s); 3.46 (dd); 3.41 (m); 3.21 (m); 2.31 (m); 2.02 (m); 1.85 (1m); 1.75–1.6 (m); 1.10 (d).

INTERMEDIATE 95

Allyl (8S,9R,10S,12R)-1-aza-10-(1-Hydroxyethyl)-
11-oxo-4-[(E)-(4-(1'-(carbamoylmethyl)pyridinium-
4'-yliodide)thiophen-2-yl)methylene]-tricyclo-[7,2,0,
0$^{3.8}$]-undec-2-ene-2-carboxylate A solution of iodoacetamide (0.209 g) in MeCN (2 ml) was added to a solution of intermediate 87 (0.097 g) in MeCN (6 ml) The mixture was heated to 50° in sealed tube for 2 h, then, more iodoacetamide (0.095 g) was added, heating was continued for 2 h, then another additon of iodoacetamide (0.030 g) was made. After 0.5 h, the mixture was cooled, the solution was concentrated under a nitrogen stream then EE was added slowly until precipitation of a yellow solid occurred. The solid was centrifuged twice, washed with EA, then dried under high vacuum to give the crude title compound as a yellow solid (0,131 g).

$^1$H-NMR: 8.91 (d); 8.73 (s); 8.47 (d); 8.01 (s); 7.88 (s); 7.70 (s); 6.59 (s); 5.82 (m); 5.31 (m); 5.30 (s); 5.11 (m); 5.09 (d); 4.66 (m); 4.57 (m); 4.27 (dd); 4.00 (m); 3.42 (ddm); 3.15 (m); 3.13 (m); 2.21 (m); 2.00–1.87 (m); 1.55–1.7 (m); 1.12 (d).

INTERMEDIATE 96

N-Allyloxycarbonyl-4-piperidincarboxylic Acid

To a solution of 4-piperidincarboxylic acid (25 g) in dry DCM (30 ml) a solution of NaOH 2N (207 ml) was added. The reaction mixture was then cooled to 0–5° and a solution of allylchloroformate (22 ml) in DCM (1 ml) was added over 40 min. The reaction was stirred at 0–5° C. for 2 h, then NaOH 2N (40 ml) was added and the organic phase was separated. The aqueous phase was washed with DCM, then acidified with H$_2$SO$_4$ conc. (10 ml) to pH2 and extracted with EA. The organic layer was washed with brine, dried and the solvent removed in vacuo to give the title compound as a colourless oil (39.5 g).

IR: 1730 cm$^{-1}$. 1H-NMR (CDCl$_3$): 10.5 (bs); 5.99 (m); 5.2 (m); 4.6 (m); 4.05 (m); 3.00 (m); 2.50 (m); 1.85 (m); 1.60 (m).

INTERMEDIATE 97

N-Allyloxycarbonyl-4-(bromoacetyl)piperidine

To a solution of intermediate 96 (10 g) in dry DCM (90 ml) few drops of dry DMF were added, then the solution was cooled to 0° C. and oxalyl chloride (7.8 ml) was added. The reaction was stirred for 2 h at r.t., then the solvent was removed in vacuo. The crude was then dissolved in dry THF (150 ml), cooled to 0° C. and (trimethylsylil)diazomethane (59 ml) was added. After stirring for 1 h at r.t., the reaction was diluted with diethyl ether and washed with a saturated solution of NaHCO$_3$, brine, dried over Na$_2$SO$_4$. The crude residue was concentrated then diluted with diethyl ether, cooled to 0° C. and a 33% in acetic acid solution of HBr (8.2 ml) was slowly added. The reaction was stirred for 1 h at r.t., then diluted with diethyl ether, washed with a saturated solution of NaHCO$_3$, brine, dried and the solvent removed in vacuo The crude residue was purified by flash-chromatography (CH/EA 4/1 to 1/1) to give the title compound as an orange oil (11 g).

IR: 1699 cm$^{-1}$. 1H-NMR (CDCl$_3$): 5.99 (m); 5.30 (m); 4.68 (m); 4.4 (m); 4.0 (s); 2.90 (m); 1.90 (m); 1.55 (m).

INTERMEDIATE 98

Diethoxythioacetamide

To a suspension of phosphorus pentasulfide (27 g) in dry THF (100 ml) at 0° C. under vigorous stirring, Na$_2$CO$_3$ (13 g) was added. The reaction mixture was stirred for 30 min at 0° C. and for 30 min at r.t., then diethoxyacetamide (6 g) was added and stirring was continued at r.t. for 70 h. The reaction was then diluted with EA, washed with 10% Na$_3$PO$_4$, brine, dried over Na$_2$SO$_4$ and the solvent removed in vacuo. The crude residue was purified by flash-chromatography (EE/PE 1/1) to give the title compound as a white solid (4.4 g).

1H-NMR (CDCl$_3$): 7.9–7.6 (bs); 5.05 (s); 3.8–3.6 (m); 1.2–1.4 (m).

INTERMEDIATE 99

2-(Diethoxymethyl)-4-[4'-(N-allyloxycarbonyl) piperidinyl]thiazole

Intermediate 97 (11 g) and intermediate 98 (6.2 g) were dissolved in dry ethanol and stirred for 2 h at 50° C. The reaction mixture was then diluted with Et$_2$O, washed with a saturated solution of NaHCO$_3$, brine, dried and the solvent removed in vacuo. The crude residue was purified by flash-chromatography (EE/PE 1/1) to give the title compound as an orange oil (12.2 g).

IR: 1688 cm$^{-1}$. 1H-NMR (CDCl$_3$): 6.89 (s); 5.94 (m); 5.66 (s); 5.4–5.18 (m); 4.60 (m); 4.26 (m); 3.75–3.6 (m); 2.93.

INTERMEDIATE 100

2-(Formyl)-4-[4'-(N-allyloxycarbonyl)piperidinyl] thiazole

To a solution of intermediate 99 (0.2 g) in dry DCM (3 ml) formic acid (93 ml) was added and the reaction stirred for 1 h at r.t. The solvent was then removed in vacuo, then Et$_2$O (two times) was added and stripped away to eliminate traces of formic acid. The title compound was recovered as an oil (160 mg).

IR: 1691 cm$^{-1}$. 1H-NMR (CDCl$_3$): 9.97 (d); 7.36 (t); 5.96 (m); 5.4–5.18 (m); 4.60 (m); 4.32 (m); 3.0 (m); 2.11 (m); 1.74 (m).

INTERMEDIATE 101

(3S,4R)-1-[(Allyloxycarbonyl) (triphenylphosphoranylidene)methyl]-3-[(R)-(tert-butyldimethylsilyloxy)ethyl]-4-[(6'R)-2'-{[4"(N-allyloxycarbonylpiperidin-4-yl)thiazol-2"-yl]-(p-toluenesulfonyloxy)methyl}-1'-oxo-cyclohex-6'-yl] azetidin-2-one A solution of intermediate 18 (1.6 g) in dry THF (13 ml) was added dropwise to a stirred solution of LHMDS (5.12 ml of a 1M solution in hexane) in dry THF (10 ml), cooled to –78° C. and under nitrogen atmosphere. The mixture was stirred until the temperature reached –60° C. (over about 0.5 h), then cooled to –78° C. and at this point a solution of intermediate 100 (1.5 g) in dry THF (10 ml) was added dropwise. The reaction mixture was stirred until the temperature reached –60° C., then it was transferred via a cannula over 10 min into a stirred solution of p-toluenesulfonyl chloride (1.33 g) in dry THF (14 ml). The mixture was stirred for further 10 min at r.t., then the reaction was quenched by pouring it into a saturated sodium bicarbonate solution (150 mL). The mixture was extracted with EA (3×100 mL). The organic layer was washed with brine, dried and the solvent evaporated under reduced pressure. The crude residue was purified by flash chromatography (eluting with CH/EA in gradient from 6:4 to 4:6) to give the title compound as a yellow foam (1.97 g) which was used in the following step without any further characterization and purification.

INTERMEDIATE 102

(3S,4R)-1-[(Allyloxycarbonyl) (triphenylphosphoranylidene)methyl]-3-[(R)-(tert-butyldimethylsilyloxy)ethyl]-4-[(6'R)-2'-{(E)-[4"(N-allyloxycarbonylpiperidin-4-yl)thiazol-2"-yl]-methylene}-1'-oxo-cyclohex-6'-yl]azetidin-2-one To a stirred solution of the intermediate 101 (1.97 g) in dry DCM (75 ml), at 23° C. and under a nitrogen atmosphere, a solution of DBU (0.29 ml) in dry DCM (5 mL) was added dropwise over 3 min. Stirring was continued for 15 min then the reaction mixture was poured into a saturated ammonium chloride solution (100 mL). The mixture was extracted with EA (3×100 mL). The organic layer was washed with brine, dried and the solvent evaporated under reduced pressure. The crude residue was purified by flash chromatography (CH/EA 4/6) to give the title compound as a yellow foam (1.23 g) which was used in the following step without any further characterization and purification.

INTERMEDIATE 103

Allyl (8S,9R,10S,12R)-1-aza-10-[1-(tert-Butyldimethylsilyloxy)ethyl]-11-oxo-4-{(E)-[4'(N-allyloxycarbonylpiperidin-4-yl)thiazol-2'-yl]-methylene}-tricyclo-[7,2,0,0$^{3,8}$]-undec-2-ene-2-carboxylate A solution of intermediate 102 (1.239 g) in dry toluene (100 ml), under a nitrogen atmosphere, was warmed to 100° and stirred for 1.5 h. The organic solvent was evaporated under reduced pressure. The crude residue was purified by flash chromatography (CH/EA 1/1) to give the title compound as a yellow foam (0.48 g).

1H-NMR (CDCl$_3$): 6.85 (s); 6.61 (d); 5.95–5.86 (ddt); 5.32–5.31 (dq); 5.21–5.14 (dq); 4.74 (m); 4.64–4.58 (m); 4.27 (bs); 4.25 (dd); 4.22 (m); 3.79 (m); 3.29 (dd); 3.07 (m); 2.93 (m); 2.16 (m); 2.08 (m); 2.05 (m); 1.94 (m); 1.68 (m); 1.66 (m); 1.64 (m); 1.24 (d); 0.89 (s); 0.08 (s+s).

INTERMEDIATE 104

Allyl (8S,9R,10S,12R)-1-aza-10-(1-Hydroxyethyl)-11-oxo-4-{(E)-[4'(N-allyloxycarbonylpiperidin-4-yl) thiazol-2'-yl]-methylene}-tricyclo-[7,2,0,0$^{3,8}$]-undec-2-ene-2-carboxylate Glacial acetic acid (0.60 ml) and TBAF.3H$_2$O (3.10 g) were added respectively to a stirred solution of intermediate 103 (0.47 g) in THF (15 ml) cooled at 0° C. The temperature was allowed to raise at 23° C. and the mixture was stirred under a nitrogen atmosphere for 15 h. The mixture was diluted with EA (50 ml) and washed with a saturated solution of sodium bicarbonate (2×50 ml), brine (50 ml), dried and concentrated in vacuo, then purified by flash chromatography (CH/EA 8/2) to give the title compound as a yellow foam (0.23 g).

1H-NMR (CDCl$_3$): 6.86 (s); 6.23 (d); 5.95–5.86 (ddt); 5.32–5.31 (m); 5.21–5.15 (m); 4.77 (m); 4.64–4.58 (m); 4.29 (dd); 4.25 (m); 4.2–4.3 (m); 3.81 (m); 3.34 (dd); 3.12 (m); 2.93 (m); 2.2–1.95 (m); 2.05 (m); 1.75–1.5 (m); 1.66 (m); 1.33 (d);

INTERMEDIATE 105

(3S,4R)-3-[(1R)-(t-Butyldimethylsilyloxy)ethyl]-4-{(3'R)-[4'-oxo-tetrahydrothiopyran-3'-yl]}azetidin-2-one A 1.6 M solution of n-butyllithium in hexane (84.7 mL) was added dropwise to a stirred solution of diisopropylamine (19.01 mL) in THF (100 mL) at −30° C. under nitrogen atmosphere. After 10 min the mixture was cooled to −78° C. and a solution of tetrahydrothiopyran-4-one (15 g) in THF (130 mL) was added dropwise. After 30 min a solution of [3R(1'R,4R)]-4-acetoxy-3-[1-(tert-butyldimethylsilyloxy)ethyl]azetidin-2-one (18.55 g) in THF (75 mL) was added dropwise and the reaction mixture was stirred at the same temperature for further 15 min. The reaction was quenched by pouring the mixture into a saturated solution of ammonium chloride (150 mL). The organic layer was extracted with EA (3×100 mL), washed with brine, dried and the solvent evaporated under reduced pressure. The crude residue was purified by flash chromatography (eluting with CH-EA in gradient from 1:1 to 4:6) to give the title compound as a white solid (4.68 g).

Tlc: CH-EA (1:1), R$_f$=0.26. IR: 3414 (N—H);1759, 1709 (C=O). $^1$H-NMR: 5.80 (bs); 4.20 (m); 4.10 (m); 2.90–2.70 (m); 1.20 (d); 0.90 (s); 0.08 (s+s).

INTERMEDIATE 106

(3S,4R)-1-[(Allyloxycarbonyl)carbonyl]-3-[(1R)-(t-butyldimethylsilyloxy)ethyl]-4-{(3'R)-[4'-oxo-tetrahydrothiopyran-3'-yl]}azetidin-2-one Allyloxalylchloride (1.51 g) was added dropwise to a stirred solution of TEA (4.56 mL) in DCM (40 mL) at 0° C. and under a nitrogen atmosphere. After 2 min, a solution of intermediate 105 (4.68 g) in DCM (65 mL) was added dropwise keeping the mixture temperature at 0° C. The mixture was stirred for further 20 min, then the reaction was quenched by pouring the mixture into a saturated sodium bicarbonate solution (100 mL). The mixture was extracted with EE (3×100 mL). The organic layer was washed with brine, dried and the solvent evaporated under reduced pressure to give the crude title compound as a white solid (6.63 g) which was used in the following step without any further characterisation and purification.

Tlc: CH-EA (1:1), R$_f$=0.51.

INTERMEDIATE 107

(3S,4R)-1-[(Allyloxycarbonyl)(triphenylphosphoranylidene)methyl]-3-[(1R)-1-(tert-butyldimethylsilyloxy)ethyl]-4-[(3'R)-4-oxo-tetrahydrothiopyran-3'-yl]azetidin-2-one To a stirred solution of intermediate 106 (6.63 g) in dry toluene (27 mL), at room temperature and under nitrogen atmosphere, TPP (14.3 g) was added portionwise. Then, a solution of Diethoxymethylphosphite (2.66 mL, 80% purity) in dry toluene (5 mL) was added over 15 min. After 3 h, the mixture was partially concentrated under reduced pressure and the residue was purified by flash chromatography (eluting with CH-EA in gradient from 8:2 to 6:4) to give the title compound as a white foam (4.54 g) which was used in the following step without any further characterization.

Tlc: CH-EA (4:6), R$_f$=0.39.

INTERMEDIATE 108

(3S,4R)-1-[(Allyloxycarbonyl)(triphenylphosphoranylidene)methyl]-3-[(1R)-1-(tert-butyldimethylsilyloxy)ethyl]-4-[(5'R)-3'-[(4-pyridyl)(p-toluenesulfonyloxy)methyl]-4'-oxo-tetrahydrothiopyran-5'-yl]azetidin-2-one A solution of intermediate 107 (2.20 g) in dry THF (20 mL) was added dropwise to a stirred solution of LHMDS (6.80 mL of a 1M solution in hexane) also in dry THF (15 mL), kept at −78° C. under a nitrogen atmosphere. The mixture was stirred until the temperature reached −60° C. (over about 0.5 h), then cooled to −78° C.; at this point a solution of 4-pyridinecarboxaldehyde (0.6 mL) in dry THF (8 mL) was added dropwise. The reaction mixture was stirred until the temperature reached −60° C., then transferred by cannula over 10 min into a stirred solution of p-toluenesulfonyl chloride (1.25 g) in dry THF (35 mL), under a nitrogen atmosphere, at 23° C. The mixture was stirred for further 10 min, then the reaction was quenched by pouring the mixture into a saturated sodium bicarbonate solution (100 mL). The mixture was extracted with EA (3×100 mL). The organic layer was washed with brine, dried and the solvent evaporated under reduced pressure. The crude residue was purified by flash chromatography (eluting with CH-EA in gradient from 6:4 to 3:7) to give the title compound as a yellow foam (2.14 g) which was used in the following step without any further characterisation.

Tlc: CH-EA (4:6), R$_f$=0.21, 0.23.

INTERMEDIATE 109

(3S,4R)-1-[(Allyloxycarbonyl)(triphenylphosphoranylidene)methyl]-3-[(1R)-1-(tert-butyldimethylsilyloxy)ethyl]-4-[(5'R)-3'-[(E)-(4-pyridyl)methylene]-4'-oxo-tetrahydrothiopyran-5'-yl]azetidin-2-one To a stirred solution of the intermediate 108 (2.05 g) in dry DCM (80 mL), at 23° C. and under a nitrogen atmosphere, a solution of DBU (0.35 mL) in dry DCM (5 mL) was added dropwise over 3 min. Stirring was continued for 15 min then the reaction mixture was poured into a saturated ammonium chloride solution (100 mL). The mixture was extracted with EA (3×100 mL). The organic layer was washed with brine, dried and the solvent evaporated under reduced pressure. The crude residue was purified by flash chromatography (eluting with CH-EA in gradient from 1:1 to 3:7) to give the title compound as a yellow foam (1.19 g) which was used in the following step without any further characterization.

Tlc: CH-EA (4:6), R$_f$=0.22.

INTERMEDIATE 110

Allyl (8S,9R,10S,12R)-1-aza-10-[1-(tert-Butyldimethylsilyloxy)ethyl]-6-thia-11-oxo-4-[(E)-(4-pyridyl)methylene]-tricyclo-[7,2,0,0$^{3,8}$]-undec-2-ene-2-carboxylate A solution of intermediate 109 (1.19 g) in dry toluene (80 mL), under a nitrogen atmosphere, was heated to 100° C.

and stirred for 1.0 h, then the organic solvent was evaporated under reduced pressure. The crude residue was purified by flash chromatography (eluting with CH-EA in gradient from 1:1 to 4:6) to give the title compound as a yellow foam (0.64 g).

Tlc: CH-EA(2:8), $R_f$0.38. IR: 1780(C=O), 1724 (C=O). $^1$H-NMR: 8.60 (d); 7.14 (d); 6.42 (s); 5.89 (m); 5.36 (m); 4.73 (m); 4.66 (m); 4.32 (dd); 4.25 (m); 3.64 (d); 3.58 (m); 3.40 (d); 3.32 (dd); 3.01 (t); 2.70 (dd); 1.26 (d); 0.90 (s); 0.10 (s).

INTERMEDIATE 111

Allyl (8S,9R,10S,12R)-1-aza-10-(1-Hydroxyethyl)6-thia-11-oxo-4-[(E)-(4-pyridyl)methylene]-tricyclo-[7,2,0,0$^{3.8}$]-undec-2-ene-2-carboxylate Glacial acetic acid (0.58 mL) and TBAF. (2.57 g) were added respectively to a stirred solution of intermediate 110 (0.35 g) in THF (8 mL) at 0° C. The temperature was allowed to raise at 23° C. and the mixture was stirred under a nitrogen atmosphere for 15 h. The mixture was diluted with a saturated aqueous ammonium chloride solution (10 mL) and EA (50 mL); the organic layer was washed with concentrated sodium bicarbonate solution (3×50 mL) and brine (50 mL), dried and concentrated in vacuo, then purified by flash chromatography (eluting with CH-EA in gradient from 3:7 to 1:9) to give the title compound as a yellow foam (0.18 g).

Tlc: CH-EA (2:8), $R_f$0.15. IR: 1782, 1722 (C=O). $^1$H-NMR: 8.60 (d); 7.14 (d); 6.42 (s), 5.88 (m); 5.35 (dq); 5.22 (dq); 4.75 (m); 4.65 (m); 4.35 (dd); 4.27 (m); 3.64 (dd); 3.61 (m); 3.39 (dd); 3.36 (dd), 3.00 (t); 2.76 (m); 1.35 (d).

INTERMEDIATE 112

1-Trimethylsilyloxy-2-[(E)-(pyrid-4-yl)methylene]cyclohexene

Triethylamine (2.13 L) was added to a suspension of 2-[(E)-(Pyrid-4-yl)methylene]cyclohexanone thifluoroacetic acid salt (758 g), in acetonitrile (6.06 L) at room temperature resulting in complete dissolution. Trimethylsilychloride (0.95 L) was then added over 15 min, the mixture was stirred at 60° C. for 2 h 30 min., cooled to 10° C. and poured into a beaker containing ethyl acetate (9 L) and NaHCO3 (5%, 3.64 L) with stirring. The organic layer was washed with cold sat. NH4Cl (2×7.5 L) and brine (2×7.5 L). The organic phase was dried (Na2SO4) and concentrated at 40° C. in vacuo to give the title compound as a solution in ethyl acetate (1.29 L).

INTERMEDIATE 113

(3S,4R)-3-[(R)-1-(t-Butyldimethylsilyloxy)ethyl]-4-[(R)-2'-(S)-6'[(E)-(pyrid-4-yl)methylene]-1'-oxocyclohexyl]azetidin-2-one and (3S,4R)-3-[(R)-1-(t-Butyldimethylsilyloxy)ethyl]-4-[(R)-2'-[(R)-6' [(E)-(pyrid-4-yl)methylene]-1'-oxocyclohexyl] azetidin-2-one and L-Tartrate Salts The solution of Intermediate 112 in ethyl acetate (1.29 L.) was added to (3R,4R)-4-acetoxy-3(R)-(t-butyldimethylsilyoxy)-ethyl-2-azetidinone (720 g) dissolved in acetonitrile (5.87 L). The solution was cooled to −15° C. and trimethylsilyl triflate (0.455 L) was added over 30 min keeping the temperature <−2° C. Further trimethylsilyl triflate (0.455 L) was then added dropwise over 2 h. The resulting solution was stirred at 0° C. for 1 h and then poured into a mixture of cold saturated NaHCO3 (4.9 L) and ethyl acetate (8.6 L).

The organic layer was washed with sat NaHCO3 (3.8 L), water (3×3.8 L) and brine (2×3.8 L). The organic phase was dried (Na2SO4) and concentrated at 45° C. in vacuo to 1.97 L. Isopropylalcohol (2.58 L) and L(+)-Tartaric acid (190 g) were then added to the concentrate. The resulting solution was warmed to 75° C. and stirred for 1 h then cooled to 2° C. for 1 h. The resulting yellow solid was filtered and washed with ethyl acetate (1.63 L) to give the title compounds product in the form of their L-tartrate salts (711 g).

An aqueous solution of NaHCO3 (5%, 900 ml) was added over 30 minutes to a suspension of the L-tartrate salt (180 g) in ethyl acetate (900 ml). After stirring for 1 hr the two phases were separated and the organic layer was washed with a 5% NaHCO3 solution (450 ml) and water (450 ml), filtered over Celite and evaporated to afford the title compounds (150 g) in the form of their free base.

INTERMEDIATE 114

(3S,4R)-3[(R)-1-(t-Butyldimethylsilyloxy)ethyl]4-[(R)-2'-[(S)-6'-[(E)-(pyrid-4-yl)methylene]-1'-oxocyclohexyl]azetidin-2-one Method A A solution of oxamic acid (890 mg) in methanol (42 ml) was added over 20 minutes to a solution of Intermediate 113 (free base) (4.2 g) in isopropanol (21 ml) at room temperature.

After stirring for 5 minutes the methanol was removed under vacuum (T<25° C.). and the residual suspension was cooled to 0° C. and stirred for 1 hr. The filtration of the solid and its washing with cold isopropanol (2 ml) afforded a clear solution that was diluted with ethyl acetate (42 ml), extracted with 5% aqueous bicarbonate solution (2×21 ml), brine (21 ml) dried and evaporated to give the title compound (2 g).

Method B

A solution of oxalic acid (126 mg) in methanol (1 ml) was added in 30 minutes to a solution of Intermediate 113 (free base) (420 mg) in ethyl acetate (4 ml) at room temperature.

After stirring for 5 minutes the methanol was removed under vacuum (T<25° C.). and the residual suspension was cooled to 0° C. and stirred for 1 hr.

The filtration of the solid and its washing with ethyl acetate (2×1 ml) afforded a clear solution that was diluted with ethyl acetate (4 ml), extracted with 5% aqueous bicarbonate solution (2×1 ml), brine (1 ml) dried and evaporated to give the title compound (170 mg).

INTERMEDIATE 115

(3S,4R)-1[(Allyloxyoxalyl)-3-R-1-(t-butyldimethylsilyloxy)ethyl]-4-[(2'R,6'S)-6'-[(E)-(pyrid-4-yl)methylene]-1'-oxocyclohexyl]azetidin-2-one A mixture of oxalyl chloride (3 ml, 2.2 eq) and ethyl acetate (25 ml) was chilled to −30° C., and treated with a solution of intermediate 114 (6 g) and diisopropylethylamine (10.5 ml, 4.2 eq) in ethyl acetate (15 ml) dropwise over 40 min at −30 to −40° C. Stirring for a further 20 min at −30° C. gave complete consumption of starting material. Allyl alcohol (7.5 ml) was added, and the mixture stirred for 5 min at −30° C. 50% Saturated sodium bicarbonate (30 ml) was added and the mixture allowed to warm to room temperature. The phases were separated, and organics washed with 50% saturated sodium chloride solution (30 ml), saturated sodium chloride solution (30 ml), dried (MgSO$_4$) and evaporated to leave a brown/orange solid. The solid was suspended in ethyl acetate (7.5 ml) and chilled (ice bath) as iso-octane (30 ml) was added dropwise over 30 min, and the resulting suspension held a further 45 min at 5° C. The suspension was filtered and the product washed with iso-octane (30 ml) and dried in vacuo at room temperature for 1 h to give title compound as pale yellow crystalline solid (3.5 g).

INTERMEDIATE 116

Allyl (8S,9R,10S,12R)-1-aza-10-[1-(tert-Butyldimethylsilyloxy)ethyl]-11-oxo-4-[(E)-(pyrid-4-yl)methylene]-tricyclo-[7,2,0,0$^{3.8}$]-undec-2-ene-2-carboxylate Intermediate 115 (3.5 g) was dissolved in toluene (35 ml) and treated with diethoxymethylphosphine (2.2 ml, 2.1 eq) to give a dark solution. After 1 h at room temperature the solution had lightened to a red colour. The solution was warmed to 70° C. and held for 3 h, then cooled to 30° C. and treated with sodium chloride solution (30% saturated, 35 ml). The mixture was stirred vigorously for 5 min, the phases separated and the aqueous extracted with ethyl acetate (20 ml). Combined organic phases were washed with saturated sodium chloride solution (2×25 ml), dried (MgSO$_4$) and evaporated to leave an oil. The oil was chromatographed (Dichloromethane then dichloromethane: ethyl acetate 3:1) to give product as yellow foam, which was dissolved in tert-butyl methyl ether (1 ml), chilled (ice bath) to initiate crystallisation. Iso-octane (10 ml) was added dropwise, and the batch held a further 60 min at 5° C., then filtered and the solid washed with iso-octane (5 ml) and dried in vacuo to yield title compound as a white crystalline solid.

INTERMEDIATE 117

Allyl (8S,9R,10S,12R)-1-aza-10-(1-Hydroxyethyl)-11-oxo-4-[(E)-(pyrid-4-yl)methylene]-tricyclo-[7,2,0,0$^{3.8}$]-undec-2-ene-2-carboxylate Intrmediate 116 (2.6 g) was dissolved in N-methyl pyrolidinone (5 ml) and treated with diisopropylethylamine HF complex (3.3 ml, excess). The reaction mixture was held overnight at room temperature then quenched into saturated sodium bicarbonate (50 ml). The mixture was extracted with ethyl acetate (2×50 ml), and combined organics were washed with sodium chloride solution (40% sat$^d$ 50 ml, sat$^d$ 50 ml), dried (MgSO$_4$) and evaporated to leave orange residue. This residue was chromatographed (ethyl acetate) to leave title compound as pale yellow foam (1.4 g).

A portion of the foam (0.06 g) was dissolved in isopropanol (0.18 ml) and diisopropyl ether (1.8 ml) added over 30 min following the addition of an authentic seed to the cloudy solution. The crystalline suspension was cooled to 0° and stirred for 1 h. The solid was isolated by filtration and the solid washed with diisopropyl ether (2×0.2 ml) to give title compound as a crystalline solid (0.036 g).

INTERMEDIATE 118

(3S,4R)-1-[(Fluorenylmethyloxyoxalyl)-3R-1-(t-butyldimethylsilyloxy)ethyl]-4-(2'R,6'S)-6'-[(E)-(pyrid-4-yl)methylene]-1'-oxocyclohexyl]azetidin-2-one Intermediate 114 (1 g) was dissolved in dichloromethane (4 ml) at 0° C. and diisopropylethylamine (1.26 ml) was added and then a solution of fluorenylmethyloxalyl chloride (1.38 g) in dichloromethane (4 ml) was added over 1 min while keeping the temperature between 0° C. and 5° C. After 10 min the reaction was complete (HPLC).

The organic phase was diluted with ethyl acetate (30 ml) and then was washed with NaHCO$_3$ 2.55% (20 ml), NH$_4$Cl 10% (20 ml), water (20 ml), brine (20 ml), dried (Na$_2$SO$_4$) and then concentrated at room temperature under vacuum to give the title compound foam which was used without further purification.

INTERMEDIATE 119

Fluorenylmethyl (8S,9R,10S,12R)-1-aza-10-[1-(tert-Butyldimethylsilyloxy)ethyl]-11-oxo-4-[(E)-(pyrid-4-yl)methylene]-tricyclo-[7,2,0,0$^{3.8}$]-undec-2-ene-2-carboxylate Intermediate 118 was dissolved in toluene (13 ml) at r.t. and (EtO)$_2$PMe (1.1 ml) was added. After 60 min the solution was heated to 70° C. and stirred over 3.5 h. The mixture was cooled to room temperature. Water (20 ml) was added and the organic phase separated and then washed with NaHCO$_3$ 5% (20 ml), NH$_4$Cl 10% (20 ml), brine (20 ml) dried (Na$_2$SO$_4$), concentrated. To the brown foam/solid obtained, t-butylmethyl ether (6 ml) was added and heated at reflux obtaining a suspension. Then, isopropylether (4 ml) was added and the suspension was slowly cooled ad 0deg in about 1 hour and then stirred for 30 minutes. The suspension was filtered, washed with t-butylmethylether (1 ml)/isopropylether (3 ml) (twice) and then dried to give the title compound (575 mg).

INTERMEDIATE 120

Fluorenylmethyl (8S,9R,10S,12R)-1-aza-10-(1-Hydroxyethyl)-11-oxo-4-[(E)-(pyrid-4-yl) methylene]-tricyclo-[7,2,0,0$^{3.8}$]-undec-2-ene-2-carboxylate Intermediate 119 (7.34 g) was suspended in N-methyl pyrrolidinone (73.4 ml) and treated with diisopropylethylamine HF complex (9.2 ml, excess). The reaction mixture was held overnight (18 hrs) at room temperature then quenched into saturated sodium bicarbonate (370 ml). The mixture was extracted with ethyl acetate (2×370 ml), and combined organics were washed with saturated sodium chloride solution (2×370 ml), water (370+185 ml), dried (Na$_2$SO$_4$) and evaporated to leave orange foam. This was chromatographed (ethyl acetate/cyclohexane=8/2 then 9/1) to give title compound as pale yellow foam (4.26 g).

EXAMPLE 1

Sodium (8S,9R,10S,12R)-1-aza-10-(1-Hydroxyethyl)-11-oxo-4-[(E)-phenylmethylene]-tricyclo-[7,2,0,0$^{3.8}$]-undec-2-ene-2-carboxylate To a stirred solution of intermediate 77 (0.05 g) and TPP (0.002 g) in dry THF (3 ml) at 23° and under a nitrogen atmosphere, tetrakis(triphenylphosphine)palladium (0.008 g) was added, followed by a 0.5 M solution of sodium 2-ethylhexanoate in EA (0.24 ml). After 0.25 h PE (6 ml) was added to the reaction mixture until a precipitate was formed. The mixture was centrifuged 3 times, decanting the supernatant and washing the remaining solid with EE each time, then the solid was dried in vacuo to give the crude title compound as a white solid (0.026 g).

IR: 3445–3364 (OH), 1780 (C=O), 1618–1595 (C=O, C=C) cm$^{-1}$. $^1$H-NMR (D2O) 7.30–7.10 (m); 6.27 (m); 4.13

(dd); 4.08 (m); 3.40 (dd); 2.93 (m); 2.75 (m); 2.04 (m); 1.84–1.70 (m); 1.50–1.00 (m); 1.10 (d).

EXAMPLE 2

(8S,9R,10S,12R)-1-aza-10-(1-Hydroxyethyl)-11-oxo-4-[(E)-(4-(1'-(carbamoylmethyl)pyridinium-4'-yl)thiazol-2-yl)methylene]-tricyclo-[7,2,0,0$^{3.8}$]-undec-2-ene-2-carboxylate To a stirred solution of intermediate 93 (0.06 g) in dry DMF (2 ml) at 23°, under a nitrogen atmosphere, tetrakis (triphenylphosphine)palladium (0.01 g) was added followed by tributyltin hydride (0.03 ml). After 1 h the organic tin compound was extracted washing the reaction mixture 3 times with PE (5 ml×3) then EE (20 ml) was added until a precipitate was formed. The mixture was centrifuged 3 times, decanting the supernatant and washing the remaining solid with EA each time, then the solid was dried in vacuo. The crude product was purified by preparative HPLC (mobile phase: MeCN-water) followed by lyophilization to give the title compound as a orange solid (0.018 g).

IR: (nujol) 1760, 1695 cm$^{-1}$. $^1$H-NMR (D2O): 8.63 (2H, d); 8.44 (1H, s), 8.35 (2H, d); 6.54 (1H, s); 5.35 (2H, s), 4.22 (1H, dd); 4.15 (1H, m); 3.52 (1H, m); 3.40 (1H, m); 3.10 (1H, m); 2.20 (1H, m); 1.99 (1H, m); 1.88 (1H, m); 1.64–1.5 (2H, m); 1.16 (3H, d).

Using the general procedure described for preparing example 1, the following compounds were prepared:

EXAMPLE 3

Sodium (8S,9R,10S,12R)-1-aza-10-(1-Hydroxyethyl)-11-oxo-4-[(E)-(4-(4'-pyridyl)thiazol-2-yl)methylene]-tricyclo-[7,2,0,0$^{3.8}$]-undec-2-ene-2-carboxylate Starting from intermediate 89 (0.10 g) a crude product was obtained and thenpurified by preparative HPLC (mobile phase: MeCN-water, from 9:1 to 1:1) followed by lyophilization to give the title compound as a white solid (0.05 g).

IR: 1738 (C=O), 1587 (C=C) cm$^{-1}$; $^1$H-NMR (D2O): 8.45 (d); 7.94 (s); 7.73 (d); 6.52 (d); 4.21 (dd); 4.14 (m); 3.51 (dd); 3.35 (m); 3.08 (m); 2.18 (m); 2.00 (m); 1.88 (m); 1.55–1.1 (m); 1.16 (d).

EXAMPLE 4

Sodium (8S,9R,10S,12R)-1-aza-10-(1-Hydroxyethyl)-11-oxo-4-[(E)-(benzothiazol-2-yl)methylene]-tricyclo-[7,2,0,0$^{3.8}$]-undec-2-ene-2-carboxylate Starting from intermediate 90 (0.032 g) a crude title compound was obtained as a yellow solid (0.008 g).

IR: 1753 (C=O), 1585 (C=C, C=O) cm$^{-1}$. $^1$H-NMR (D2O): 7.86 (d); 7.81 (d); 7.42 (m); 7.32 (m); 6.53 (m); 4.18 (dd) 4.10 (m); 3.48 (m); 3.33 (m); 3.07 (m); 2.18 (m); 1.94 (m); 1.84 (m); 1.51 (m); 1.12 (d).

EXAMPLE 5

Sodium (8S,9R,10S,12R)-1-aza-10-(1-Hydroxyethyl)-11-oxo-4-[(E)-(pyrid-4-yl)methylene]-tricyclo-[7,2,0,0$^{3.8}$]-undec-2-ene-2-carboxylate Starting from intermediate intermediate 78 A (0.17 g) the title compound was obtained as a violet solid (0.14 g).

$^1$H-NMR (D2O): 8.30 (d); 7.19 (d); 6.24 (m); 4.15 (dd); 4.10 (m); 3.44 (dd); 3.04–2.90 (m); 2.84–2.72 (m); 2.20–2.02 (m); 1.90–1.74 (m); 1.54–1.20 (m); 1.12 (d).

EXAMPLE 6

Sodium (8S,9R,10S,12R)-1-aza-10-(1-Hydroxyethyl)-11-oxo-4-[(E)-(4-nitrophenyl)methylene]-tricyclo-[7,2,0,0$^{3.8}$]-undec-2-ene-2-carboxylate Starting from intermediate 78 (0.056 g) a crude product was obtained and then purified by preparative HPLC (mobile phase: MeCN-water, from 9:91 to 15:85) followed by lyophilization to give the title compound as a white solid (0.044 g).

IR: 3329 (OH),1761 (C=O) cm$^{-1}$. $^1$H-NMR (D2O): 8.06 (d); 7.36 (d); 6.34 (d); 4.16 (dd); 4.10 (m); 3.44 (dd); 2.97 (m); 2.76 (m); 2.10 (m); 1.81 (m); 1.41 (m); 1.12 (d).

EXAMPLE 7

Sodium (8S,9R,10S,12R)-1-aza-10-(1-Hydroxyethyl)-11-oxo-4-[(E)-(4-phenylthiazol-2-yl)methylene]-tricyclo-[7,2,0,0$^{3.8}$]-undec-2-ene-2-carboxylate Starting from intermediate 91 (0.030 g) a title compound was obtained as a yellow pale solid (0.015 g).

IR (nujol): 3410 (OH), 1770 (C=O), 1591 (C=O, C=C) cm$^{-1}$. $^1$H-NMR (D2O): 7.77–7.67 (m+s); 7.41–7.33 (m+m); 6.53 (d); 4.21 (dd); 4.14 (m); 3.50 (dd); 3.34 (m); 3.07 (m); 2.17 (m); 1.98–1.86 (m); 1.54 (m); 1.16 (d).

EXAMPLE 8

Sodium (8S,9R,10S,12R)-1-aza-10-(1-Hydroxyethyl)-11-oxo-4-[(E)-(3-(4'-pyridyl)phenyl)methylene]-tricyclo-[7,2,0,0$^{3.8}$]-undec-2-ene-2-carboxylate Starting from intermediate 92 (0.05 g) the title compound was obtained as a white solid (0.032 g).

IR: 1738 (C=O), 1587 (C=C) cm$^{-1}$; $^1$H-NMR (D2O): 8.45 (d); 7.94 (s); 7.73 (d); 6.52 (d); 4.21 (dd); 4.14 (m); 3.51 (dd); 3.35 (m); 3.08 (m); 2.18 (m); 2.00 (m); 1.88 (m); 1.55–1.1 (m); 1.16 (d).

EXAMPLE 9

Sodium (8S,9R,10S,12R)-1-aza-10-(1-Hydroxyethyl)-11-oxo-4-[(E)-(2,6-dimethylpyridin-4-yl)methylene]-tricyclo-[7,2,0,0$^{3.8}$]-undec-2-ene-2-carboxylate Starting from intermediate 83 (0.10 g) the title compound (0.092 g) was obtained.

IR: 3385 (OH); 1759 (C=O) cm$^{-1}$. $^1$H-NMR (D2O): 6.94 (s); 6.20 (d); 4.18 (dd ; 4.13 (m); 3.47 (dd); 2.969 (m); 2.79 (m); 2.35 (m); 2.09 (m); 1.84 (m); 1.60–1.10 (m); 1.15 (d).

EXAMPLE 10

Sodium (8S,9R,10S,12R)-1-aza-10-(1-Hydroxyethyl)-11-oxo-4-[(E)-(2-methylpyridin-4-yl)methylene]-tricyclo-[7,2,0,0$^{3.8}$]-undec-2-ene-2-carboxylate Starting from intermediate 79 (0.50 g) the crude compound was obtained and then purifed by RP18 chromatography (eluting with water to water-MeCN 95:5) to give the title compound (0.014 g).

IR: 3400–3340 (OH); 1755 (C=O) cm$^{-1}$. $^1$H-NMR: 8.19 (d); 7.12 (s); 7.06 (m); 4.17 (dd); 4.12 (m; 3.46 (dd); 2.99 (td); 2.78 (m); 2.10 (m); 2.37 (s); 1.90–1.80 (m); 1.5–1.35 (m); 1.13 (d).

EXAMPLE 11

Sodium (8S,9R,10S,12R)-1-aza-10-(1-Hydroxyethyl)-11-oxo-4-[(E)-[(benzofuran-2-yl)methylene]-tricyclo-[7,2,0,0$^{3.8}$]-undec-2-ene-carboxylate Starting from intermediate 84 (0.07 g) the title compound (0.07 g) was obtained.

IR: 1749–1607 (C=O). $^1$H-NMR: 7.52 (d); 7.41 (d); 7.22 (m); 7.16 (m); 6.70 (s); 6.20 (d); 4.19 (dd); 4.14 (m); 3.48 (dd); 3.35 (m); 3.03 (m); 2.16 (m); 2.00–1.80 (m); 1.52 (m); 1.15 (d).

EXAMPLE 12

Sodium (8S,9R,10S,12R)-1-aza-10-(1-Hydroxyethyl)-11-oxo-4-[(E)-[(2-chloropyrid-4-yl)methylene]-tricyclo-[7,2,0,0$^{3.8}$]-undec-2-ene-carboxylate Starting from intermediate 80 (0.130 g) the title compound (0.062 g) was obtained.

$^1$H-NMR: 8.09 (d); 7.24 (s); 7.12 (d); 6.19 (bs); 4.19 (dd); 4.09 (m); 3.45 (m); 2.98 (m); 2.74 (m); 2.08 (m); 1.81 (m); 1.42 (m); 1.10 (d).

EXAMPLE 13

Sodium (8S,9R,10S,12R)-1-aza-10-(1-Hydroxyethyl)-11-oxo-4-[(E)-[(2-furyl[3,2-c]pyridine)methylene]-tricyclo-[7,2,0,0$^{3.8}$]-undec-2-ene-carboxylate Starting from intermediate 81 (0.085 g the title compound (0.077 g) was obtained.

IR: 1760 (C=O) cm$^{-1}$. $^1$H-NMR: 8.61 (s); 7.41 (m); 8.18 (d); 7.38 (d); 6.70 (s); 6.15 (s); 4.15 (dd); 4.09 (m); 3.44 (t); 3.25 (m); 2.99 (m); 2.12 (m); 1.95–1.75 (m); 1.60–1.4 (m); 1.11 (d).

EXAMPLE 14

Sodium (8S,9R,10S,12R)-1-aza-10-(1-Hydroxyethyl)-11-oxo-4-[(E)-(2-aminopyrid-4-yl)methylene]-tricyclo-[7,2,0,0$^{3.8}$]-undec-2-ene-2-carboxylate Starting from intermediate 82 (0.05 g) the title compound (0.04 g) was obtained.

$^1$H-NMR (D2O): 7.73 (d), 6.57 (dd); 6.47 (s), 6.12 (d), 4.14 (dd); 4.04 (quint.); 3.43 (dd); 2.95 (m); 2.76 (m); 2.04 (m); 1.75–1.85 (m); 1.3–1.5 (m), 1.1 (d).

EXAMPLE 15

Sodium (8S,9R,10S,12R)-1-aza-10-(1-Hydroxyethyl)-11-oxo-4-[(E)-(4-chloro-3-nitrophenyl)methylene]-tricyclo-[7,2,0,0$^{3.8}$]-undec-2-ene-2-carboxylate Starting from intermediate 88 (0.085 g) the crude title compound was obtained and then purified by reverse phase filtration (eluting with water-MeCN) to give the title compound (0.040 g).

$^1$H-NMR (D2O): 7.78 (m); 7.50 (d); 7.42 (d); 6.28 (m); 4.19 (dd); 4.13 (m); 3.47 (m); 2.99 (m); 2.73 (m); 2.10 (m); 1.84 (m); 1.44 (m); 1.15 (d).

EXAMPLE 16

Sodium (8S,9R,10S,12R)-1-aza-10-(1-Hydroxyethyl)-11-oxo-4-[(E)-(benzothiophen-2-yl)methylene]-tricyclo-[7,2,0,0$^{3.8}$]-undec-2-ene-2-carboxylate Starting from intermediate 85 (0.150 g) the crude product was obtained and then purified by preparative HPLC (MeCN-water=16:84 as eluants) and lyophilized to give the title compound (0.072 g).

IR: 3337 (OH); 1749 (C=O); 1597 (C=O and C=N) cm$^{-1}$. $^1$H-NMR (D2O): 7.79 (d); 7.71 (d); 7.28 (m); 7.24 (s); 6.50 (s); 4.18 (dd); 4.14 (m); 3.47 (dd); 3.14 (m); 3.00 (m); 2.15 (m); 2.00–1.42 (m); 1.15 (d).

EXAMPLE 17

Sodium (8S,9R,10S,12R)-1-aza-10-(1-Hydroxyethyl)-11-oxo-4-[(E-)(benzothiophen-3-yl)methylene]-tricyclo-[7,2,0,0$^{3.8}$]-undec-2-ene-2-carboxylate Starting from intermediate 86 (0.085 g) the title compound was obtained as a beige solid (0.067 g).

IR: 1753 (C=O) cm$^{-1}$. $^1$H-NMR (D2O): 7.82 (d); 7.69 (d); 7.35 (s); 7.30 (m); 6.42 (s), 4.16 (dd); 4.10 (m); 3.43 (dd); 2.94 (m); 2.72 (d); 2.06 (m); 1.8 (m); 1.5–1.3 (m); 1.12 (d).

Using the same general procedure described for preparing example 2, the following compounds were prepared:

EXAMPLE 18

(8S,9R,10S,12R)-1-aza-10-(1-Hydroxyethyl)-11-oxo-4-[(E)-(4-(1'-(carbamoylmethyl)pyridinium-4-'-yl)thiophen-2-yl)methylene]-tricyclo-[7,2,0,0$^{3.8}$]-undec-2-ene-2-carboxylate Starting from intermediate 95 (0.117 g) the title compound (0.0375 g) was obtained.

$^1$H-NMR (D2O): 8.48 (d); 8.13 (s); 8.05 (d); 7.41 (s); 6.39 (m); 5.25 (s); 4.13 (dd); 4.09 (m); 3.43 (dd); 2.97 (m); 2.94 (m); 2.09 (m); 1.95–1.75 (m); 1.4–1.5 (m); 1.11 (d).

EXAMPLE 19

(8S,9R,10S,12R)-1-aza-10-(1-Hydroxyethyl)-11-oxo-4-[(E)-(N-(carbamoylmethyl)-2-furyl[3,2-c]pyridinium)methylene]-tricyclo-[7,2,0,0$^{3.8}$]-undec-2-ene-2-carboxylate Starting from intermediate 94 (0.04 g) the title compound was obtained as an orange solid (0.012 g).

IR: (nujol) 1770, 1693 (C=O) cm$^{-1}$. $^1$H-NMR (D2O): 8.91 (s); 8.40 (dd),7.90 (d); 6.96 (s); 6.25 (d); 5.36 (s), 4.18 (dd); 4.11 (m); 3.48 (dd); 3.24 (m); 3.05 (m); 2.21 (m); 1.95 (m); 1.83 (m); 1.51 (m); 1.12 (d).

As a further illustration of the present invention the following compounds were prepared according to the general procedures herewithin described for the prepartation of Examples 1 to 19.

EXAMPLE 20

Sodium (8S,9R,10S,12R)-1-aza-10-(1-Hydroxyethyl)-11-oxo-4-[(E)-(2-chloro-3-cyano-6-methylpyrid-4-yl)methylene]-tricyclo-[7,2,0,0$^{3.8}$]-undec-2-ene-2-carboxylate IR: 3396 (OH), 2230 (CN); 1755 (C=O) cm$^{-1}$.

EXAMPLE 21

Sodium (8S,9R,10S,12R)-1-aza-10-(1-Hydroxyethyl)-11-oxo-4-[(E)-(3-nitropyrid-4-yl)methylene]-tricyclo-[7,2,0,0$^{3.8}$]-undec-2-ene-2-carboxylate IR: 1751 (C=O) 1595, (C=C) cm$^{-1}$.

EXAMPLE 22

Sodium (8S,9R,10S,12R)-1-aza-10-(1-Hydroxyethyl)-11-oxo-4-[(E)-(2-chloro-6-methoxypyrid-4-yl)methylene]-tricyclo-[7,2,0,0$^{3.8}$]-undec-2-ene-2-carboxylate IR: 1755 (C=O), 1593 (C=C) cm$^{-1}$.

EXAMPLE 23

Sodium (8S,9R,10S,12R)-1-aza-10-(1-Hydroxyethyl)-11-oxo-4-[(E)-(2-acetylaminopyrid-4-yl)methylene]-tricyclo-[7,2,0,0$^{3.8}$]-undec-2-ene-2-carboxylate $^1$H-NMR (D2O): 8.12 (d), 7.48 (bs), 7.03 (d), 6.25 (d); 4.19 (dd); 4.14 (m); 3.47 (dd); 3.0 (m); 2.82 (m); 2.10 (m); 1.85 (m); 1.47 (m), 1.15 (d).

EXAMPLE 24

Sodium (8S,9R,10S,12R)-1-aza-10-(1-Hydroxyethyl)-11-oxo-4-[(E)-(2-cyanopyrid-4-yl)methylene]-tricyclo-[7,2,0,0$^{3.8}$]-undec-2-ene-2-carboxylate IR: 1755 (C=O), 1589 (C=C) cm$^{-1}$.

EXAMPLE 25

Sodium (8S,9R,10S,12R)-1-aza-10-(1-Hydroxyethyl)-11-oxo-4-[(E)-(2-diethylaminooxazolo[4,5b]pyrid-7-yl)methylene]-tricyclo-[7,2,0,0$^{3.8}$]-undec-2-ene-2-carboxylate $^1$H-NMR (D2O): 7.84 (d); 7.80 (d); 6.24 (s); 4.19 (dd); 4.12 (m); 3.48 (dd); 3.00 (m); 2.63 (m); 2.09 (m); 1.85 (m); 1.45 (m); 1.2–1.1 (m).

EXAMPLE 26

Sodium (8S,9R,10S,12R)-1-aza-10-(1-Hydroxyethyl)-11-oxo-4-[(E)-(4-tert-butylphenyl)methylene]-tricyclo-[7,2,0,0$^{3.8}$]-undec-2-ene-2-carboxylate $^1$H-NMR (D2O): 7.37 (d); 7.20 (d); 6.28 (s); 4.16 (dd); 4.13 (m); 3.44 (dd); 2.95 (m); 2.78 (m); 2.08 (m); 1.84 (m); 1.46–1.10 (m); 1.17 (s); 1.13 (d).

EXAMPLE 27

Sodium (8S,9R,10S,12R)-1-aza-10-(1-Hydroxyethyl)-11-oxo-4-[(E)-(pyrid-2-yl)methylene]-tricyclo-[7,2,0,0$^{3.8}$]-undec-2-ene-2-carboxylate $^1$H-NMR (D2O): 8.32 (d); 7.67 (m); 7.26 (d); 7.13 (m); 6.27 (bs); 4.15 (dd); 4.09 (m); 3.44 (m); 2.99 (m); 2.89 (m); 2.05 (m); 1.83–1.10 (m); 1.11 (d).

EXAMPLE 28

Sodium (8S,9R,10S,12R)-1-aza-10-(1-Hydroxyethyl)-11-oxo-4-[(E)-(4-methoxyphenyl)methylene]-tricyclo-[7,2,0,0$^{3.8}$]-undec-2-ene-2-carboxylate $^1$H-NMR: 7.17 (d); 6.85 (d); 6.23 (s); 4.12 (m); 3.69 (s); 3.41 (bm); 2.91 (m); 2.75 (d); 2.05 (t); 1.79 (m); 1.50–1.30 (m); 1.12 (d).

EXAMPLE 29

Sodium (8S,9R,10S,12R)-1-aza-10-(1-Hydroxyethyl)-11-oxo-4-[(E)2-cyanophenyl)methylene]-tricyclo-[7,2,0,0$^{3.8}$]-undec-2-ene-2-carboxylate IR: 3385 (OH); 2200 (C≡N); 1755 (C=O) cm$^{-1}$.

EXAMPLE 30

Sodium (8S,9R,10S,12R)-1-aza-10-(1-Hydroxyethyl)-11-oxo-4-[(E)-(2-fluoro-5-nitrophenyl)methylene]-tricyclo-[7,2,0,0$^{3.8}$]-undec-2-ene-2-carboxylate IR: 3500–2600 (OH); 1757 (C=O); 1610–1591 (C=C and C=N) cm$^{-1}$.

EXAMPLE 31

Sodium (8S,9R,10S,12R)-1-aza-10-(1-Hydroxyethyl)-11-oxo-4-[(E)-(4-trifluoromethylphenyl)methylene]-tricyclo-[7,2,0,0$^{3.8}$]-undec-2-ene-2-carboxylate $^1$H-NMR (D2O): 7.52 (d); 7.31 (d); 6.30 (s); 4.13 (dd); 4.08 (m); 3.41 (dd); 2.94 (m); 2.72 (d); 2.05 (m); 1.79 (m); 1.41 (m); 1.36 (m); 1.10 (d).

EXAMPLE 32

Sodium (8S,9R,10S,12R)-1-aza-10-(1-Hydroxyethyl)-11-oxo-4-[(E)-(4-(4'-pyridyl)-thiopen-2-yl)methylene]-tricyclo-[7,2,0,0$^{3.8}$]-undec-2-ene-2-carboxylate $^1$H-NMR (D2O): 8.32 (d); 7.67 (s); 7.48 (d); 7.27 (s); 6.35 (s); 4.12 (dd); 4.10 (m); 3.41 (t); 3.26 (m); 2.90 (m); 2.06 (m); 1.90–1.78 (m); 1.5–1.4 (m); 1.10 (d).

EXAMPLE 33

Sodium (8S,9R,10S,12R)-1-aza-10-(1-Hydroxyethyl)-11-oxo-4-[(E)-(3-(4'-pyridyl)thiophen-2-yl)methylene]-tricyclo-[7,2,0,0$^{3.8}$]-undec-2-ene-2-carboxylate $^1$H-NMR D$_2$O): 8.36 (d); 7.39 (d); 7.36 (d); 7.13 (m); 6.30 (s); 4.10 (dd); 4.08 (m); 3.38 (dd); 2.89 (m); 2.76 (m); 1.95 (m); 1.8–1.2 (m); 1.09 (d).

EXAMPLE 34

Sodium (8S,9R,10S,12R)-1-aza-10-(1-Hydroxyethyl)-11-oxo-4-[(E)-(3-cyanophenyl)methylene]-tricyclo-[7,2,0,0$^{3.8}$]-undec-2-ene-2-carboxylate $^1$H-NMR: 7.52 (s); 7.57.4 (m); 7.34 (t); 6.23 (s); 4.12 (dd); 4.07 (m); 3.4 (dd); 2.98 (m); 2.66 (m); 2.02 (m); 1.77 (m); 1.44–1.28 (m); 1.09 (d).

EXAMPLE 35

Sodium (8S,9R,10S,12R)-1-aza-10-(1-Hydroxyethyl)-11-oxo-4-[(E)-(3-trifluoromethylphenyl)methylene]-tricyclo-[7,2,0,0$^{3.8}$]-undec-2-ene-2-carboxylate $^1$H-NMR (D2O): 7.54–7.38 (m); 6.351 (s); 4.18 (dd); 4.13 (m), 3.46 (t); 2.99 (m) 2.75 (m); 2.1 (m), 1.84 (m); 1.56–1.346, (m); 1.15 (d).

EXAMPLE 36

(8S,9R,10S,12R)-1-aza-10-(1-Hydroxyethyl)-11-oxo-4-[(E)-(1-methylpyridinium-4-yl)methylene]-tricyclo-[7,2,0,0$^{3.8}$]-undec-2-ene-2-carboxylate $^1$H-NMR (D2O): 8.42 (d); 7.68 (d); 6.38 (d); 4.19 (dd); 4.13 (s); 4.16–4.06 (m); 3.50 (dd); 3.06 (m); 2.88–2.76 (m); 2.34–2.18 (m); 2.00–1.76 (m); 1.62–1.20 (m); 1.12 (d).

EXAMPLE 37

(8S,9R,10S,12R)-1-aza-10-(1-Hydroxyethyl)-11-oxo-4-[(E)-(1-methylpyridinium-3-yl)methylene]-tricyclo-[7,2,0,0$^{3.8}$]-undec-2-ene-2-carboxylate $^1$H-NMR (D2O): 8.53 (bs); 8.43 (dd); 8.23 (d); 7.81 (m); 6.28 (s); 4.22 (s); 4.17 (dd); 4.10 (m); 3.46 (m); 3.01 (m); 2.62 (m); 2.15 (m); 1.82 (m); 1.60–1.40 (m); 1.11 (d).

EXAMPLE 38

Sodium (8S,9R,10S,12R)-1-aza-10-(1-Hydroxyethyl)-11-oxo-4-[(E)-(2-hydroxyphenyl)methylene]-tricyclo-[7,2,0,0$^{3.8}$]-undec-2-ene-2-carboxylate $^1$H-NMR (D2O):7.12 (m); 6.84 (m); 6.79 (m); 6.24 (m); 4.18 (dd); 4.13 (m), 3.45 (dd); 3.0 (m); 2.52 (m); 2.0 (m); 1.8 (m); 1.5–1.35 (m), 1.15 (d).

EXAMPLE 39

Sodium (8S,9R,10S,12R)-1-aza-10-(1-Hydroxyethyl)-11-oxo-4-[(E)-(3-hydroxyphenyl)methylene]-tricyclo-[7,2,0,0$^{3.8}$]-undec-2-ene-2-carboxylate $^1$H-NMR (D2O): 7.17 (t); 6.80 (d); 6.72 (s), 6.67 (m), 6.25 (d), 4.17 (dd), 4.14 (m); 3.45 (m); 2.94 (m); 2.8 (m); 1.82 (m); 1.5–1.34 (m); 1.25–1.1 (m); 1.15 (d).

EXAMPLE 40

Potassium (8S,9R,10S,12R)-1-aza-10-(1-Hydroxyethyl)-11-oxo-4-[(E)-(pyrid-3-yl)methylene]-tricyclo-[7,2,0,0$^{3.8}$]-undec-2-ene-2-carboxylate $^1$H-NMR (D2O): 8.29 (bs); 8.21 (dd); 7.63 (m); 7.27 (m); 6.32–6.25 (m); 4.15 (dd); 4.10 (m); 3.90–3.60 (m); 3.43 (m); 2.96 (m); 2.70 (m); 2.55 (m); 2.2–1.40 (m); 1.12 (d).

EXAMPLE 41

Sodium (8S,9R,10S,12R)-1-aza-10-(1-Hydroxyethyl)-11-oxo-4-[(E)-[(2-methoxypyrid-4-yl)methylene]-triciclo-[7,2,0,0$^{3.8}$]-undec-2-ene-2-carboxylate $^1$H-NMR: 7.92 (d); 6.85 (d); 6.66 (s); 6.22 (s); 4.18 (dd); 4.13 (m); 378 (s); 3.46 (dd); 2.99 (m); 2.79 (m); 2.09 (m); 1.84 (m); 1.5–1.4 (m); 1.15 (d).

EXAMPLE 42

Sodium (8S,9R,10S,12R)-1-aza-10-(1-Hydroxyethyl)-11-oxo-4-[(E)-(2-methyl-4-(4'-pyridyl)thiazol-5-yl)methylene]-tricyclo-[7,2,0,0$^{3.8}$]-undec-2-ene-2-carboxylate $^1$H-NMR (D2O): 8.46 (m); 7.53 (m); 6.21 (m); 4.14–4.10 (dd+m); 3.39 (dd); 2.82 (m); 2.57–2.52 (s+m); 1.86–1.36 (m+m); 1.2–1.13 (m+d).

EXAMPLE 43

Sodium (8S,9R,10S,12R)-1-aza-10-(1-Hydroxyethyl)-11-oxo-4-[(E)-(pyrimid-4-yl)methylene]-tricyclo-[7,2,0,0$^{3.8}$]-undec-2-ene-2-carboxylate $^1$H-NMR (D2O): 8.90 (d); 8.56 (d); 7.35 (dd); 6.26 (d); 4.21 (dd); 4.14 (m); 3.50 (dd); 3.13–3.07 (m+m); 2.14 (m); 1.94–1.82 (m); 1.56–1.24 (m); 1.15 (d).

EXAMPLE 44

Sodium (8S,9R,10S,12R)-1-aza-10-(1-Hydroxyethyl)-11-oxo-4-[(E)-[(5-methylthiopen-2-yl)methylene]-triciclo-[7,2,0,0$^{3.8}$]-undec-2-ene-carboxylate $^1$H-NMR: 6.73 (d); 6.61 (s); 6.30 (s); 4.2–4.0 (m); 3.40 (dd); 2.93 (m); 2.30 (s); 2.10–1.7 (m); 1.42 (m); 1.10 (d).

EXAMPLE 45

Sodium (8S,9R,10S,12R)-1-aza-10-(1-Hydroxyethyl)-11-oxo-4-[(E)-[2-chloro-6-methylpyrid-4-yl)methylene]-tricyclo-[7,2,0,0$^{3.8}$]-undec-2-ene-2-carboxylate $^1$H-NMR: 7.07 (s); 7.01 (s); 6.16 (s); 4.19 (dd); 4.13 (m); 3.47 (m); 2.98 (m); 2.76 (m); 2.33 (s); 2.09 (m); 1.84 (m); 1.45 (m); 1.15 (d).

EXAMPLE 46

Sodium (8S,9R,10S,12R)-1-aza-10-(1-Hydroxyethyl)-11-oxo-4-[(E)-(4-cyanophenyl)methylene]-triciclo-[7,2,0,0$^{3.8}$]-undec-2-ene-carboxylate $^1$H-NMR: 7.32–7.20 (m); 7.06 (m); 6.98 (m); 6.94 (d); 6.84 (bs); 6.82 (m); 6.23 (m); 4.12 (dd); 4.08 (m); 3.41 (dd); 2.91 (m); 2.72 (m); 1.98 (m); 1.8–1.7 (m); 1.5–1.3 (m); 1.10 (d).

EXAMPLE 47

Sodium (8S,9R,10S,12R)-1-aza-10-(1-Hydroxyethyl)-11-oxo-4-[(E)-(pyrimidin-5-yl)methylene]-triciclo-[7,2,0,0$^{3.8}$]-undec-2-ene-carboxylate $^1$H-NMR: 8.83 (s);8.60 (s); 6.22 (d); 4.20 (dd); 4.14 (m); 3.48 (dd); 3.68 (m); 3.02 (m); 2.15 (m); 1.86 (m); 1.54–1.40 (m); 1.15 (d).

EXAMPLE 48

Sodium (8S,9R,10S,12R)-1-aza-10-(1-Hydroxyethyl)-11-oxo-4-[(E)-(guinolin-4-yl)methylene]-triciclo-[7,2,0,0$^{3.8}$]-undec-2-ene-2-carboxylate $^1$H-NMR (D2O): 8.68 (d); 8.07 (d); 7.94 (d); 7.72 (t); 7.57 (t); 7.34 (d); 6.76 (d); 4.25 (dd); 4.17 (m); 3.51 (dd); 3.10 (m); 2.46 (m); 2.00 (m); 1.87 (m); 1.80 (m); 1.50 (m); 1.44 (m); 1.18 (d).

EXAMPLE 49

Sodium (8S,9R,10S,12R)-1-aza-10-(Hydroxyethyl)-11-oxo-4-[(E)-[(2-trifluoromethylphenyl)methylene]-triciclo-[7,2,0,0$^{3.8}$]-undec-2-ene-carboxylate $^1$H-NMR: 7.57 (d); 7.43 (t); 7.27 (m); 6.39 (bs); 4.12 (dd); 4.07 (m); 3.40 (dd); 2.95 (m); 2.37 (m); 1.94 (m); 1.75 (m); 1.6–1.22 (m); 1.08 (d).

EXAMPLE 50

Sodium (8S,9R,10S,12R)-1-aza-10-(1-Hydroxyethyl)-11-oxo-4-[(E)-[(3-phenoxyphenyl)methylene]-triciclo-[7,2,0,0$^{3.8}$]-undec-2-ene-carboxylate $^1$H-NMR: 7.32–7.20 (m); 7.06 (m); 6.98 (m); 6.94 (d); 6.84 (bs); 6.82 (m); 6.23 (d); 4.12 (dd); 4.08 (m); 3.41 (dd); 2.91 (m); 2.72 (m); 1.98 (m); 1.8–1.7 (m); 1.5–1.3 (m); 1.10 (d).

EXAMPLE 51

Sodium (8S,9R,10S,12R)-1-aza-10-(1-Hydroxyethyl)-11-oxo-4-[(E)-(3,4-difluorophenyl)methylene]-tricyclo-[7,2,0,0$^{3.8}$]-undec-2-ene-2-carboxylate $^1$H-NMR (D2O): 7.12–7.0 (m); 6.93 (m); 6.19 (s); 4.2–4.0 (m); 3.41 (m); 2.92 (t); 2.71 (m); 2.02 (m); 1.78 (m); 1.4 (m); 1.11 (d).

EXAMPLE 52

Sodium (8S,9R,10S,12R)-1-aza-10-(1-Hydroxyethyl)-11-oxo-4-[(E)-(pyrimid-4-yl)methylene]-tricyclo-[7,2,0,0$^{3.8}$]-undec-2-ene-2-carboxylate $^1$H-NMR (D2O): 8.90 (d); 8.56 (d); 7.35 (dd); 6.26 (d); 4.21 (dd); 4.14 (m); 3.50 (dd); 3.13–3.07 (m+m); 2.14 (m); 1.94–1.82 (m); 1.56–1.24 (m); 1.15 (d).

EXAMPLE 53

Sodium (8S,9R,10S,12R)-1-aza-10-(1-Hydroxyethyl)-11-oxo-4-[(E)-(N-ethylcarbazol-4-yl)methylene]-tricyclo-[7,2,0,0$^{3.8}$]-undec-2-ene-2-carboxylate $^1$H-NMR (D2O): 8.10–8.04 (s+d); 7.58–7.36 (m+t); 7.19 (t); 6.51 (m); 4.32–4.14 (m); 3.47 (dd); 2.94 (m); 2.22 (m); 1.84 (m); 1.56–1.34 (m); 1.25 (t); 1.16 (d).

EXAMPLE 57

Sodium (8S,9S,10S,12R)-1-aza-10-(1-Hydroxyethyl)-11-oxo-4-{(E)-[4'(piperidin-4-yl)thiazol-2'-yl]-methylene}-tricyclo-[7,2,0,0$^{3.8}$]-undec-2-ene-2-carboxylate To a solution of intermediate 104 (0.43 g) in dry DMF (10 ml) at r.t., dimedone (0.43 g), triphenylphosphine (0.009 g) and tetrakis(triphenylphosphine) palladium (0.087 g) were added. The reaction was stirred for 1 h at r.t., then Et$_2$O was added until a precipitate formed. The mixture was centrifuged two times with EA and two times with EE, decanting the supernatant, then the solid was dried in vacuo, purified by preparative HPLC [Dynamax column (Rainin): 25 cm×2.1 cm, 8 μm; flow: 10 ml/min; phase:H$_2$O/MeCN 90/10 to 40/60 in 20 min (linear gradient); u.v.; 225 nm; loop: 2 ml] and lyophilized to give the title compound as a white solid (0.17 g).

1H-NMR (D2O): 7.14 (s); 6.46 (md); 4.20 (dd); 4.13 (m); 3.49 (dd); 3.42 (m); 3.15 (m); 3.1–2.98 (m); 2.14 (m); 1.95 (m); 1.9–1.7 (m); 1.5 (m); 1.14 (d).

EXAMPLE 58

Sodium (8S,9R,10S,12R)-1-aza-10-(1-Hydroxyethyl)-6-thia-11-oxo-4-[(E)-(4-pyridyl)methylene]-tricyclo-[7,2,0,0$^{3.8}$]-undec-2-ene-2-carboxylate TPP (0.004 g) and tetrakis(triphenylphosphine)palladium (0.025 g) were added to a stirred solution of intermediate 111 (0.17 g) in dry THF (10 mL), then sodium 2-ethylhexanoate (0.068 g) dissolved in dry THF (2.0 mL) was added and the mixture was stirred at 23° C., under a nitrogen atmosphere, for 15 min. Then EE was added until a violet precipitate formed. The mixture was centrifuged 3 times, decanting the supernatant and washing the remaining solid with EE each time, then the solid was dried in vacuo, purified by preparative HPLC (MeCN-water=15–85 as eluants) and freeze dried to give t he title compound (0.081 g).

IR: 3323 (OH); 1759 (C=O). $^1$H-NMR (D2O): 8.37 (d); 7.25 (dd); 7.21 (d); 4.14 (m); 3.53 (d); 3.50 (dd); 3.46 (m); 3.39 (d); 2.97 (t); 2.70 (dd); 1.15 (d).

EXAMPLE 59

Sodium (8S,9R,10S,12R)-1-aza-10-(1-Hydroxyethyl)-11-oxo-4-[(E)-(pyrid-4-yl)methylene]-tricyclo-[7,2,0,0$^{3.8}$]-undec-2-ene-2-carboxylate Intermediate 117 (0.05 g) was dissolved in iso-propyl alcohol (0.5 ml), and treated with a solution of palladium tetrakis(triphenylphosphine) (0.3 ml of 4 ml tetrahydrofuran solution containing 0.01 g catalyst+trace (<0.001 g) triphenylphosphine; 0.46 mol %) followed by an ethyl acetate solution of sodium ethylhexanoate (0.25 ml, 0.5M in ethyl acetate). Reaction was monitored by mass spec and was complete within 60 minutes. Deloxan THP II resin (0.25 g wet, washed successively with isopropanol to give 0.05 g dry) was added, and the suspension stirred for 6 hrs at room temperature (flask covered in aluminium foil). The resin was removed by filtration, and the filtrate evaporated to leave pale residue, which was dissolved in tetrahydrofuran (0.5 ml). The solution was chilled (ice bath) as diethyl ether (5 ml) was added dropwise, and the resulting suspension chilled a further 30 minutes. The product was isolated by filtration (glove bag with nitrogen atmosphere), washed with diethyl ether (5 ml) and sucked dry to give the title compound leave off-white solid (0.033 g).

EXAMPLE 60

Sodium (8S,9R,10S,12R)-1-aza-10-(1-Hydroxyethyl)-11-oxo-4-[(E)-(pyrid-4-yl)methylene]-tricyclo-[7,2,0,0$^{3.8}$]-undec-2-ene-2-carboxylate Intermediate 120 (4.24 g) is dissolved in acetone (80 ml.) then dipropylamine (1.36 ml, 1.3 eq.) is added and the mixture is stirred at 20° C. for 4 h. After 30 min. a white precipitate appears. A solution of sodium 2-ethylhexanoate (1.1 g) in acetone (21 l) was added and the mixture was stirred at ambient temperature for 2.5 h. The solid was filtered and washed with acetone (4×10 ml) in dry box (N₂) then dried under vacuum at 25° C. for 15 h to give the title compound (2.18 g) as a white powder.

Pharmacy Example

Dry Powder for Injection / active ingredient  500 mg per vial.

Fill sterile vials with the sterile active ingredient. Purge the vial head space with sterile nitrogen: close the vials using rubber plugs and metal oversells (applied by crimping). The product for injection may be constituted by dissolving in Water for Injection (10 ml) or other suitable sterile vehicle for injection shortly before administration.

Conveniently the active ingredient is a salt e.g. sodium salt of a compound of formula (I).

The antibacterial activity of the compounds of the invention may be readily determined using conventional test procedures. For example the antibacterial activity of the compounds of the invention was determined using a standard mictoriter broth serial dilution test. In this test the broth was incubated with approximately 10⁵ colony forming units of the test organism and incubated at 35° for 18 hours in the presence of test compound. Results obtained using this test for activity against strains of MRSA and MRSE are given below.

In this list the compounds of the invention were tested using this procedure against 23 strains of MRSA and 10 strains of MRSE and the resultant minimum inhibitory concentrations (MIC90) in mg/litre determined. The results obtained with a number of the compounds of the invention are given below.

| Ex No | MRSA MIC90 mg/l | MRSE MIC90 mg/l |
|---|---|---|
| 1 | 8 | 4 |
| 3 | 4 | 2 |
| 5 | 4 | 2 |
| 6 | 2 | 2 |
| 7 | 4 | 2 |
| 8 | 2 | 2 |
| 9 | 8 | 4 |
| 10 | 8 | 4 |
| 11 | 4 | 2 |
| 12 | 4 | 2 |
| 13 | 4 | 4 |
| 14 | 8 | 4 |
| 15 | 4 | 2 |
| 16 | 2 | 1 |
| 17 | 4 | 2 |
| 18 | 4 | 2 |

Compounds of the invention are in general non-toxic and therapeutically effective doses. For example the compound of Example 5 showed no untoward effects when administered to rats at doses up to 1000 mg/kg.

5. Sodium (8S,9R,10S,12R)-1-aza-10-(1-hydroxyethyl)-11-oxo-4-[(E)-(pyridin-4-yl)methylene]-tricyclo-[7,2,0,0³·⁸]-undec-2-ene-2-carboxylate.
6. A compound selected from;
   Sodium (8S,9R,10S,12R)-1-aza-10-(1-hydroxyethyl)-11-oxo-4-[(E)-phenylmethylene]-tricyclo-[7,2,0,0³·⁸]-undec-2-ene-2-carboxylate
   Sodium (8S,9R,10S,12R)-1-aza-10-(1-hydroxyethyl)-11-oxo-4-[(E)-4-(4'-pyridyl)thiazol-2-yl)methylene]-tricyclo-[7,2,0,0³·⁸]-undec-2-ene-2-carboxylate
   Sodium (8S,9R,10S,12R)-1-aza-10-(1-hydroxyethyl)-11-oxo-4-[(E)-(benzothiazol-2-yl)methylene]-tricyclo-[7,2,0,0³·⁸]-undec-2-ene-2-carboxylate
   Sodium (8S,9R,10S,12R)-1-aza-10-(1-hydroxyethyl)-11-oxo-4-[(E)-(4-(4'-(piperidin-4-yl)thiazol-2-yl) methylene]-tricyclo-[7,2,0,0³·⁸]-undec-2-ene-2-carboxylate
   Sodium (8S,9R,10S,12R)-1-aza-10-(1-hydroxyethyl)-11-oxo-4-[(E)-(4-nitrophenyl)methylene]-tricyclo-[7,2,0,0³·⁸]-undec-2-ene-2-carboxylate
   Sodium (8S,9R,10S,12R)-1-aza-10-(1-hydroxyethyl)-11-oxo-4-[(E)-(4-phenylthiazol-2-yl)methylene]-tricyclo-[7,2,0,0³·⁸]-undec-2-ene-2-carboxylate
   Sodium (8S,9R,10S,12R)-1-aza-10-(1-hydroxyethyl)-11-oxo-4-[(E)-(3-(4'-pyridyl)phenyl)methylene]-tricyclo-[7,2,0,0³·⁸]-undec-2-ene-2-carboxylate
   Sodium (8S,9R,10S,12R)-1-aza-10-(1-hydroxyethyl)-11-oxo-4-[(E)-(2,6-dimethylpyridin-4-yl)methylene]-tricyclo-[7,2,0,0³·⁸]-undec-2-ene-2-carboxylate
   Sodium (8S,9R,10S,12R)-1-aza-10-(1-hydroxyethyl)-11-oxo-4-[(E)-(2-methylpyridin-4-yl)methylene]-tricyclo-[7,2,0,0³·⁸]-undec-2-ene-2-carboxylate
   Sodium (8S,9R,10S,12R)-1-aza-10-(1-hydroxyethyl)-11-oxo-4-[(E)-[(benzofuran-2-yl)methylene]-tricyclo-[7,2,0,0³·⁸]-undec-2-ene-carboxylate
   Sodium (8S,9R,10S,12R)-1-aza-10-(1-hydroxyethyl)-11-oxo-4-[(E)-[(2-furyl[3,2-c]pyridine)methylene]-tricyclo-[7,2,0,0³·⁸]-undec-2-ene-2-carboxylate.
   Sodium (8S,9R,10S,12R)-1-aza-10-(1-hydroxyethyl)-11-oxo-4-[(E)-[(2-furyl[3,2-c]pyridine)methylene]-triciclo-[7,2,0,0³·⁸]-undec-2-ene-2-carboxylate.
   Sodium (8S,9R,10S,12R)-1-aza-10-(1-hydroxyethyl)-11-oxo-4-[(E)-(2-aminopyrid-4-yl)methylene]-tricyclo-[7,2,0,0³·⁸]-undec-2-ene-2-carboxylate
   Sodium (8S,9R,10S,12R)-1-aza-10-(1-hydroxyethyl)-11-oxo-4-[(E)-(4-chloro-3-nitro-phenyl)methylene]-tricyclo-[7,2,0,0³·⁸]-undec-2-ene-2-carboxylate
   Sodium (8S,9R,10S,12R)-1-aza-10-(1-hydroxyethyl)-11-oxo-4-[(E)-(benzothiophen-2-yl)methylene]-tricyclo-[7,2,0,0³·⁸]-undec-2-ene-2-carboxylate
   Sodium (8S,9R,10S,12R)-1-aza-10-(1-hydroxyethyl)-11-oxo-4-[(E)-(benzothiophen-3-yl)methylene]-tricyclo-[7,2,0,0³·⁸]-undec-2-ene-2-carboxylate
   Sodium (8S,9S,10S,12R)-1 aza-10-(1-hydoxyethyl)-6-thia-11-oxo-4-[(E)-(4-pyridyl)methylene-tricyclo-[7,200³·⁸]indec-2-ene-2-carboxylate.

What is claimed is:
1. A compound of formula (I)

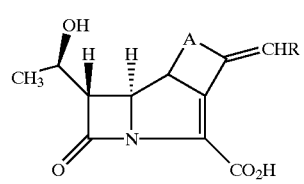

(I)

salts or metabolically labile esters, therefore;
  wherein R represents:
    a phenyl or a monocyclic 5 or 6 membered heteroaryl group in which the 5-membered ring contains 1 or 2 heteroatoms selected from the group consisting of oxygen, sulphur and nitrogen, and the 6-membered ring contains 1 or 2 nitrogen atoms, in which such R groups may be substituted by one to 3 substituents which may be the same or different and selected from:
straight or branched $C_{2-6}$ alkyl, straight or branched $C_{3-6}$ alkenyl, straight or branched $C_{2-6}$ alkynyl, such groups may be substituted by one or more groups selected from the group consisting of $C_{1-4}$ alkyl, halogen, hydroxy, carboxyl, nitro, cyano, trifluoromethyl, trifluoromethoxy, and phenyl; halogen; cyano; nitro; trifluoromethyl; by one or two $(CH_2)_nR_1$ groups,
wherein n is zero or an integer from 1 to 4 and
$R_1$ is hydroxy, $C_{1-4}$ alkoxy, $C_{1-4}$ alkanoyl-amino, $NR_2R_3$ (wherein $R_2$ and $R_3$ independently represent hydrogen or $C_{1-4}$ alkyl), a phenyl optionally substituted by one to 3 substituents which may be the same or different and selected from:
straight or branched $C_{2-6}$ alkyl, straight or branched $C_{3-6}$ alkenyl, straight or branched $C_{2-6}$ alkynyl, such groups may be substituted by one or more groups selected from the group consisting of by $C_{1-4}$ alkyl, halogen, hydroxy, carboxyl, nitro, cyano, trifluoromethyl, trifluoromethoxy; phenyl; halogen; cyano; nitro; or trifluoromethyl; phenoxy, monocyclic heteroaryl, $COR_4$ (wherein $R_4$ is hydroxy $C_{1-4}$ alkoxy or $NR_2R_3$), or $SO_2R_5$, (wherein $R_5$ is $C_{1-4}$ alkyl or the group $NR_2R_3$);
or R represents
a fused bicyclic heteroaryl containing 9 or 10 ring members having at least one heteroatom selected from oxygen, sulphur and nitrogen; or a fused tricyclic heteroaryl containing 13 or 14 ring members having at least one heteroatom selected from oxygen, sulphur and nitrogen, in which such R groups may be substituted by one to 2 substituents which may be the same or different and selected from:
straight or branched $C_{2-6}$ alkyl, halogen, cyano, nitro, trifluoromethyl, $NR_2R_3$ (wherein $R_2$ and $R_3$ independently represent hydrogen or $C_{1-4}$ alkyl);
or R represents
a phenyl fused to one 5 or 6 membered saturated or unsaturated carbocyclic group to form a fused bicyclic carbocyclic group or a phenyl fused to two phenyl groups to form a fused tricyclic group;
A represents a propylene chain or A is a chain of 3 members one of which is selected from an oxygen or sulphur atom or the group NH or a substituted derivative of the —NH— and the other two members are methylene groups.

2. A compound as claimed in claim 1 wherein A is a group $(CH_2)_3$, $CH_2SCH_2$, $CH_2OCH_2$ or $CH_2NHCH_2$.

3. A compound as claimed in claim 1 wherein A is a propylene chain.

4. A compound as claimed in claim 2 wherein A is a propylene chain.

5. A compound as claimed in claim 1 wherein R is pyridyl, phenyl or phenyl substituted by one or two substituents which may be the same or different selected from the group consisting of fluorine, chlorine, nitro, cyano, hydroxy, hydroxymethyl, phenoxy, and pyridyl.

6. A compound as claimed in claim 2 wherein R is pyridyl, phenyl or phenyl substituted by one or two substituents which may be the same or different selected from the group consisting of fluorine, chlorine, nitro, cyano, hydroxy, hydroxymethyl, phenoxy, and pyridyl.

7. A compound as claimed in claim 3 wherein R is pyridyl, phenyl or phenyl substituted by one or two substituents which may be the same or different selected from the group consisting of fluorine, chlorine, nitro, cyano, hydroxy, hydroxymethyl, phenoxy, and pyridyl.

8. A compound as claimed in claim 4 wherein R is pyridyl, phenyl or phenyl substituted by one or two substituents which may be the same or different selected from the group consisting of fluorine, chlorine, nitro, cyano, hydroxy, hydroxymethyl, phenoxy, and pyridyl.

9. A process for the preparation of compounds of formula (I) of as defined in claim 1 which comprises the cyclisation of a compound of formula (II) wherein A and R have the meaning as defined in formula (I) or are protected derivatives thereof, $R_6$ is hydrogen atom or hydroxyl protecting group and $R_7$ is hydrogen or a carboxyl protecting group;

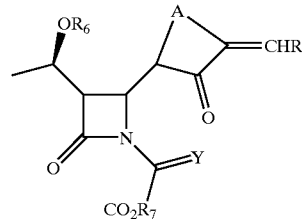

(II)

Y is an oxygen atom or a phosphoranylidene group, and if required or desired subjecting the resulting compound prior to or subsequent to any separation into its stereochemical isomers, to one or more of the following operations:
a) removal of one or more protecting groups
b) conversion of a compound in which $R_7$ is a hydrogen atom or a carboxyl protecting group into a salt of an inorganic or organic base, an acid addition salt thereof or a metabolically labile ester thereof.

10. A pharmaceutical composition comprising a compound as claimed in 1 in admixture with one or more physiologically acceptable carriers or excipients.

11. A pharmaceutical composition comprising a compound as claimed in 2 in admixture with one or more physiologically acceptable carriers or excipients.

12. A pharmaceutical composition comprising a compound as claimed in 3 in admixture with one or more physiologically acceptable carriers or excipients.

* * * * *